US009226976B2

(12) United States Patent
Flotte et al.

(10) Patent No.: US 9,226,976 B2

(45) Date of Patent: Jan. 5, 2016

(54) RAAV-BASED COMPOSITIONS AND METHODS FOR TREATING ALPHA-1 ANTI-TRYPSIN DEFICIENCIES

(75) Inventors: Terence Flotte, Holden, MA (US); Christian Mueller, Jefferson, MA (US)

(73) Assignee: University of Massachusetts, Boston, MA (US)

(*) Notice: Subject to any disclaimer, the term of this patent is extended or adjusted under 35 U.S.C. 154(b) by 12 days.

(21) Appl. No.: 14/113,118

(22) PCT Filed: Apr. 20, 2012

(86) PCT No.: PCT/US2012/034446

§ 371 (c)(1), (2), (4) Date: Feb. 3, 2014

(87) PCT Pub. No.: WO2012/145624

PCT Pub. Date: Oct. 26, 2012

(65) Prior Publication Data

US 2014/0142161 A1 May 22, 2014

Related U.S. Application Data

(60) Provisional application No. 61/477,671, filed on Apr. 21, 2011.

(51) Int. Cl.

| | |
|---|---|
| ***C07H 21/02*** | (2006.01) |
| ***C07H 21/04*** | (2006.01) |
| ***A61K 48/00*** | (2006.01) |
| ***A61K 35/00*** | (2006.01) |
| ***C12N 15/67*** | (2006.01) |
| *C12N 15/11* | (2006.01) |

(52) U.S. Cl.

CPC .............. *A61K 48/005* (2013.01); *C12N 15/67* (2013.01); *C12N 15/111* (2013.01); *C12N 2310/141* (2013.01); *C12N 2310/3519* (2013.01); *C12N 2750/14143* (2013.01)

(58) Field of Classification Search

CPC . C12N 2310/14; C12N 15/111; C12N 15/113

See application file for complete search history.

(56) References Cited

U.S. PATENT DOCUMENTS

| | | | |
|---|---|---|---|
| 5,478,745 A | 12/1995 | Samulski et al. | |
| 5,871,982 A | 2/1999 | Wilson et al. | |
| 6,251,677 B1 | 6/2001 | Wilson et al. | |
| 6,485,966 B2 | 11/2002 | Gao et al. | |
| 7,235,393 B2 | 6/2007 | Gao et al. | |
| 7,427,396 B2 | 9/2008 | Arbetman et al. | |
| 7,456,015 B2 | 11/2008 | Bohn et al. | |
| 7,906,111 B2 | 3/2011 | Wilson et al. | |
| 8,222,221 B2 | 7/2012 | Corey et al. | |
| 8,734,809 B2 | 5/2014 | Gao et al. | |
| 2003/0138772 A1 | 7/2003 | Gao et al. | |
| 2005/0037988 A1 | 2/2005 | Zamore et al. | |
| 2005/0137153 A1 | 6/2005 | McSwiggen et al. | |
| 2006/0063174 A1 | 3/2006 | Turner et al. | |
| 2006/0292117 A1 | 12/2006 | Loiler et al. | |
| 2007/0036760 A1 | 2/2007 | Wilson et al. | |
| 2009/0131355 A1 | 5/2009 | Bot et al. | |
| 2010/0186103 A1 | 7/2010 | Gao et al. | |
| 2010/0323001 A1* | 12/2010 | Pachuk | 424/450 |
| 2011/0172293 A1 | 7/2011 | Fish et al. | |
| 2011/0258716 A1 | 10/2011 | Baltimore et al. | |
| 2012/0137379 A1 | 5/2012 | Gao et al. | |
| 2013/0101558 A1 | 4/2013 | Gao et al. | |
| 2013/0195801 A1 | 8/2013 | Gao et al. | |
| 2013/0281516 A1 | 10/2013 | Gao et al. | |
| 2014/0142161 A1 | 5/2014 | Flotte et al. | |
| 2014/0296486 A1 | 10/2014 | Gao et al. | |
| 2014/0335054 A1 | 11/2014 | Gao et al. | |

FOREIGN PATENT DOCUMENTS

| | | |
|---|---|---|
| WO | WO 2007/000668 A2 | 1/2007 |
| WO | WO 2007/027775 A2 | 3/2007 |
| WO | WO 2008/091703 | 7/2008 |
| WO | WO 2008/147839 A1 | 12/2008 |
| WO | WO 2008/150897 A2 | 12/2008 |
| WO | WO 2009/109665 A1 | 9/2009 |
| WO | WO 2009/146178 A1 | 12/2009 |
| WO | WO 2010/034314 A1 | 4/2010 |
| WO | WO 2010/129021 A1 | 11/2010 |
| WO | WO 2013/190059 A1 | 12/2013 |

OTHER PUBLICATIONS

Afione et al., In vivo model of adeno-associated virus vector persistence and rescue. J Virol. May 1996;70(5):3235-41.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Brantly et al., Phase I trial of intramuscular injection of a recombinant adeno-associated virus serotype 2 alphal-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Büssing et al., let-7 microRNAs in development, stem cells and cancer. Trends Mol Med. Sep. 2008;14(9):400-9. doi: 10.1016/j.molmed.2008.07.001. Epub Jul. 31, 2008.

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.

(Continued)

*Primary Examiner* — Amy Bowman

(74) *Attorney, Agent, or Firm* — Wolf, Greenfield & Sacks, P.C.

(57) ABSTRACT

The invention relates to isolated nucleic acids and rAAV-based compositions, methods and kits useful for treating genetic diseases (e.g., alpha-1 antitrypsin deficiency).

13 Claims, 11 Drawing Sheets

(56) References Cited

OTHER PUBLICATIONS

Chen et al., Efficient transduction of vascular endothelial cells with recombinant adeno-associated virus serotype 1 and 5 vectors. Hum Gene Ther. Feb. 2005;16(2):235-47.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Conlon et al., Efficient hepatic delivery and expression from a recombinant adeno-associated virus 8 pseudotyped alphal-antitrypsin vector. Mol Ther. Nov. 2005;12(5):867-75. Epub Aug. 8, 2005.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Czech, MicroRNAs as therapeutic targets. N Engl J Med. Mar. 16, 2006;354(11):1194-5.
Ebert et al., MicroRNA sponges: competitive inhibitors of small RNAs in mammalian cells. Nat Methods. Sep. 2007;4(9):721-6. Epub Aug. 12, 2007.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Elmen et al., LNA-mediated microRNA silencing in non-human primates. Nature. Apr. 17, 2008;452(7189):896-9. Epub Mar. 26, 2008.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Fisher et al., Transduction with recombinant adeno-associated virus for gene therapy is limited by leading-strand synthesis. J Virol. Jan. 1996;70(1):520-32.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hutvágner et al., Sequence-specific inhibition of small RNA function. PLoS Biol. Apr. 2004;2(4):E98. Epub Feb. 24, 2004.
Johnson et al., RAS is regulated by the let-7 microRNA family. Cell. Mar. 11, 2005;120(5):635-47.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kota et al., Therapeutic microRNA delivery suppresses tumorigenesis in a murine liver cancer model. Cell. Jun. 12, 2009;137(6):1005-17. doi: 10.1016/j.cell1.2009.04.021.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Ex vivo transduction and transplantation of bone marrow cells for liver gene delivery of alphal-antitrypsin. Mol Ther. Aug. 2010;18(8):1553-8. Epub Jun. 15, 2010.
Li et al., Intronic microRNA: discovery and biological implications. DNA Cell Biol. Apr. 2007;26(4):195-207.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Lomas et al., The mechanism of Z alpha 1-antitrypsin accumulation in the liver. Nature. Jun. 18, 1992;357(6379):605-7.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McLean et al., Gene targeted therapeutics for liver disease in alpha-1 antitrypsin deficiency. Biologics. 2009;3:63-75. Epub Jul. 13, 2009.
Meister et al., Sequence-specific inhibition of microRNA- and siRNA-induced RNA silencing. RNA. Mar. 2010;10(3):544-50.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):5391-5392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.

(56) References Cited

OTHER PUBLICATIONS

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., The pros and cons of immunomodulatory IL-10 gene therapy with recombinant AAV in a Cftr-/- -dependent allergy mouse model. Gene Ther. Feb. 2009;16(2):172-83. Epub Sep. 25, 2008.

Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Sen et al., Micromanaging vascular biology: tiny microRNAs play big band. J Vasc Res. 2009;46(6):527-40. doi: 10.1159/000226221. Epub Jun. 30, 2009.

Sivasothy et al., Pathogenic alpha 1-antitrypsin polymers are formed by reactive loop-beta-sheet A linkage. J Biol Chem. Oct. 27, 2000;275(43):33663-8.

Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.

Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.

Vaucheret et al., The action of ARGONAUTE1 in the miRNA pathway and its regulation by the miRNA pathway are crucial for plant development. Genes Dev. May 15, 2004;18(10):1187-97. Epub May 6, 2004.

Vermeulen et al., Double-stranded regions are essential design components of potent inhibitors of RISC function. RNA. May 2007;13(5):723-30. Epub Mar. 30, 2007.

Virella-Lowell et al., Enhancing rAAV vector expression in the lung. J Gene Med. Jul. 2005;7(7):842-50.

Waldman et al., Applications of microRNA in cancer: Exploring the advantages of miRNA. Clin Transl Sci. Jun. 2009;2(3):248-9. doi: 10.1111/j.1752-8062.2009.00110.x.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zabner et al., Adeno-associated virus type 5 (AAVS) but not AAV2 binds to the apical surfaces of airway epithelia and facilitates gene transfer. J Virol. Apr. 2000;74(8):3852-8.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

* cited by examiner

SEQUENCE LISTING

```
<160> NUMBER OF SEQ ID NOS: 32

<210> SEQ ID NO 1
<211> LENGTH: 418
<212> TYPE: PRT
<213> ORGANISM: Homo sapiens
```

-continued

<400> SEQUENCE: 1

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
```

```
                405                 410                 415

Gln Lys


<210> SEQ ID NO 2
<211> LENGTH: 394
<212> TYPE: PRT
<213> ORGANISM: Homo sapiens

<400> SEQUENCE: 2

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
```

```
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390


<210> SEQ ID NO 3
<211> LENGTH: 418
<212> TYPE: PRT
<213> ORGANISM: Homo sapiens

<400> SEQUENCE: 3

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335
```

```
Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Lys Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys


<210> SEQ ID NO 4
<211> LENGTH: 394
<212> TYPE: PRT
<213> ORGANISM: Homo sapiens

<400> SEQUENCE: 4

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285
```

```
Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Lys Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390


<210> SEQ ID NO 5
<211> LENGTH: 1257
<212> TYPE: RNA
<213> ORGANISM: Homo sapiens

<400> SEQUENCE: 5

augccgucuu cugucucgug gggcauccuc cugcuggcag gccugugcug ccugguccu      60

gucucccugg cugaggaucc ccagggagau gcugcccaga agacagauac aucccaccau    120

gaucaggauc acccaaccuu caacaagauc acccccaacc uggcugaguu cgccuucagc    180

cuauaccgcc agcuggcaca ccaguccaac agcaccaaua ucuucuucuc cccagugagc    240

aucgcuacag ccuuugcaau gcucucccug gggaccaagg cugacacuca cgaugaaauc    300

cuggagggcc ugaauuucaa ccucacggag auuccggagg cucagaucca ugaaggcuuc    360

caggaacucc uccguacccu caaccagcca gacagccagc uccagcugac caccggcaau    420

ggccuguucc ucagcgaggg ccugaagcua guggauaagu uuuuggagga uguuaaaaag    480

uuguaccacu cagaagccuu cacugucaac uucggggaca ccgaagaggc caagaaacag    540

aucaacgauu acguggagaa ggguacucaa gggaaaauug uggauuuggu caaggagcuu    600

gacagagaca caguuuuugc ucuggugaau uacaucuucu uuaaaggcaa augggagaga    660

cccuuugaag ucaaggacac cgaggaagag gacuuccacg uggaccaggu gaccaccgug    720

aaggugccua ugaugaagcg uuuaggcaug uuuaacaucc agcacuguaa gaagcugucc    780

agcugggugc ugcugaugaa auaccugggc aaugccaccg ccaucuucuu ccugccugau    840

gaggggaaac uacagcaccu ggaaaaugaa cucacccacg auaucaucac caaguuccug    900

gaaaaugaag acagaagguc ugccagcuua cauuuaccca aacuguccau uacuggaacc    960

uaugaucuga agagcguccu gggucaacug ggcaucacua aggucuucag caauggggcu   1020

gaccucuccg ggucacaga ggaggcaccc cugaagcucu ccaaggccgu gcauaaggcu   1080

gugcugacca ucgacgagaa agggacugaa gcugcugggg ccauguuuuu agaggccaua   1140

cccaugucua ucccccccga ggucaaguuc aacaaacccu uugucuucuu aaugauugaa   1200

caaaauacca agucuccccu cuucauggga aaaguggu ga aucccaccca aaaauaa      1257


<210> SEQ ID NO 6
<211> LENGTH: 3220
<212> TYPE: RNA
<213> ORGANISM: Homo sapiens

<400> SEQUENCE: 6
```

-continued

```
acaaugacuc cuuucgguaa gugcagugga agcuguacac ugcccaggca aagcguccgg     60
gcagcguagg cgggcgacuc agaucccagc caguggacuu agccccuguu ugcuccuccg    120
auaacugggg ugaccuuggu uaauauucac cagcagccuc ccccguugcc ccucuggauc    180
cacugcuuaa auacggacga ggacagggcc cugucuccuc agcuucaggc accaccacug    240
accugggaca gugaaucgac aaugccgucu ucugucucgu ggggcauccu ccugcuggca    300
ggccugugcu gccugguccc ugucuccug gcugaggauc cccagggaga ugcugcccag    360
aagacagaua caucccacca ugaucaggau cacccaaccu ucaacaagau cacccccaac    420
cuggcugagu ucgccuucag ccuauaccgc cagcuggcac accaguccaa cagcaccaau    480
aucuucuucu ccccagugag caucgcuaca gccuuugcaa ugcucucccu ggggaccaag    540
gcugacacuc acgaugaaau ccuggagggc cugaauuuca accucacgga gauuccggag    600
gcucagaucc augaaggcuu ccaggaacuc cuccguaccc ucaaccagcc agacagccag    660
cuccagcuga ccaccggcaa uggccuguuc cucagcgagg gccugaagcu aguggauaag    720
uuuuuggagg auguuaaaaa guuguaccac ucagaagccu ucacugucaa cuucggggac    780
accgaagagg ccaagaaaca gaucaacgau uacguggaga aggguacuca agggaaaauu    840
guggauuugg ucaaggagcu ugacagagac acaguuuuug cucuggugaa uuacaucuuc    900
uuuaaaggca aaugggagag acccuuugaa gucaaggaca ccgaggaaga ggacuuccac    960
guggaccagg ugaccaccgu gaaggugccu augaugaagc guuuaggcau guuuaacauc   1020
cagcacugua agaagcuguc cagcugggug cugcugauga aauaccuggg caaugccacc   1080
gccaucuucu uccugccuga ugaggggaaa cuacagcacc uggaaaauga acucacccac   1140
gauaucauca ccaaguuccu ggaaaaugaa gacagaaggu cugccagcuu acauuuaccc   1200
aaacugucca uuacuggaac cuaugaucug aagagcgucc ugggucaacu gggcaucacu   1260
aaggucuuca gcaauggggc ugaccucucc ggggucacag aggaggcacc ccugaagcuc   1320
uccaaggccg ugcauaaggc ugugcugacc aucgacgaga aagggacuga agcugcuggg   1380
gccauguuuu uagaggccau acccaugucu aucccccccg aggucaaguu caacaaaccc   1440
uuugucuucu uaaugauuga acaaaauacc aagucucccc ucuucauggg aaaaguggug   1500
aaucccaccc aaaaauaacu gccucucgcu ccucaacccc uccccuccau cccuggcccc   1560
cucccuggau gacauuaaag aaggguugag cugguccccug ccugcaugug acuguaaauc  1620
ccucccaugu uuucucugag ucucccuuug ccugcugagg cuguaugugg gcuccaggua   1680
acagugcugu cuucgggccc ccugaacugu guucauggag caucuggcug gguaggcaca   1740
ugcugggcuu gaauccaggg gggacugaau ccucagcuua cggaccuggg cccaucuguu   1800
ucuggagggc uccagucuuc cuuguccugu cuuggagucc ccaagaagga aucacagggg   1860
aggaaccaga uaccagccau gaccccaggc uccaccaagc aucuucaugu cccccugcuc   1920
aucccccacu ccccccacc cagaguugcu cauccugcca gggcuggcug ugcccacccc   1980
aaggcugccc uccugggggc cccagaacug ccugaucgug ccguggccca guuuuguggc   2040
aucugcagca acacaagaga gaggacaaug uccuccucuu gacccgcugu caccuaacca   2100
gacucgggcc cugcaccucu caggcacuuc uggaaaauga cugaggcaga uucuuccuga   2160
agcccauucu ccaugggca acaaggacac cuauucuguc cuuguccuuc caucgcugcc   2220
ccagaaagcc ucacauaucu ccguuuagaa ucaggucccu ucuccccaga ugaagaggag   2280
ggucucugcu uuguuuucuc uaucuccucc ucagacuuga ccaggcccag caggccccag   2340
aagaccauua cccuauaucc cuucuccucc cuagucacau ggccauaggc cugcugaugg   2400
```

```
cucaggaagg ccauugcaag gacuccucag cuaugggaga ggaagcacau cacccauuga   2460

cccccgcaac cccucccuuu ccuccucuga gucccgacug gggccacaug cagccugacu   2520

ucuuugugcc uguugcuguc ccugcagucu ucagagggcc accgcagcuc cagugccacg   2580

gcaggaggcu guuccugaau agccccugug guaagggcca ggagaguccu uccauccucc   2640

aaggcccugc uaaaggacac agcagccagg aaguccccug ggccccuagc ugaaggacag   2700

ccugcucccu ccgucucuac caggaauggc cuuguccuau ggaaggcacu gccccauccc   2760

aaacuaaucu aggaaucacu gucuaaccac ucacugucau gaauguguac uuaaaggaug   2820

agguugaguc auaccaaaua gugauuucga uaguucaaaa uggugaaauu agcaauucua   2880

caugauucag ucuaaucaau ggauaccgac uguuucccac acaagucucc uguucucuua   2940

agcuuacuca cugacagccu uucacucucc acaaauacau uaaagauaug gccaucacca   3000

agcccccuag gaugacacca gaccugagag ucugaagacc uggauccaag uucugacuuu   3060

ucccccugac agcuguguga ccuucgugaa gucgccaaac cucucugagc cccagucauu   3120

gcuaguaaga ccugccuuug aguugguaug auguucaagu uagauaacaa aauguuuaua   3180

cccauuagaa cagagaauaa auagaacuac auuucuugca                         3220
```

```
<210> SEQ ID NO 7
<211> LENGTH: 3513
<212> TYPE: RNA
<213> ORGANISM: Homo sapiens

<400> SEQUENCE: 7

ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaagggcg    240

gcaguaaguc uucagcauca ggcauuuugg ggugacucag uaaaugguag aucuugcuac    300

caguggaaca gccacuaagg auucugcagu gagagcagag ggccagcuaa gugguacucu    360

cccagagacu gucugacuca cgccaccccc uccaccuugg acacaggacg cugugguuuc    420

ugagccaggu acaaugacuc cuuucgcagc cuccccguu gccccucugg auccacugcu    480

uaaauacgga cgaggacagg gcccugucuc cucagcuuca ggcaccacca cugaccuggg    540

acagugaauc gacaaugccg ucuucugucu cguggggcau ccuccugcug gcaggccugu    600

gcugccuggu cccugucucc cuggcugagg auccccaggg agaugcugcc cagaagacag    660

auacauccca ccaugaucag gaucacccaa ccuucaacaa gaucaccccc aaccuggcug    720

aguucgccuu cagccuauac cgccagcugg cacaccaguc caacagcacc aauaucuucu    780

ucuccccagu gagcaucgcu acagccuuug caaugcucuc ccuggggacc aaggcugaca    840

cucacgauga aauccuggag ggccugaauu ucaaccucac ggagauuccg gaggcucaga    900

uccaugaagg cuuccaggaa cuccuccgua cccucaacca gccagacagc cagcuccagc    960

ugaccaccgg caauggccug uuccucagcg agggccugaa gcuaguggau aaguuuuugg   1020

aggauguuaa aaaguuguac cacucagaag ccuucacugu caacuucggg gacaccgaag   1080

aggccaagaa acagaucaac gauuacgugg agaaggguac ucaagggaaa auuguggauu   1140

uggucaagga gcuugacaga gacacaguuu uugcucuggu gaauuacauc uucuuuaaag   1200

gcaaauggga gagacccuuu gaagucaagg acaccgagga agaggacuuc cacguggacc   1260
```

```
aggugaccac cgugaaggug ccuaugauga agcguuuagg cauguuuaac auccagcacu   1320
guaagaagcu guccagcugg gugcugcuga ugaaauaccu gggcaaugcc accgccaucu   1380
ucuuccugcc ugaugagggg aaacuacagc accuggaaaa ugaacucacc cacgauauca   1440
ucaccaaguu ccuggaaaau gaagacagaa ggucugccag cuuacauuua cccaaacugu   1500
ccauuacugg aaccuaugau cugaagagcg uccuggguca acugggcauc acuaaggucu   1560
ucagcaaugg ggcugaccuc uccgggguca cagaggaggc accccugaag cucuccaagg   1620
ccgugcauaa ggcugugcug accaucgacg agaaagggac ugaagcugcu ggggccaugu   1680
uuuuagaggc cauacccaug ucuauccccc ccgaggucaa guucaacaaa cccuuugucu   1740
ucuuaaugau ugaacaaaau accaagucuc cccucuucau gggaaaagug gugaauccca   1800
cccaaaaaua acugccucuc gcuccucaac cccucccc
uc caucccuggc ccccucccug   1860
gaugacauua aagaaggguu gagcugcucc cugccugcau gugacuguaa aucccuccca   1920
uguuuucucu gagucucccu uugccugcug aggcuguaug ugggcuccag guaacagugc   1980
ugucuucggg cccccugaac uguguucaug gagcaucugg cugguaggc acaugcuggg   2040
cuugaaucca gggggacug aauccucagc uuacggaccu gggcccaucu guuucuggag   2100
ggcuccaguc uuccuugucc ugucuuggag uccccaagaa ggaaucacag gggaggaacc   2160
agauaccagc caugacccca ggcuccacca agcaucuuca uguccccug cucauccccc   2220
acuccccccc acccagaguu gcucauccug ccagggcugg cugugcccac cccaaggcug   2280
cccuccuggg ggccccagaa cugccugauc gugccguggc ccaguuugu ggcaucugca   2340
gcaacacaag agagaggaca auguccuccu cuugacccgc ugucaccuaa ccagacucgg   2400
gcccugcacc ucucaggcac uucuggaaaa ugacugaggc agauucuucc ugaagcccau   2460
ucuccauggg gcaacaagga caccuauucu guccuugucc uuccaucgcu gccccagaaa   2520
gccucacaua ucuccguuua gaaucagguc ccuucucccc agaugaagag gagggucucu   2580
gcuuuguuuu cucuaucucc uccucagacu ugaccaggcc cagcaggccc cagaagacca   2640
uuacccuaua ucccuucucc ucccuaguca cauggccaua ggccugcuga uggcucagga   2700
aggccauugc aaggacuccu cagcuauggg agaggaagca caucacccau ugacccccgc   2760
aaccccuccc uuuccuccuc ugagucccga cuggggccac augcagccug acuucuuugu   2820
gccuguugcu gucccugcag ucuucagagg gccaccgcag cuccagugcc acggcaggag   2880
gcuguuccug aauagccccu gugguaaggg ccaggagagu ccuuccaucc uccaaggccc   2940
ugcuaaagga cacagcagcc aggaaguccc cugggcccu agcugaagga cagccugcuc   3000
ccuccgucuc uaccaggaau ggccuugucc uauggaaggc acugccccau cccaaacuaa   3060
ucuaggaauc acugucuaac cacucacugu caugaaugug uacuuaaagg augagguuga   3120
gucauaccaa auagugauuu cgauaguuca aaauggugaa auuagcaauu cuacaugauu   3180
cagucuaauc aauggauacc gacuguuucc cacacaaguc uccuguucuc uuaagcuuac   3240
ucacugacag ccuuucacuc uccacaaaua cauuaaagau auggccauca ccaagccccc   3300
uaggaugaca ccagaccuga gagucugaag accuggaucc aaguucugac uuuuccccu   3360
gacagcugug ugaccuucgu gaagucgcca aaccucucug agccccaguc auugcuagua   3420
agaccugccu uugaguuggu augauguuca aguuagauaa caaaauguuu auacccauua   3480
gaacagagaa uaaauagaac uacauuucuu gca                                3513
```

<210> SEQ ID NO 8
<211> LENGTH: 3236

<212> TYPE: RNA
<213> ORGANISM: Homo sapiens

<400> SEQUENCE: 8

```
ugggcaggaa cugggcacug ugcccagggc augcacugcc uccacgcagc aacccucaga     60
guccugagcu gaaccaagaa ggaggagggg gucgggccuc cgaggaaggc cuagccgcug    120
cugcugccag gaauuccagg uuggaggggc ggcaaccucc ugccagccuu caggccacuc    180
uccugugccu gccagaagag acagagcuug aggagagcuu gaggagagca ggaaaggugg    240
gacauugcug cugcugcuca cucaguucca caggacaaug ccgucuucug ucucgugggg    300
cauccuccug cuggcaggcc ugugcugccu gguccccugu cucccuggcug aggaucccca    360
gggagaugcu gcccagaaga cagauacauc ccaccaugau caggaucacc caaccuucaa    420
caagaucacc cccaaccugg cugaguucgc cuucagccua uaccgccagc uggcacacca    480
guccaacagc accaauaucu ucuucucccc agugagcauc gcuacagccu uugcaaugcu    540
cucccugggg accaaggcug acacucacga ugaaauccug gagggccuga auuucaaccu    600
cacggagauu ccggaggcuc agauccauga aggcuuccag gaacuccucc guacccucaa    660
ccagccagac agccagcucc agcugaccac cggcaauggc cuguuccuca gcgagggccu    720
gaagcuagug gauaaguuuu uggaggaugu uaaaaaguug uaccacucag aagccuucac    780
ugucaacuuc ggggacaccg aagaggccaa gaaacagauc aacgauuacg uggagaaggg    840
uacucaaggg aaaauugugg auuuggucaa ggagcuugac agagacacag uuuuugcucu    900
ggugaauuac aucuucuuua aaggcaaaug ggagagaccc uuugaaguca aggacaccga    960
ggaagaggac uuccacgugg accaggugac caccgugaag gugccuauga ugaagcguuu   1020
aggcauguuu aacauccagc acuguaagaa gcuguccagc ugggugcugc ugaugaaaua   1080
ccugggcaau gccaccgcca ucuucuuccu gccugaugag gggaaacuac agcaccugga   1140
aaaugaacuc acccacgaua ucaucaccaa guuccuggaa aaugaagaca gaaggucugc   1200
cagcuuacau uuacccaaac uguccauuac uggaaccuau gaucugaaga gcguccuggg   1260
ucaacugggc aucacuaagg ucuucagcaa uggggcugac cucuccgggg ucacagagga   1320
ggcacccug aagcucucca aggccgugca uaaggcugug cugaccaucg acgagaaagg   1380
gacugaagcu gcuggggcca uguuuuuaga ggccauaccc augucuaucc cccccgaggu   1440
caaguucaac aaacccuuug ucuucuuaau gauugaacaa aauaccaagu cucccccucuu   1500
caugggaaaa guggugaauc ccacccaaaa auaacugccu cucgcuccuc aaccccuccc   1560
cuccaucccu ggccccccucc cuggaugaca uuaaagaagg guugagcugg ucccugccug   1620
caugugacug uaaaucccuc ccauguuuuc ucugagucuc ccuuugccug cugaggcugu   1680
augugggcuc cagguaacag ugcugucuuc gggcccccug aacuguguuc auggagcauc   1740
uggcugggua ggcacaugcu gggcuugaau ccagggggga cugaauccuc agcuuacgga   1800
ccugggccca ucuguuucug gagggcucca gucuuccuug uccugucuug gaguccccaa   1860
gaaggaauca caggggagga accagauacc agccaugacc ccaggcucca ccaagcaucu   1920
ucaugucccc cugcucaucc cccacucccc cccacccaga guugcucauc cugccagggc   1980
uggcugugcc caccccaagg cugcccuccu gggggcccca gaacugccug aucgugccgu   2040
ggcccaguuu uguggcaucu gcagcaacac aagagagagg acaaugucuu ccucuugacc   2100
cgcugucacc uaaccagacu cgggcccugc accucucagg cacuucugga aaaugacuga   2160
ggcagauucu uccugaagcc cauucuccau ggggcaacaa ggacaccuau ucuguccuug   2220
```

uccuuccauc gcugccccag aaagccucac auaucuccgu uuagaaucag gucccuucuc 2280
cccagaugaa gaggagggguc ucugcuuugu uuucucuauc uccuccucag acuugaccag 2340
gcccagcagg ccccagaaga ccauuacccu auaucccuuc ucccucccuag ucacauggcc 2400 auaggccugc ugauggcuca ggaaggccau ugcaaggacu ccucagcuau gggagaggaa 2460
gcacaucacc cauugacccc cgcaaccccu cccuuuccuc cucugagucc cgacuggggc 2520
cacaugcagc cugacuucuu ugugccuguu gcuguccccug cagucuucag agggccaccg 2580
cagcuccagu gccacggcag gaggcuguuc cugaauagcc ccugugguaa gggccaggag 2640
aguccuucca uccuccaagg cccugcuaaa ggacacagca gccaggaagu ccccugggcc 2700
ccuagcugaa ggacagccug cuccccuccgu cucuaccagg aauggccuug uccuauggaa 2760
ggcacugccc caucccaaac uaaucuagga aucacugucu aaccacucac ugucaugaau 2820
guguacuuaa aggaugaggu ugagucauac caaauaguga uuucgauagu ucaaaauggu 2880
gaaauuagca auucuacaug auucagucua aucaauggau accgacuguu ucccacacaa 2940
gucuccuguu cucuuaagcu uacucacuga cagccuuuca cucuccacaa auacauuaaa 3000
gauauggcca ucaccaagcc cccuaggaug acaccagacc ugagagucug aagaccugga 3060
uccaaguucu gacuuuuccc ccugacagcu gugugaccuu cgugaagucg ccaaaccucu 3120
cugagcccca gucauugcua guaagaccug ccuuugaguu gguaugaugu ucaaguuaga 3180
uaacaaaaug uuuauaccca uuagaacaga gaauaaauag aacuacauuu cuugca 3236

<210> SEQ ID NO 9
<211> LENGTH: 3532
<212> TYPE: RNA
<213> ORGANISM: Homo sapiens

<400> SEQUENCE: 9
ugggcaggaa cugggcacug ugcccagggc augcacugcc uccacgcagc aacccucaga 60
guccugagcu gaaccaagaa ggaggagggg gucgggccuc cgaggaaggc cuagccgcug 120
cugcugccag gaauuccagg uuggaggggc ggcaaccucc ugccagccuu caggccacuc 180
uccugugccu gccagaagag acagagcuug aggagagcuu gaggagagca ggaaaggugg 240
gacauugcug cugcugcuca cucaguucca cagggcggca guaagucuuc agcaucaggc 300
auuuuggggu gacucaguaa augguagauc uugcuaccag uggaacagcc acuaaggauu 360
cugcagugag agcagagggc cagcuaagug guacucuccc agagacuguc ugacucacgc 420
cacccccucc accuuggaca caggacgcug ugguuucuga gccagcagcc ucccccguug 480
ccccucugga uccacugcuu aaauacggac gaggacaggg cccugucucc ucagcuucag 540
gcaccaccac ugaccuggga cagugaaucg acaaugccgu cuucugucuc guggggcauc 600
cuccugcugg caggccugug cugccugguc ccugucuccc uggcugagga uccccaggga 660
gaugcugccc agaagacaga uacaucccac caugaucagg aucacccaac cuucaacaag 720
aucaccccca accuggcuga guucgccuuc agccuauacc gccagcuggc acaccagucc 780
aacagcacca auaucuucuu cuccccagug agcaucgcua cagccuuugc aaugcucucc 840
cuggggacca aggcugacac ucacgaugaa auccuggagg gccugaauuu caaccucacg 900
gagauuccgg aggcucagau ccaugaaggc uuccaggaac uccuccguac ccucaaccag 960
ccagacagcc agcuccagcu gaccaccggc aauggccugu uccucagcga gggccugaag 1020
cuaguggaua aguuuuugga ggauguuaaa aaguuguacc acucagaagc cuucacuguc 1080
aacuucgggg acaccgaaga ggccaagaaa cagaucaacg auuacgugga gaaggguacu 1140

```
caagggaaaa uuguggauuu ggucaaggag cuugacagag acacaguuuu ugcucuggug   1200

aauuacaucu ucuuuaaagg caaaugggag agacccuuug aagucaagga caccgaggaa   1260

gaggacuucc acguggacca ggugaccacc gugaaggugc cuaugaugaa gcguuuaggc   1320

auguuuaaca uccagcacug uaagaagcug uccagcuggg ugcugcugau gaaauaccug   1380

ggcaaugcca ccgccaucuu cuuccugccu gaugagggga aacuacagca ccuggaaaau   1440

gaacucaccc acgauaucau caccaaguuc cuggaaaaug aagacagaag gucugccagc   1500

uuacauuuac ccaaacuguc cauuacugga accuaugauc ugaagagcgu ccugggucaa   1560

cugggcauca cuaaggucuu cagcaauggg gcugaccucu ccgggcucac agaggaggca   1620

ccccugaagc ucuccaaggc cgugcauaag gcugugcuga ccaucgacga gaaagggacu   1680

gaagcugcug gggccauguu uuuagaggcc auacccaugu cuaucccccc cgaggucaag   1740

uucaacaaac ccuuugucuu cuuaaugauu gaacaaaaua ccaagucucc ccucuucaug   1800

ggaaaagugg ugaaucccac ccaaaaauaa cugccucucg cuccucaacc ccucccccucc   1860

aucccuggcc cccucccugg augacauuaa agaaggguug agcugguccc ugccugcaug   1920

ugacuguaaa ucccucccau guuuucucug agucucccuu ugccugcuga ggcuguaugu   1980

gggcuccagg uaacagugcu gucuucgggc cccccugaacu guguucaugg agcaucuggc   2040

uggguaggca caugcugggc uugaauccag gggggacuga auccucagcu uacggaccug   2100

ggcccaucug uuucuggagg gcuccagucu uccuuguccu gucuuggagu ccccaagaag   2160

gaaucacagg ggaggaacca gauaccagcc augaccccag gcuccaccaa gcaucuucau   2220

guccccccugc ucaucccccca cucccccccca cccagaguug cucauccugc cagggcuggc   2280

ugugcccacc ccaaggcugc ccuccugggg gccccagaac ugccugaucg ugccguggcc   2340

caguuuugug gcaucugcag caacacaaga gagaggacaa uguccuccuc uugacccgcu   2400

gucaccuaac cagacucggg cccugcaccu cucaggcacu ucuggaaaau gacugaggca   2460

gauucuuccu gaagcccauu cuccaugggg caacaaggac accuauucug uccuuguccu   2520

uccaucgcug ccccagaaag ccucacauau cuccguuuag aaucaggucc cuucucccca   2580

gaugaagagg agggucucug cuuuguuuuc ucuaucuccu ccucagacuu gaccaggccc   2640

agcaggcccc agaagaccau uacccuauau cccuucuccu cccuagucac auggccauag   2700

gccugcugau ggcucaggaa ggccauugca aggacuccuc agcuauggga gaggaagcac   2760

aucacccauu gacccccgca accccucccu uuccuccucu gagucccgac uggggccaca   2820

ugcagccuga cuucuuugug ccuguugcug ucccugcagu cuucagaggg ccaccgcagc   2880

uccagugcca cggcaggagg cuguuccuga auagccccug ugguaagggc caggagaguc   2940

cuuccauccu ccaaggcccu gcuaaaggac acagcagcca ggaagucccc ugggccccua   3000

gcugaaggac agccugcucc cuccgucucu accaggaaug gccuuguccu auggaaggca   3060

cugccccauc ccaaacuaau cuaggaauca cugucuaacc acucacuguc augaaugugu   3120

acuuaaagga ugagguugag ucauaccaaa uagugauuuc gauaguucaa aauggugaaa   3180

uuagcaauuc uacaugauuc agucuaauca auggauaccg acuguuuccc acacaagucu   3240

ccuguucucu uaagcuuacu cacugacagc cuuucacucu ccacaaauac auuaaagaua   3300

uggccaucac caagcccccu aggaugacac cagaccugag agucugaaga ccuggaucca   3360

aguucugacu uuucccccug acagcugugu gaccuucgug aagucgccaa accucucuga   3420

gccccaguca uugcuaguaa gaccugccuu ugaguuggua ugauguucaa guuagauaac   3480
```

```
aaaauguuua uacccauuag aacagagaau aaauagaacu acauuucuug ca          3532


<210> SEQ ID NO 10
<211> LENGTH: 3340
<212> TYPE: RNA
<213> ORGANISM: Homo sapiens

<400> SEQUENCE: 10

ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaaggugg    240

gacauugcug cugcugcuca cucaguucca cagcagccuc ccccguugcc ccucuggauc    300

cacugcuuaa auacggacga ggacagggcc cugucuccuc agcuucaggc accaccacug    360

accugggaca gugaaucgac aaugccgucu ucugucucgu ggggcauccu ccugcuggca    420

ggccugugcu gccugguccc ugucucccug gcugaggauc cccagggaga ugcugcccag    480

aagacagaua caucccacca ugaucaggau cacccaaccu ucaacaagau cacccccaac    540

cuggcugagu ucgccuucag ccuauaccgc cagcuggcac accaguccaa cagcaccaau    600

aucuucuucu ccccagugag caucgcuaca gccuuugcaa ugcucucccu ggggaccaag    660

gcugacacuc acgaugaaau ccuggagggc cugaauuuca accucacgga gauuccggag    720

gcucagaucc augaaggcuu ccaggaacuc cuccguaccc ucaaccagcc agacagccag    780

cuccagcuga ccaccggcaa uggccuguuc cucagcgagg gccugaagcu aguggauaag    840

uuuuuggagg auguuaaaaa guuguaccac ucagaagccu ucacugucaa cuucggggac    900

accgaagagg ccaagaaaca gaucaacgau uacguggaga aggguacuca agggaaaauu    960

guggauuugg ucaaggagcu ugacagagac acaguuuuug cucuggugaa uuacaucuuc   1020

uuuaaaggca aaugggagag acccuuugaa gucaaggaca ccgaggaaga ggacuuccac   1080

guggaccagg ugaccaccgu gaaggugccu augaugaagc guuuaggcau guuuaacauc   1140

cagcacugua agaagcuguc cagcugggug cugcugauga aauaccuggg caaugccacc   1200

gccaucuucu uccugccuga ugaggggaaa cuacagcacc uggaaaauga acucacccac   1260

gauaucauca ccaaguuccu ggaaaaugaa gacagaaggu cugccagcuu acauuuaccc   1320

aaacugucca uuacuggaac cuaugaucug aagagcgucc ugggucaacu gggcaucacu   1380

aaggucuuca gcaauggggc ugaccucucc ggggucacag aggaggcacc ccugaagcuc   1440

uccaaggccg ugcauaaggc ugugcugacc aucgacgaga aagggacuga agcugcuggg   1500

gccauguuuu uagaggccau acccaugucu aucccccccg aggucaaguu caacaaaccc   1560

uuugucuucu uaaugauuga acaaaauacc aagucucccc ucuucauggg aaaaguggug   1620

aaucccaccc aaaaauaacu gccucucgcu ccucaacccc uccccuccau cccuggcccc   1680

cucccuggau gacauuaaag aaggguugag cugguccccug ccugcaugug acuguaaauc   1740

ccucccaugu uuucucugag ucucccuuug ccugcugagg cuguaugugg gcuccaggua   1800

acagugcugu cuucgggccc ccugaacugu guucauggag caucuggcug gguaggcaca   1860

ugcugggcuu gaauccaggg gggacugaau ccucagcuua cggaccuggg cccaucuguu   1920

ucuggagggc uccagucuuc cuuguccugu cuuggagucc ccaagaagga aucacagggg   1980

aggaaccaga uaccagccau gaccccaggc uccaccaagc aucuucaugu cccccugcuc   2040

aucccccacu ccccccacc cagaguugcu cauccugcca gggcuggcug ugcccacccc   2100
```

```
aaggcugccc uccugggggc cccagaacug ccugaucgug ccguggccca guuuuguggc   2160

aucugcagca acacaagaga gaggacaaug uccucccucuu gacccgcugu caccuaacca   2220

gacucgggcc cugcaccucu caggcacuuc uggaaaauga cugaggcaga uucuuccuga   2280

agcccauucu ccauggggca acaaggacac cuauucuguc cuuguccuuc caucgcugcc   2340

ccagaaagcc ucacauaucu ccguuuagaa ucaggucccu ucuccccaga ugaagaggag   2400

ggucucugcu uuguuuucuc uaucucccucc ucagacuuga ccaggcccag caggccccag   2460

aagaccauua cccuauaucc cuucuccucc cuagucacau ggccauaggc cugcugaugg   2520

cucaggaagg ccauugcaag gacuccucag cuaugggaga ggaagcacau cacccauuga   2580

cccccgcaac cccucccuuu ccuccucuga gucccgacug ggccacaug cagccugacu   2640

ucuuugugcc uguugcuguc ccugcagucu ucagagggcc accgcagcuc cagugccacg   2700

gcaggaggcu guuccugaau agccccugug guaagggcca ggagaguccu uccauccucc   2760

aaggcccugc uaaaggacac agcagccagg aaguccccug ggccccuagc ugaaggacag   2820

ccugcucccu ccgucucuac caggaauggc cuuguccuau ggaaggcacu gccccauccc   2880

aaacuaaucu aggaaucacu gucuaaccac ucacugucau gaauguguac uuaaaggaug   2940

agguugaguc auaccaaaua gugauuucga uaguucaaaa uggugaaauu agcaauucua   3000

caugauucag ucuaaucaau ggauaccgac uguuucccac acaagucucc uguucucuua   3060

agcuuacuca cugacagccu uucacucucc acaaauacau uaaagauaug gccaucacca   3120

agcccccuag gaugacacca gaccugagag ucugaagacc uggauccaag uucugacuuu   3180

ucccccugac agcuguguga ccuucgugaa gucgccaaac cucucugagc cccagucauu   3240

gcuaguaaga ccugccuuug aguugguaug auguucaagu uagauaacaa aauguuuaua   3300

cccauuagaa cagagaauaa auagaacuac auuucuugca                         3340
```

<210> SEQ ID NO 11
<211> LENGTH: 3495
<212> TYPE: RNA
<213> ORGANISM: Homo sapiens

<400> SEQUENCE: 11

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaagggcg    240

gcaguaaguc uucagcauca ggcauuuugg ggugacucag uaaaugguag aucuugcuac    300

caguggaaca gccacuaagg auucugcagu gagagcagag ggccagcuaa gugguacucu    360

cccagagacu gucugacuca cgccaccccc uccaccuugg acacaggacg cugugguuuc    420

ugagccagca gccucccccg uugccccucu ggauccacug cuuaaauacg gacgaggaca    480

gggcccuguc ucccucagcuu caggcaccac cacugaccug ggacagugaa ucgacaaugc    540

cgucuucugu cucguggggc auccuccugc uggcaggccu gugcugccug gucccugucu    600

cccuggcuga ggaucccccag ggagaugcug cccagaagac agauacaucc caccaugauc    660

aggaucaccc aaccuucaac aagaucaccc ccaaccuggc ugaguucgcc uucagccuau    720

accgccagcu ggcacaccag uccaacagca ccaauaucuu cuucuccccca gugagcaucg    780

cuacagccuu ugcaaugcuc ucccugggga ccaaggcuga cacucacgau gaaauccugg    840
```

```
agggccugaa uuucaaccuc acggagauuc cggaggcuca gauccaugaa ggcuuccagg    900
aacuccuccg uacccucaac cagccagaca gccagcucca gcugaccacc ggcaauggcc    960
uguuccucag cgagggccug aagcuagugg auaaguuuuu ggaggauguu aaaaaguugu   1020
accacucaga agccuucacu gucaacuucg gggacaccga agaggccaag aaacagauca   1080
acgauuacgu ggagaagggu acucaaggga aaauugugga uuuggucaag gagcuugaca   1140
gagacacagu uuuugcucug gugaauuaca ucuucuuuaa aggcaaaugg gagagacccu   1200
uugaagucaa ggacaccgag gaagaggacu uccacgugga ccaggugacc accgugaagg   1260
ugccuaugau gaagcguuua ggcauguuua acauccagca cuguaagaag cuguccagcu   1320
gggugcugcu gaugaaauac cugggcaaug ccaccgccau cuucuuccug ccugaugagg   1380
ggaaacuaca gcaccuggaa aaugaacuca cccacgauau caucaccaag uuccuggaaa   1440
augaagacag aaggucugcc agcuuacauu uacccaaacu guccauuacu ggaaccuaug   1500
aucugaagag cguccugggu caacugggca ucacuaaggu cuucagcaau ggggcugacc   1560
ucuccggggu cacagaggag gcaccccuga agcucuccaa ggccgugcau aaggcugugc   1620
ugaccaucga cgagaaaggg acugaagcug cuggggccau guuuuuagag gccauaccca   1680
ugucuauccc ccccgagguc aaguucaaca aacccuuugu cuucuuaaug auugaacaaa   1740
auaccaaguc uccccucuuc augggaaaag uggugaaucc cacccaaaaa uaacugccuc   1800
ucgcuccuca accccucccc uccaucccug gcccccuccc uggaugacau uaaagaaggg   1860
uugagcuggu cccugccugc augugacugu aaaucccucc cauguuuucu cugagucucc   1920
cuuugccugc ugaggcugua ugugggcucc agguaacagu gcugucuucg ggccccccuga   1980
acuguguuca uggagcaucu ggcuggguag gcacaugcug ggcuugaauc caggggggac   2040
ugaauccuca gcuuacggac cugggcccau cuguuucugg agggcuccag ucuuccuugu   2100
ccugucuugg aguccccaag aaggaaucac aggggaggaa ccagauacca gccaugaccc   2160
caggcuccac caagcaucuu caugucccc ugcucauccc ccacuccccc ccacccagag   2220
uugcucaucc ugccagggcu ggcugugccc accccaaggc ugcccuccug gggcccccag   2280
aacugccuga ucgugccgug gcccaguuuu guggcaucug cagcaacaca agagagagga   2340
caauguccuc cucuugaccc gcugucaccu aaccagacuc gggcccugca ccucucaggc   2400
acuucuggaa aaugacugag gcagauucuu ccugaagccc auucuccaug gggcaacaag   2460
gacaccuauu cuguccuugu ccuuccaucg cugccccaga aagccucaca uaucuccguu   2520
uagaaucagg ucccuucucc ccagaugaag aggagggucu cugcuuuguu uucucuaucu   2580
ccuccucaga cuugaccagg cccagcaggc cccagaagac cauuacccua uaucccuucu   2640
ccucccuagu cacauggcca uaggccugcu gauggcucag gaaggccauu gcaaggacuc   2700
cucagcuaug ggagaggaag cacaucaccc auugaccccc gcaaccccuc ccuuuccucc   2760
ucugaguccc gacuggggcc acaugcagcc ugacuucuuu gugccuguug cugucccugc   2820
agucuucaga gggccaccgc agcuccagug ccacggcagg aggcuguucc ugaauagccc   2880
cugugguaag ggccaggaga guccuuccau ccuccaaggc ccugcuaaag gacacagcag   2940
ccaggaaguc cccugggccc cuagcugaag gacagccugc ucccuccguc ucuaccagga   3000
auggccuugu ccuauggaag gcacugcccc aucccaaacu aaucuaggaa ucacugucua   3060
accacucacu gucaugaaug uguacuuaaa ggaugagguu gagucauacc aaauagugau   3120
uucgauaguu caaaauggug aaauuagcaa uucuacauga uucagucuaa ucaauggaua   3180
ccgacuguuu cccacacaag ucuccuguuc ucuuaagcuu acucacugac agccuuucac   3240
```

```
ucuccacaaa uacauuaaag auauggccau caccaagccc ccuaggauga caccagaccu   3300

gagagucuga agaccuggau ccaaguucug acuuuucccc cugacagcug ugugaccuuc   3360

gugaagucgc caaaccucuc ugagccccag ucauugcuag uaagaccugc cuuugaguug   3420

guaugauguu caaguuagau aacaaaaugu uuauacccau uagaacagag aauaaauaga   3480

acuacauuuc uugca                                                    3495
```

<210> SEQ ID NO 12
<211> LENGTH: 3492
<212> TYPE: RNA
<213> ORGANISM: Homo sapiens

<400> SEQUENCE: 12

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaagggcg    240

gcaguaaguc uucagcauca ggcauuuugg ggugacucag uaaaugguag aucuugcuac    300

caguggaaca gccacuaagg auucugcagu gagagcagag ggccagcuaa gugguacucu    360

cccagagacu gucugacuca cgccaccccc uccaccuugg acacaggacg cugugguuuc    420

ugagccagcc uccccguug ccccucugga uccacugcuu aaauacggac gaggacaggg    480

cccugucucc ucagcuucag gcaccaccac ugaccuggga cagugaaucg acaaugccgu    540

cuucugucuc guggggcauc cuccugcugg caggccugug cugccugguc ccugucuccc    600

uggcugagga uccccaggga gaugcugccc agaagacaga uacaucccac caugaucagg    660

aucacccaac cuucaacaag aucacccca accuggcuga guucgccuuc agccuauacc    720

gccagcuggc acaccagucc aacagcacca auaucuucuu cuccccagug agcaucgcua    780

cagccuuugc aaugcucucc cuggggacca aggcugacac ucacgaugaa auccuggagg    840

gccugaauuu caaccucacg gagauuccgg aggcucagau ccaugaaggc uuccaggaac    900

uccuccguac ccucaaccag ccagacagcc agcuccagcu gaccaccggc aauggccugu    960

uccucagcga gggccugaag cuaguggaua aguuuuugga ggauguuaaa aaguuguacc   1020

acucagaagc cuucacuguc aacuucgggg acaccgaaga ggccaagaaa cagaucaacg   1080

auuacgugga gaaggguacu caagggaaaa uuguggauuu ggucaaggag cuugacagag   1140

acacaguuuu ugcucuggug aauuacaucu ucuuuaaagg caaaugggag agacccuuug   1200

aagucaagga caccgaggaa gaggacuucc acguggacca ggugaccacc gugaaggugc   1260

cuaugaugaa gcguuuaggc auguuuaaca uccagcacug uaagaagcug uccagcuggg   1320

ugcugcugau gaaauaccug ggcaaugcca ccgccaucuu cuuccugccu gaugagggga   1380

aacuacagca ccuggaaaau gaacucaccc acgauaucau caccaaguuc cuggaaaaug   1440

aagacagaag gucugccagc uuacauuuac ccaaacuguc cauuacugga accuaugauc   1500

ugaagagcgu ccugggucaa cugggcauca cuaaggucuu cagcaauggg gcugaccucu   1560

ccggggucac agaggaggca ccccugaagc ucuccaaggc cgugcauaag gcugugcuga   1620

ccaucgacga gaaagggacu gaagcugcug gggccauguu uuuagaggcc auacccaugu   1680

cuaucccccc cgaggucaag uucaacaaac ccuuugucuu cuuaaugauu gaacaaaaua   1740

ccaagucucc ccucuucaug ggaaaagugg ugaaucccac ccaaaaauaa cugccucucg   1800
```

```
cuccucaacc ccucccccucc aucccuggcc cccucccugg augacauuaa agaaggguug   1860

agcugguccc ugccugcaug ugacuguaaa ucccucccau guuucucug agucucccuu   1920

ugccugcuga ggcuguaugu gggcuccagg uaacagugcu gucuucgggc ccccugaacu   1980

guguucaugg agcaucuggc uggguaggca caugcugggc uugaauccag gggggacuga   2040

auccucagcu uacggaccug ggcccaucug uuucuggagg gcuccagucu uccuuguccu   2100

gucuuggagu ccccaagaag gaaucacagg ggaggaacca gauaccagcc augaccccag   2160

gcuccaccaa gcaucuucau gucccccugc ucaucccccca cucccccccca cccagaguug   2220

cucauccugc cagggcuggc ugugcccacc ccaaggcugc ccuccugggg gccccagaac   2280

ugccugaucg ugccguggcc caguuuugug gcaucugcag caacacaaga gagaggacaa   2340

uguccuccuc uugacccgcu gucaccuaac cagacucggg cccugcaccu cucaggcacu   2400

ucuggaaaau gacugaggca gauucuuccu gaagcccauu cuccaugggg caacaaggac   2460

accuauucug uccuuguccu uccaucgcug ccccagaaag ccucacauau cuccguuuag   2520

aaucaggucc cuucucccca gaugaagagg agggucucug cuuuguuuuc ucuaucuccu   2580

ccucagacuu gaccaggccc agcaggcccc agaagaccau uacccuauau cccuucuccu   2640

cccuagucac auggccauag gccugcugau ggcucaggaa ggccauugca aggacuccuc   2700

agcuauggga gaggaagcac aucacccauu gacccccgca accccucccu uuccuccucu   2760

gagucccgac uggggccaca ugcagccuga cuucuuugug ccuguugcug ucccugcagu   2820

cuucagaggg ccaccgcagc uccagugcca cggcaggagg cuguuccuga auagccccug   2880

ugguaagggc caggagaguc cuuccauccu ccaaggcccu gcuaaaggac acagcagcca   2940

ggaagucccc ugggccccua gcugaaggac agccugcucc cuccgucucu accaggaaug   3000

gccuuguccu auggaaggca cugccccauc ccaaacuaau cuaggaauca cugucuaacc   3060

acucacuguc augaaugugu acuuaaagga ugagguugag ucauaccaaa uagugauuuc   3120

gauaguucaa aauggugaaa uuagcaauuc uacaugauuc agucuaauca auggauaccg   3180

acuguuuccc acacaagucu ccuguucucu uaagcuuacu cacugacagc cuuucacucu   3240

ccacaaauac auuaaagaua uggccaucac caagccccu aggaugacac cagaccugag   3300

agucugaaga ccuggaucca aguucugacu uuucccccug acagcugugu gaccuucgug   3360

aagucgccaa accucucuga gccccaguca uugcuaguaa gaccugccuu ugaguuggua   3420

ugauguucaa guuagauaac aaaauguuua uacccauuag aacagagaau aaauagaacu   3480

acauuucuug ca                                                       3492
```

<210> SEQ ID NO 13
<211> LENGTH: 3510
<212> TYPE: RNA
<213> ORGANISM: Homo sapiens

<400> SEQUENCE: 13

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaagggcg    240

gcaguaaguc uucagcauca ggcauuuugg ggugacucag uaaaugguag aucuugcuac    300

caguggaaca gccacuaagg auucugcagu gagagcagag ggccagcuaa gugguacucu    360

cccagagacu gucugacuca cgccaccccc uccaccuugg acacaggacg cugugguuuc    420
```

```
ugagccaggu acaaugacuc cuuucgccuc ccccguugcc ccucuggauc cacugcuuaa    480

auacggacga ggacagggcc cugucuccuc agcuucaggc accaccacug accugggaca    540

gugaaucgac aaugccgucu ucugucucgu ggggcauccu ccugcuggca ggccugugcu    600

gccugguccc ugucucccug gcugaggauc cccagggaga ugcugcccag aagacagaua    660

caucccacca ugaucaggau cacccaaccu ucaacaagau cacccccaac cuggcugagu    720

ucgccuucag ccuauaccgc cagcuggcac accaguccaa cagcaccaau aucuucuucu    780

ccccagugag caucgcuaca gccuuugcaa ugcucucccu ggggaccaag gcugacacuc    840

acgaugaaau ccuggagggc cugaauuuca accucacgga gauuccggag gcucagaucc    900

augaaggcuu ccaggaacuc cuccguaccc ucaaccagcc agacagccag cuccagcuga    960

ccaccggcaa uggccuguuc cucagcgagg gccugaagcu aguggauaag uuuuuggagg   1020

auguuaaaaa guuguaccac ucagaagccu ucacugucaa cuucggggac accgaagagg   1080

ccaagaaaca gaucaacgau uacguggaga aggguacuca agggaaaauu guggauuugg   1140

ucaaggagcu ugacagagac acaguuuuug cucuggugaa uuacaucuuc uuuaaaggca   1200

aaugggagag acccuuugaa gucaaggaca ccgaggaaga ggacuuccac guggaccagg   1260

ugaccaccgu gaaggugccu augaugaagc guuuaggcau guuuaacauc cagcacugua   1320

agaagcuguc cagcugggug cugcugauga aauaccuggg caaugccacc gccaucuucu   1380

uccugccuga ugaggggaaa cuacagcacc uggaaaauga acucacccac gauaucauca   1440

ccaaguuccu ggaaaaugaa gacagaaggu cugccagcuu acauuuaccc aaacugucca   1500

uuacuggaac cuaugaucug aagagcgucc ugggucaacu gggcaucacu aaggucuuca   1560

gcaauggggc ugaccucucc ggggucacag aggaggcacc ccugaagcuc uccaaggccg   1620

ugcauaaggc ugugcugacc aucgacgaga aagggacuga agcugcuggg gccauguuuu   1680

uagaggccau acccaugucu aucccccccg aggucaaguu caacaaaccc uuugucuucu   1740

uaaugauuga acaaaauacc aagucucccc ucuucauggg aaaaguggug aaucccaccc   1800

aaaaauaacu gccucucgcu ccucaacccc uccccuccau cccuggcccc cucccuggau   1860

gacauuaaag aaggguugag cuggucccug ccugcaugug acuguaaauc ccucccaugu   1920

uuucucugag ucucccuuug ccugcugagg cuguaugugg gcuccaggua acagugcugu   1980

cuucgggccc ccugaacugu guucauggag caucuggcug gguaggcaca ugcugggcuu   2040

gaauccaggg gggacugaau ccucagcuua cggaccuggg cccaucuguu ucuggagggc   2100

uccagucuuc cuuguccugu cuuggagucc ccaagaagga aucacagggg aggaaccaga   2160

uaccagccau gaccccaggc uccaccaagc aucuucaugu cccccugcuc aucccccacu   2220

cccccccacc cagaguugcu cauccugcca gggcuggcug ugcccacccc aaggcugccc   2280

uccugggggc cccagaacug ccugaucgug ccguggccca guuuuguggc aucugcagca   2340

acacaagaga gaggacaaug uccuccucuu gacccgcugu caccuaacca gacucgggcc   2400

cugcaccucu caggcacuuc uggaaaauga cugaggcaga uucuuccuga agcccauucu   2460

ccauggggca acaaggacac cuauucuguc cuuguccuuc caucgcugcc ccagaaagcc   2520

ucacauaucu ccguuuagaa ucaggucccu ucuccccaga ugaagaggag ggucucugcu   2580

uuguuuucuc uaucuccucc ucagacuuga ccaggcccag caggccccag aagaccauua   2640

cccuauaucc cuucuccucc cuagucacau ggccauaggc cugcugaugg cucaggaagg   2700

ccauugcaag gacuccucag cuaugggaga ggaagcacau cacccauuga cccccgcaac   2760
```

```
cccucccuuu ccuccucuga gucccgacug gggccacaug cagccugacu ucuuugugcc   2820

uguugcuguc ccugcagucu ucagagggcc accgcagcuc cagugccacg gcaggaggcu   2880

guuccugaau agccccugug guaagggcca ggagaguccu uccauccucc aaggcccugc   2940

uaaaggacac agcagccagg aaguccccug ggccccuagc ugaaggacag ccugcucccu   3000

ccgucucuac caggaauggc cuuguccuau ggaaggcacu gccccauccc aaacuaaucu   3060

aggaaucacu gucuaaccac ucacugucau gaauguguac uuaaaggaug agguugaguc   3120

auaccaaaua gugauuucga uaguucaaaa uggugaaauu agcaauucua caugauucag   3180

ucuaaucaau ggauaccgac uguuucccac acaagucucc uguucucuua agcuuacuca   3240

cugacagccu uucacucucc acaaauacau uaaagauaug gccaucacca agcccccuag   3300

gaugacacca gaccugagag ucugaagacc uggauccaag uucugacuuu ucccccugac   3360

agcuguguga ccuucgugaa gucgccaaac cucucugagc cccagucauu gcuaguaaga   3420

ccugccuuug aguugguaug auguucaagu uagauaacaa aauguuuaua cccauuagaa   3480

cagagaauaa auagaacuac auuucuugca                                   3510
```

<210> SEQ ID NO 14
<211> LENGTH: 3303
<212> TYPE: RNA
<213> ORGANISM: Homo sapiens

<400> SEQUENCE: 14

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaagcagc    240

cucccccguu gccccucugg auccacugcu uaaauacgga cgaggacagg gcccugucuc    300

cucagcuuca ggcaccacca cugaccuggg acagugaauc gacaaugccg ucuucugucu    360

cguggggcau ccuccugcug gcaggccugu gcugccuggu cccugucucc cuggcugagg    420

auccccaggg agaugcugcc cagaagacag auacauccca ccaugaucag gaucacccaa    480

ccuucaacaa gaucaccccc aaccuggcug aguucgccuu cagccuauac cgccagcugg    540

cacaccaguc caacagcacc aauaucuucu ucuccccagu gagcaucgcu acagccuuug    600

caaugcucuc ccuggggacc aaggcugaca cucacgauga aauccuggag ggccugaauu    660

ucaaccucac ggagauuccg gaggcucaga uccaugaagg cuuccaggaa cuccuccgua    720

cccucaacca gccagacagc cagcuccagc ugaccaccgg caauggccug uuccucagcg    780

agggccugaa gcuaguggau aaguuuuugg aggauguuaa aaaguuguac cacucagaag    840

ccuucacugu caacuucggg gacaccgaag aggccaagaa acagaucaac gauuacgugg    900

agaaggguac ucaagggaaa auuguggauu uggucaagga gcuugacaga gacacaguuu    960

uugcucuggu gaauuacauc uucuuuaaag gcaaauggga gagacccuuu gaagucaagg   1020

acaccgagga agaggacuuc cacguggacc aggugaccac cgugaaggug ccuaugauga   1080

agcguuuagg cauguuuaac auccagcacu guaagaagcu guccagcugg gugcugcuga   1140

ugaaauaccu gggcaaugcc accgccaucu ucuuccugcc ugaugagggg aaacuacagc   1200

accuggaaaa ugaacucacc cacgauauca ucaccaaguu ccuggaaaau gaagacagaa   1260

ggucugccag cuuacauuua cccaaacugu ccauuacugg aaccuaugau cugaagagcg   1320

uccuggguca acugggcauc acuaaggucu ucagcaaugg ggcugaccuc uccgggguca   1380
```

```
cagaggaggc accccugaag cucuccaagg ccgugcauaa ggcugugcug accaucgacg   1440

agaaagggac ugaagcugcu ggggccaugu uuuuagaggc cauacccaug ucuaucccccc  1500

ccgaggucaa guucaacaaa cccuuugucu ucuuaaugau ugaacaaaau accaagucuc   1560

cccucuucau gggaaaagug gugaauccca cccaaaaaua acugccucuc gcuccucaac   1620

cccuccccuc caucccuggc cccccucccug gaugacauua aagaaggguu gagcuggucc  1680

cugccugcau gugacuguaa aucccuccca uguuuucucu gagucucccu uugccugcug   1740

aggcuguaug ugggcuccag guaacagugc ugucuucggg cccccugaac uguguucaug   1800

gagcaucugg cuggguaggc acaugcuggg cuugaaucca gggggacug aauccucagc    1860

uuacggaccu gggcccaucu guuucuggag ggcuccaguc uuccuugucc ugucuuggag   1920

uccccaagaa ggaaucacag gggaggaacc agauaccagc caugacccca ggcuccacca   1980

agcaucuuca uguccccccug cucaucccccc acucccccccc acccagaguu gcucauccug 2040

ccagggcugg cugugcccac cccaaggcug cccuccuggg ggccccagaa cugccugauc   2100

gugccguggc ccaguuuugu ggcaucugca gcaacacaag agagaggaca auguccuccu   2160

cuugacccgc ugucaccuaa ccagacucgg gcccugcacc ucucaggcac uucuggaaaa   2220

ugacugaggc agauucuucc ugaagcccau ucuccauggg gcaacaagga caccuauucu   2280

guccuugucc uuccaucgcu gccccagaaa gccucacaua ucuccguuua gaaucagguc   2340

ccuucucccc agaugaagag gagggucucu gcuuuguuuu cucuaucucc uccucagacu   2400

ugaccaggcc cagcaggccc cagaagacca uuacccuaua ucccuucucc ucccuaguca   2460

cauggccaua ggccugcuga uggcucagga aggccauugc aaggacuccu cagcuauggg   2520

agaggaagca caucacccau ugacccccgc aaccccuccc uuuccuccuc ugagucccga   2580

cuggggccac augcagccug acuucuuugu gccuguugcu gucccugcag ucuucagagg   2640

gccaccgcag cuccagugcc acggcaggag gcuguuccug aauagccccu gugguaaggg   2700

ccaggagagu ccuuccaucc uccaaggccc ugcuaaagga cacagcagcc aggaaguccc   2760

cugggccccu agcugaagga cagccugcuc ccuccgucuc uaccaggaau ggccuugucc   2820

uauggaaggc acugccccau cccaaacuaa ucuaggaauc acugucuaac cacucacugu   2880

caugaaugug uacuuaaagg augagguuga gucauaccaa auagugauuu cgauaguuca   2940

aaauggugaa auuagcaauu cuacaugauu cagucuaauc aauggauacc gacuguuucc   3000

cacacaaguc uccuguucuc uuaagcuuac ucacugacag ccuuucacuc uccacaaaua   3060

cauuaaagau auggccauca ccaagccccc uaggaugaca ccagaccuga gagucugaag   3120

accuggaucc aaguucugac uuuuccccccu gacagcugug ugaccuucgu gaagucgcca  3180

aaccucucug agccccaguc auugcuagua agaccugccu uugaguuggu augauguuca   3240

aguuagauaa caaaauguuu auacccauua gaacagagaa uaaauagaac uacauuucuu   3300

gca                                                                 3303
```

<210> SEQ ID NO 15
<211> LENGTH: 3300
<212> TYPE: RNA
<213> ORGANISM: Homo sapiens

<400> SEQUENCE: 15

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120
```

-continued

```
cugcugccag gaauuccagg uuggaggggc ggcaaccucc ugccagccuu caggccacuc    180
uccugugccu gccagaagag acagagcuug aggagagcuu gaggagagca ggaaagccuc    240
ccccguugcc ccucuggauc cacugcuuaa auacggacga ggacagggcc cugucuccuc    300
agcuucaggc accaccacug accugggaca gugaaucgac aaugccgucu ucugucucgu    360
ggggcauccu ccugcuggca ggccugugcu gccugguccc ugucucccug gcugaggauc    420
cccagggaga ugcugcccag aagacagaua caucccacca ugaucaggau cacccaaccu    480
ucaacaagau cacccccaac cuggcugagu ucgccuucag ccuauaccgc cagcuggcac    540
accaguccaa cagcaccaau aucuucuucu ccccagugag caucgcuaca gccuuugcaa    600
ugcucucccu ggggaccaag gcugacacuc acgaugaaau ccuggagggc cugaauuuca    660
accucacgga gauuccggag gcucagaucc augaaggcuu ccaggaacuc cuccguaccc    720
ucaaccagcc agacagccag cuccagcuga ccaccggcaa uggccuguuc cucagcgagg    780
gccugaagcu aguggauaag uuuuuggagg auguuaaaaa guuguaccac ucagaagccu    840
ucacugucaa cuucggggac accgaagagg ccaagaaaca gaucaacgau uacguggaga    900
aggguacuca agggaaaauu guggauuugg ucaaggagcu ugacagagac acaguuuuug    960
cucuggugaa uuacaucuuc uuuaaaggca aaugggagag acccuuugaa gucaaggaca   1020
ccgaggaaga ggacuuccac guggaccagg ugaccaccgu gaaggugccu augaugaagc   1080
guuuaggcau guuuaacauc cagcacugua agaagcuguc cagcugggug cugcugauga   1140
aauaccuggg caaugccacc gccaucuucu uccugccuga ugaggggaaa cuacagcacc   1200
uggaaaauga acucacccac gauaucauca ccaaguuccu ggaaaaugaa gacagaaggu   1260
cugccagcuu acauuuaccc aaacugucca uuacuggaac cuaugaucug aagagcgucc   1320
ugggucaacu gggcaucacu aaggucuuca gcaauggggc ugaccucucc ggggucacag   1380
aggaggcacc ccugaagcuc uccaaggccg ugcauaaggc ugugcugacc aucgacgaga   1440
aagggacuga agcugcuggg gccauguuuu uagaggccau acccaugucu auccccccg    1500
aggucaaguu caacaaaccc uuugucuucu uaaugauuga acaaaauacc aagucucccc   1560
ucuucauggg aaaaguggug aaucccaccc aaaaauaacu gccucucgcu ccucaacccc   1620
uccccuccau cccuggcccc cucccuggau gacauuaaag aaggguugag cuggucccug   1680
ccugcaugug acuguaaauc ccucccaugu uuucucugag ucucccuuug ccugcugagg   1740
cuguaugugg gcuccaggua acagugcugu cuucgggccc ccugaacugu guucauggag   1800
caucuggcug gguaggcaca ugcugggcuu gaauccaggg gggacugaau ccucagcuua   1860
cggaccuggg cccaucuguu ucuggagggc uccagucuuc cuuguccugu cuuggagucc   1920
ccaagaagga aucacagggg aggaaccaga uaccagccau gaccccaggc uccaccaagc   1980
aucuucaugu cccccugcuc aucccccacu ccccccccacc cagaguugcu cauccugcca   2040
gggcuggcug ugcccacccc aaggcugccc uccugggggc cccagaacug ccugaucgug   2100
ccguggccca guuuuguggc aucugcagca acacaagaga gaggacaaug uccuccucuu   2160
gacccgcugu caccuaacca gacucgggcc cugcaccucu caggcacuuc uggaaaauga   2220
cugaggcaga uucuuccuga agcccauucu ccauggggca acaaggacac cuauucuguc   2280
cuuguccuuc caucgcugcc ccagaaagcc ucacauaucu ccguuuagaa ucaggucccu   2340
ucuccccaga ugaagaggag ggucucugcu uuguuuucuc uaucuccucc ucagacuuga   2400
ccaggcccag caggccccag aagaccauua cccuauaucc cuucuccucc cuagucacau   2460
ggccauaggc cugcugaugg cucaggaagg ccauugcaag gacuccucag cuaugggaga   2520
```

```
ggaagcacau cacccauuga cccccgcaac cccucccuuu ccuccucuga gucccgacug   2580

gggccacaug cagccugacu ucuuugugcc uguugcuguc ccugcagucu ucagagggcc   2640

accgcagcuc cagugccacg gcaggaggcu guuccugaau agccccugug guaagggcca   2700

ggagaguccu uccauccucc aaggcccugc uaaaggacac agcagccagg aaguccccug   2760

ggccccuagc ugaaggacag ccugcucccu ccgucucuac caggaauggc cuuguccuau   2820

ggaaggcacu gccccauccc aaacuaaucu aggaaucacu gucuaaccac ucacugucau   2880

gaauguguac uuaaaggaug agguugaguc auaccaaaua gugauuucga uaguucaaaa   2940

uggugaaauu agcaauucua caugauucag ucuaaucaau ggauaccgac uguuucccac   3000

acaagucucc uguucucuua agcuuacuca cugacagccu uucacucucc acaaauacau   3060

uaaagauaug gccaucacca agccccccuag gaugacacca gaccugagag ucugaagacc   3120

uggauccaag uucugacuuu ucccccugac agcuguguga ccuucgugaa gucgccaaac   3180

cucucugagc cccagucauu gcuaguaaga ccugccuuug aguugguaug auguucaagu   3240

uagauaacaa aauguuuaua cccauuagaa cagagaauaa auagaacuac auuucuugca   3300
```

<210> SEQ ID NO 16
<211> LENGTH: 3199
<212> TYPE: RNA
<213> ORGANISM: Homo sapiens

<400> SEQUENCE: 16

```
ugggcaggaa cugggcacug ugcccagggc augcacugcc uccacgcagc aacccucaga     60

guccugagcu gaaccaagaa ggaggagggg gucgggccuc cgaggaaggc cuagccgcug    120

cugcugccag gaauuccagg uuggaggggc ggcaaccucc ugccagccuu caggccacuc    180

uccugugccu gccagaagag acagagcuug aggagagcuu gaggagagca ggaaaggaca    240

augccgucuu cugucucgug gggcauccuc cugcuggcag gccugugcug ccugguccu    300

gucucccugg cugaggaucc ccagggagau gcugcccaga agacagauac aucccaccau    360

gaucaggauc acccaaccuu caacaagauc acccccaacc uggcugaguu cgccuucagc    420

cuauaccgcc agcuggcaca ccaguccaac agcaccaaua ucuucuucuc cccagugagc    480

aucgcuacag ccuuugcaau gcucucccug gggaccaagg cugacacuca cgaugaaauc    540

cuggagggcc ugaauuucaa ccucacggag auuccggagg cucagaucca ugaaggcuuc    600

caggaacucc uccguacccu caaccagcca gacagccagc uccagcugac caccggcaau    660

ggccuguucc ucagcgaggg ccugaagcua guggauaagu uuuuggagga uguuaaaaag    720

uuguaccacu cagaagccuu cacugucaac uucggggaca ccgaagaggc caagaaacag    780

aucaacgauu acguggagaa ggguacucaa gggaaaauug uggauuuggu caaggagcuu    840

gacagagaca caguuuuugc ucuggugaau uacaucuucu uuaaaggcaa augggagaga    900

cccuuugaag ucaaggacac cgaggaagag gacuuccacg uggaccaggu gaccaccgug    960

aaggugccua ugaugaagcg uuuaggcaug uuuaacaucc agcacuguaa gaagcugucc   1020

agcugggugc ugcugaugaa auaccugggc aaugccaccg ccaucuucuu ccugccugau   1080

gaggggaaac uacagcaccu ggaaaaugaa cucacccacg auaucaucac caaguuccug   1140

gaaaaugaag acagaagguc ugccagcuua cauuuaccca aacuguccau uacuggaacc   1200

uaugaucuga agagcguccu gggucaacug ggcaucacua aggucuucag caauggggcu   1260

gaccucuccg ggucacaga ggaggcaccc cugaagcucu ccaaggccgu gcauaaggcu   1320
```

```
gugcugacca ucgacgagaa agggacugaa gcugcugggg ccauguuuuu agaggccaua   1380

cccaugucua uccccccga ggucaaguuc aacaaacccu uugucuucuu aaugauugaa   1440

caaaauacca agucuccccu cuucauggga aaagugguga aucccaccca aaaauaacug   1500

ccucucgcuc cucaaccccu ccccuccauc ccuggccccc ucccuggaug acauuaaaga   1560

aggguugagc ugguccugc cugcauguga cuguaaaucc cucccauguu uucucugagu   1620

cucccuuugc cugcugaggc uguauguggg cuccagguaa cagugcuguc uucgggcccc   1680

cugaacugug uucauggagc aucuggcugg guaggcacau gcugggcuug aauccagggg   1740

ggacugaauc cucagcuuac ggaccugggc ccaucuguuu cuggagggcu ccagucuucc   1800

uuguccuguc uuggaguccc caagaaggaa ucacagggga ggaaccagau accagccaug   1860

accccaggcu ccaccaagca ucuucauguc ccccugcuca ucccccacuc ccccccaccc   1920

agaguugcuc auccugccag ggcuggcugu gcccacccca aggcugcccu ccugggggcc   1980

ccagaacugc cugaucgugc cguggcccag uuuuguggca ucugcagcaa cacaagagag   2040

aggacaaugu ccuccucuug acccgcuguc accuaaccag acucgggccc ugcaccucuc   2100

aggcacuucu ggaaaaugac ugaggcagau ucuuccugaa gcccauucuc caugggcaa    2160

caaggacacc uauucugucc uuguccuucc aucgcugccc cagaaagccu cacauaucuc   2220

cguuuagaau cagguccuu cuccccagau gaagaggagg gucucugcuu uguuuucucu    2280

aucuccuccu cagacuugac caggcccagc aggccccaga agaccauuac ccuauauccc   2340

uucuccuccc uagucacaug gccauaggcc ugcugauggc ucaggaaggc cauugcaagg   2400

acuccucagc uaugggagag gaagcacauc acccauugac ccccgcaacc ccucccuuuc   2460

cuccucugag ucccgacugg ggccacaugc agccugacuu cuuugugccu guugcugucc   2520

cugcagucuu cagagggcca ccgcagcucc agugccacgg caggaggcug uuccugaaua   2580

gccccugugg uaagggccag gagaguccuu ccauccucca aggcccugcu aaaggacaca   2640

gcagccagga aguccccugg gccccuagcu gaaggacagc cugcucccuc cgucucuacc   2700

aggaauggcc uuguccuaug gaaggcacug ccccauccca aacuaaucua ggaaucacug   2760

ucuaaccacu cacugucaug aauguguacu uaaaggauga gguugaguca uaccaaauag   2820

ugauuucgau aguucaaaau ggugaaauua gcaauucuac augauucagu cuaaucaaug   2880

gauaccgacu guuucccaca caagucuccu guucucuuaa gcuuacucac ugacagccuu   2940

ucacucucca caaauacauu aaagauaugg ccaucaccaa gcccccuagg augacaccag   3000

accugagagu cugaagaccu ggauccaagu ucugacuuuu cccccugaca gcugugugac   3060

cuucgugaag ucgccaaacc ucucugagcc ccagucauug cuaguaagac cugccuuuga   3120

guugguauga uguucaaguu agauaacaaa auguuuauac ccauuagaac agagaauaaa   3180

uagaacuaca uuucuugca                                                 3199
```

<210> SEQ ID NO 17
<211> LENGTH: 133
<212> TYPE: RNA
<213> ORGANISM: Artificial Sequence
<220> FEATURE:
<223> OTHER INFORMATION: Antisense 901

<400> SEQUENCE: 17

```
ccuggaggcu ugcugaaggc uguaugcugu aagcuggcag accuucuguc guuuuggcca     60

cugacugacg acagaagcug ccagcuuaca ggacacaagg ccuguuacua gcacucacau    120

ggaacaaaug gcc                                                       133
```

<210> SEQ ID NO 18
<211> LENGTH: 133
<212> TYPE: RNA
<213> ORGANISM: Artificial Sequence
<220> FEATURE:
<223> OTHER INFORMATION: Antisense 914

<400> SEQUENCE: 18
ccuggaggcu ugcugaaggc uguaugcuga auguaagcug gcagaccuuc guuuuggcca 60
cugacugacg aaggucucag cuuacauuca ggacacaagg ccuguuacua gcacucacau 120
ggaacaaaug gcc 133

<210> SEQ ID NO 19
<211> LENGTH: 133
<212> TYPE: RNA
<213> ORGANISM: Artificial Sequence
<220> FEATURE:
<223> OTHER INFORMATION: Antisense 943

<400> SEQUENCE: 19
ccuggaggcu ugcugaaggc uguaugcuga uagguuccag uaauggacag guuuuggcca 60
cugacugacc uguccaucug gaaccuauca ggacacaagg ccuguuacua gcacucacau 120
ggaacaaaug gcc 133

<210> SEQ ID NO 20
<211> LENGTH: 1254
<212> TYPE: RNA
<213> ORGANISM: Artificial Sequence
<220> FEATURE:
<223> OTHER INFORMATION: Hardened alpha-1 antitrypsin

<400> SEQUENCE: 20
augccgucuu cugucucgug gggcauccuc cugcuggcag gccugugcug ccuggucccu 60
gucucccugg cugaggaucc ccagggagau gcugcccaga agacagauac aucccaccau 120
gaucaggauc acccaaccuu caacaagauc acccccaacc uggcugaguu cgccuucagc 180
cuauaccgcc agcuggcaca ccaguccaac agcaccaaua ucuucuucuc cccagugagc 240
aucgcuacag ccuuugcaau gcucucccug gggaccaagg cugacacuca cgaugaaauc 300
cuggagggcc ugaauuucaa ccucacggag auuccggagg cucagaucca ugaaggcuuc 360
caggaacucc uccguacccu caaccagcca gacagccagc uccagcugac caccggcaau 420
ggccuguucc ucagcgaggg ccugaagcua guggauaagu uuuuggagga uguuaaaaag 480
uuguaccacu cagaagccuu cacugucaac uucggggaca ccgaagaggc caagaaacag 540
aucaacgauu acguggagaa ggguacucaa gggaaaauug uggauuuggu caaggagcuu 600
gacagagaca caguuuuugc ucuggugaau uacaucuucu uuaaaggcaa augggagaga 660
cccuuugaag ucaaggacac cgaggaagag gacuuccacg uggaccaggu gaccaccgug 720
aaggugccua ugaugaagcg uuuaggcaug uuuaacaucc agcacuguaa gaagcugucc 780
agcugggugc ugcugaugaa auaccugggc aaugccaccg ccaucuucuu ccugccugau 840
gaggggaaac uacagcaccu ggaaaaugaa cucacccacg auaucaucac caaguuccug 900
gaaaaugaag aucgccguag cgcuucucug caccugccca aguuaagcau caccggcacg 960
uacgaccuga agagcguccu gggucaacug ggcaucacua aggucuucag caauggggcu 1020
gaccucuccg gggucacaga ggaggcaccc cugaagcucu ccaaggccgu gcauaaggcu 1080

```
gugcugacca ucgacgagaa agggacugaa gcugcugggg ccauguuuuu agaggccaua   1140

cccaugucua uccccccga ggucaaguuc aacaaacccu uugucuucuu aaugauugaa   1200

caaaauacca agucuccccu cuucauggga aaagugguga aucccaccca aaaa         1254


<210> SEQ ID NO 21
<211> LENGTH: 59
<212> TYPE: RNA
<213> ORGANISM: Artificial Sequence
<220> FEATURE:
<223> OTHER INFORMATION: miRNA 910

<400> SEQUENCE: 21

uaagcuggca gaccuucugu cguuuuggcc acugagugac gacagaagcu gccagcuua      59


<210> SEQ ID NO 22
<211> LENGTH: 59
<212> TYPE: RNA
<213> ORGANISM: Artificial Sequence
<220> FEATURE:
<223> OTHER INFORMATION: miRNA 914

<400> SEQUENCE: 22

aauguaagcu ggcagaccuu cguuuuggcc acugacugac gaaggucuca gcuuacauu      59


<210> SEQ ID NO 23
<211> LENGTH: 58
<212> TYPE: RNA
<213> ORGANISM: Artificial Sequence
<220> FEATURE:
<223> OTHER INFORMATION: miRNA 943

<400> SEQUENCE: 23

auagguucca guaauggaca gguuuggcca cugacugacc uguccaucug gaaccuau       58


<210> SEQ ID NO 24
<211> LENGTH: 7804
<212> TYPE: DNA
<213> ORGANISM: Artificial Sequence
<220> FEATURE:
<223> OTHER INFORMATION: Double 6xmiR-CB-GFP
<220> FEATURE:
<221> NAME/KEY: misc_feature
<222> LOCATION: (17)..(163)
<223> OTHER INFORMATION: inverted terminal repeats (ITR)
<220> FEATURE:
<221> NAME/KEY: enhancer
<222> LOCATION: (182)..(548)
<223> OTHER INFORMATION: Enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: intron
<220> FEATURE:
<221> NAME/KEY: misc_feature
<222> LOCATION: (1502)..(1529)
<223> OTHER INFORMATION: 5' miR
<220> FEATURE:
<221> NAME/KEY: misc_feature
<222> LOCATION: (1530)..(1550)
<223> OTHER INFORMATION: Antisense 901
<220> FEATURE:
<221> NAME/KEY: misc_signal
<222> LOCATION: (1570)..(1588)
<220> FEATURE:
<221> NAME/KEY: misc_feature
<222> LOCATION: (1593)..(1633)
```

<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914
<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: misc_feature
<222> LOCATION: (1936)..(2035)
<223> OTHER INFORMATION: Globin
<220> FEATURE:
<221> NAME/KEY: gene
<222> LOCATION: (2072)..(2788)
<223> OTHER INFORMATION: Green Fluorescent Protein (GFP)
<220> FEATURE:
<221> NAME/KEY: misc_feature
<222> LOCATION: (2818)..(2845)
<223> OTHER INFORMATION: 5' miR
<220> FEATURE:
<221> NAME/KEY: misc_feature
<222> LOCATION: (2846)..(2866)
<223> OTHER INFORMATION: Antisense 901
<220> FEATURE:
<221> NAME/KEY: misc_feature
<222> LOCATION: (2886)..(2904)
<223> OTHER INFORMATION: Sense delta 2
<220> FEATURE:
<221> NAME/KEY: misc_feature
<222> LOCATION: (2909)..(2949)
<223> OTHER INFORMATION: 3' miR
<220> FEATURE:
<221> NAME/KEY: misc_feature
<222> LOCATION: (2962)..(2990)
<223> OTHER INFORMATION: 5' miR
<220> FEATURE:
<221> NAME/KEY: misc_feature
<222> LOCATION: (2991)..(3011)
<223> OTHER INFORMATION: Antisense 914
<220> FEATURE:
<221> NAME/KEY: misc_feature
<222> LOCATION: (3031)..(3049)
<223> OTHER INFORMATION: sense delta 2
<220> FEATURE:
<221> NAME/KEY: misc_feature
<222> LOCATION: (3054)..(3094)
<223> OTHER INFORMATION: 3' miR
<220> FEATURE:
<221> NAME/KEY: misc_feature
<222> LOCATION: (3107)..(3135)
<223> OTHER INFORMATION: 5' miR
<220> FEATURE:
<221> NAME/KEY: misc_feature
<222> LOCATION: (3136)..(3156)
<223> OTHER INFORMATION: Antisense 943
<220> FEATURE:
<221> NAME/KEY: misc_feature
<222> LOCATION: (3176)..(3194)
<223> OTHER INFORMATION: Sense delta 2
<220> FEATURE:
<221> NAME/KEY: misc_feature
<222> LOCATION: (3199)..(3239)
<223> OTHER INFORMATION: 3' miR
<220> FEATURE:
<221> NAME/KEY: polyA_signal
<222> LOCATION: (3258)..(3470)
<223> OTHER INFORMATION: poly A tail
<220> FEATURE:
<221> NAME/KEY: promoter
<222> LOCATION: (3611)..(3739)
<223> OTHER INFORMATION: thymidine kinase promoter (Tkp)
<220> FEATURE:
<221> NAME/KEY: gene
<222> LOCATION: (3751)..(4554)
<223> OTHER INFORMATION: Neo resistance gene
<220> FEATURE:
<221> NAME/KEY: misc_feature
<222> LOCATION: (4807)..(4952)
<223> OTHER INFORMATION: Inverted terminal repeats (ITR)
<220> FEATURE:
<221> NAME/KEY: gene
<222> LOCATION: (5972)..(6832)
<223> OTHER INFORMATION: Ampicillin resistance gene

<400> SEQUENCE: 24

```
gggggggggg ggggggggtt ggccactccc tctctgcgcg ctcgctcgct cactgaggcc     60

gggcgaccaa aggtcgcccg acgcccgggc tttgcccggg cggcctcagt gagcgagcga    120

gcgcgcagag agggagtggc caactccatc actaggggtt cctagatctg aattcggtac    180

cctagttatt aatagtaatc aattacgggg tcattagttc atagcccata tatggagttc    240

cgcgttacat aacttacggt aaatggcccg cctggctgac cgcccaacga cccccgccca    300

ttgacgtcaa taatgacgta tgttcccata gtaacgccaa tagggacttt ccattgacgt    360

caatgggtgg actatttacg gtaaactgcc cacttggcag tacatcaagt gtatcatatg    420

ccaagtacgc cccctattga cgtcaatgac ggtaaatggc ccgcctggca ttatgcccag    480

tacatgacct tatgggactt tcctacttgg cagtacatct acgtattagt catcgctatt    540

accatggtcg aggtgagccc cacgttctgc ttcactctcc ccatctcccc cccctcccca    600

cccccaattt tgtatttatt tattttttaa ttattttgtg cagcgatggg ggcggggggg    660

gggggggggc gcgcgccagg cggggcgggg cggggcgagg ggcggggcgg ggcgaggcgg    720

agaggtgcgg cggcagccaa tcagagcggc gcgctccgaa agtttccttt tatggcgagg    780

cggcggcggc ggcggcccta taaaaagcga agcgcgcggc gggcgggagt cgctgcgacg    840

ctgccttcgc cccgtgcccc gctccgccgc cgcctcgcgc cgcccgcccc ggctctgact    900

gaccgcgtta ctcccacagg tgagcgggcg ggacggccct tctcctccgg gctgtaatta    960

gcgcttggtt taatgacggc ttgtttcttt tctgtggctg cgtgaaagcc ttgaggggct   1020

ccgggagggc cctttgtgcg gggggagcgg gctcgggggg tgcgtgcgtg tgtgtgtgcg   1080

tggggagcgc cgcgtgcggc ccgcgctgcc cggcggctgt gagcgctgcg ggcgcggcgc   1140

ggggctttgt gcgctccgca gtgtgcgcga ggggagcgcg gccgggggcg gtgccccgcg   1200

gtgcgggggg ggctgcgagg ggaacaaagg ctgcgtgcgg ggtgtgtgcg tgggggggtg   1260

agcagggggt gtgggcgcgg cggtcgggct gtaacccccc cctgcacccc cctccccgag   1320

ttgctgagca cggcccggct tcgggtgcgg ggctccgtac ggggcgtggc gcggggctcg   1380
```

```
ccgtgccggg cggggggtgg cggcaggtgg gggtgccggg cggggcgggg ccgcctcggg   1440
ccggggaggg ctcgggggag gggcgcggcg gccccccggag cgccggcgac cggtgctagc   1500
cctggaggct tgctgaaggc tgtatgctgt aagctggcag accttctgtc gttttggcca   1560
ctgactgacg acagaagctg ccagcttaca ggacacaagg cctgttacta gcactcacat   1620
ggaacaaatg gccaccggta tgcatcctgg aggcttgctg aaggctgtat gctgaatgta   1680
agctggcaga ccttcgtttt ggccactgac tgacgaaggt ctcagcttac attcaggaca   1740
caaggcctgt tactagcact cacatggaac aaatggccgc tagctcgcga cctggaggct   1800
tgctgaaggc tgtatgctga taggttccag taatggacag gttttggcca ctgactgacc   1860
tgtccatctg gaacctatca ggacacaagg cctgttacta gcactcacat ggaacaaatg   1920
gcctcgcgat gcatctagag cctctgctaa ccatgttcat gccttcttct tttcctaca    1980
gctcctgggc aacgtgctgg ttattgtgct gtctcatcat tttggcaaag aattcctcga   2040
agatctaggc ctgcaggcgg ccgccgccac catgagcaag ggcgaggaac tgttcactgg   2100
cgtggtccca attctcgtgg aactggatgg cgatgtgaat gggcacaaat tttctgtcag   2160
cggagagggt gaaggtgatg ccacatacgg aaagctcacc ctgaaattca tctgcaccac   2220
tggaaagctc cctgtgccat ggccaacact ggtcactacc ctgacctatg gcgtgcagtg   2280
cttttccaga tacccagacc atatgaagca gcatgacttt ttcaagagcg ccatgcccga   2340
gggctatgtg caggagagaa ccatcttttt caaagatgac gggaactaca agacccgcgc   2400
tgaagtcaag ttcgaaggtg acaccctggt gaatagaatc gagctgaagg gcattgactt   2460
taaggaggat ggaaacattc tcggccacaa gctggaatac aactataact cccacaatgt   2520
gtacatcatg gccgacaagc aaaagaatgg catcaaggtc aacttcaaga tcagacacaa   2580
cattgaggat ggatccgtgc agctggccga ccattatcaa cagaacactc caatcggcga   2640
cggccctgtg ctcctcccag acaaccatta cctgtccacc cagtctgccc tgtctaaaga   2700
tcccaacgaa aagagagacc acatggtcct gctggagttt gtgaccgctg ctgggatcac   2760
acatggcatg gacgagctgt acaagtgacc tgcaggcgcc ggcgaccggt gctagccctg   2820
gaggcttgct gaaggctgta tgctgtaagc tggcagacct tctgtcgttt tggccactga   2880
ctgacgacag aagctgccag cttacaggac acaaggcctg ttactagcac tcacatggaa   2940
caaatggcca ccggtatgca tcctggaggc ttgctgaagg ctgtatgctg aatgtaagct   3000
ggcagacctt cgttttggcc actgactgac gaaggtctca gcttacattc aggacacaag   3060
gcctgttact agcactcaca tggaacaaat ggccgctagc tcgcgacctg gaggcttgct   3120
gaaggctgta tgctgatagg ttccagtaat ggacaggttt tggccactga ctgacctgtc   3180
catctggaac ctatcaggac acaaggcctg ttactagcac tcacatggaa caaatggcct   3240
cgcgatgcat ctagagcggc cgcggggatc cagacatgat aagatacatt gatgagtttg   3300
gacaaaccac aactagaatg cagtgaaaaa aatgctttat ttgtgaaatt tgtgatgcta   3360
ttgctttatt tgtaaccatt ataagctgca ataaacaagt taacaacaac aattgcattc   3420
attttatgtt tcaggttcag ggggaggtgt gggaggtttt ttagtcgacc tcgagcagtg   3480
tggttttgca agaggaagca aaaagcctct ccacccaggc ctggaatgtt tccacccaag   3540
tcgaaggcag tgtggttttg caagaggaag caaaaagcct ctccacccag gcctggaatg   3600
tttccaccca atgtcgagca accccgccca gcgtcttgtc attggcgaat tcgaacacgc   3660
agatgcagtc ggggcggcgc ggtcccaggt ccacttcgca tattaaggtg acgcgtgtgg   3720
cctcgaacac cgagcgaccc tgcagccaat atgggatcgg ccattgaaca agatggattg   3780
```

```
cacgcaggtt ctccggccgc ttgggtggag aggctattcg gctatgactg ggcacaacag   3840
acaatcggct gctctgatgc cgccgtgttc cggctgtcag cgcaggggcg cccggttctt   3900
tttgtcaaga ccgacctgtc cggtgccctg aatgaactgc aggacgaggc agcgcggcta   3960
tcgtggctgg ccacgacggg cgttccttgc gcagctgtgc tcgacgttgt cactgaagcg   4020
ggaagggact ggctgctatt gggcgaagtg ccggggcagg atctcctgtc atctcacctt   4080
gctcctgccg agaaagtatc catcatggct gatgcaatgc ggcggctgca tacgcttgat   4140
ccggctacct gcccattcga ccaccaagcg aaacatcgca tcgagcgagc acgtactcgg   4200
atggaagccg gtcttgtcga tcaggatgat ctggacgaag agcatcaggg gctcgcgcca   4260
gccgaactgt tcgccaggct caaggcgcgc atgcccgacg gcgaggatct cgtcgtgacc   4320
catggcgatg cctgcttgcc gaatatcatg gtggaaaatg gccgcttttc tggattcatc   4380
gactgtggcc ggctgggtgt ggcggaccgc tatcaggaca tagcgttggc tacccgtgat   4440
attgctgaag agcttggcgg cgaatgggct gaccgcttcc tcgtgcttta cggtatcgcc   4500
gctcccgatt cgcagcgcat cgccttctat cgccttcttg acgagttctt ctgaggggat   4560
ccgtcgacta gagctcgctg atcagcctcg actgtgcctt ctagttgcca gccatctgtt   4620
gtttgcccct cccccgtgcc ttccttgacc ctggaaggtg ccactcccac tgtcctttcc   4680
taataaaatg aggaaattgc atcgcattgt ctgagtaggt gtcattctat tctggggggt   4740
ggggtggggc aggacagcaa gggggaggat tgggaagaca atagcaggca tgctggggag   4800
agatctagga acccctagtg atggagttgg ccactccctc tctgcgcgct cgctcgctca   4860
ctgaggccgc ccgggcaaag cccgggcgtc gggcgacctt tggtcgcccg gcctcagtga   4920
gcgagcgagc gcgcagagag ggagtggcca accccccccc cccccccct gcagccctgc   4980
attaatgaat cggccaacgc gcggggagag gcggtttgcg tattgggcgc tcttccgctt   5040
cctcgctcac tgactcgctg cgctcggtcg ttcggctgcg gcgagcggta tcagctcact   5100
caaaggcggt aatacggtta tccacagaat caggggataa cgcaggaaag aacatgtgag   5160
caaaaggcca gcaaaaggcc aggaaccgta aaaaggccgc gttgctggcg tttttccata   5220
ggctccgccc ccctgacgag catcacaaaa atcgacgctc aagtcagagg tggcgaaacc   5280
cgacaggact ataaagatac caggcgtttc cccctggaag ctccctcgtg cgctctcctg   5340
ttccgaccct gccgcttacc ggatacctgt ccgcctttct cccttcggga agcgtggcgc   5400
tttctcaatg ctcacgctgt aggtatctca gttcggtgta ggtcgttcgc tccaagctgg   5460
gctgtgtgca cgaacccccc gttcagcccg accgctgcgc cttatccggt aactatcgtc   5520
ttgagtccaa cccggtaaga cacgacttat cgccactggc agcagccact ggtaacagga   5580
ttagcagagc gaggtatgta ggcggtgcta cagagttctt gaagtggtgg cctaactacg   5640
gctacactag aaggacagta tttggtatct gcgctctgct gaagccagtt accttcggaa   5700
aaagagttgg tagctcttga tccggcaaac aaaccaccgc tggtagcggt ggtttttttg   5760
tttgcaagca gcagattacg cgcagaaaaa aaggatctca agaagatcct ttgatctttt   5820
ctacggggtc tgacgctcag tggaacgaaa actcacgtta agggattttg gtcatgagat   5880
tatcaaaaag gatcttcacc tagatccttt taaattaaaa atgaagtttt aaatcaatct   5940
aaagtatata tgagtaaact tggtctgaca gttaccaatg cttaatcagt gaggcaccta   6000
tctcagcgat ctgtctattt cgttcatcca tagttgcctg actccccgtc gtgtagataa   6060
ctacgatacg ggagggctta ccatctggcc ccagtgctgc aatgataccg cgagacccac   6120
```

```
gctcaccggc tccagattta tcagcaataa accagccagc cggaagggcc gagcgcagaa   6180

gtggtcctgc aactttatcc gcctccatcc agtctattaa ttgttgccgg gaagctagag   6240

taagtagttc gccagttaat agtttgcgca acgttgttgc cattgctaca ggcatcgtgg   6300

tgtcacgctc gtcgtttggt atggcttcat tcagctccgg ttcccaacga tcaaggcgag   6360

ttacatgatc ccccatgttg tgcaaaaaag cggttagctc cttcggtcct ccgatcgttg   6420

tcagaagtaa gttggccgca gtgttatcac tcatggttat ggcagcactg cataattctc   6480

ttactgtcat gccatccgta agatgctttt ctgtgactgg tgagtactca accaagtcat   6540

tctgagaata gtgtatgcgg cgaccgagtt gctcttgccc ggcgtcaata cgggataata   6600

ccgcgccaca tagcagaact ttaaaagtgc tcatcattgg aaaacgttct tcggggcgaa   6660

aactctcaag gatcttaccg ctgttgagat ccagttcgat gtaacccact cgtgcaccca   6720

actgatcttc agcatctttt actttcacca gcgtttctgg gtgagcaaaa acaggaaggc   6780

aaaatgccgc aaaaaaggga ataagggcga cacggaaatg ttgaatactc atactcttcc   6840

tttttcaata ttattgaagc atttatcagg gttattgtct catgagcgga tacatatttg   6900

aatgtattta gaaaaataaa caaatagggg ttccgcgcac atttccccga aaagtgccac   6960

ctgacgtcta agaaaccatt attatcatga cattaaccta taaaaatagg cgtatcacga   7020

ggccctttcg tctcgcgcgt ttcggtgatg acggtgaaaa cctctgacac atgcagctcc   7080

cggagacggt cacagcttgt ctgtaagcgg atgccgggag cagacaagcc cgtcagggcg   7140

cgtcagcggg tgttggcggg tgtcggggct ggcttaacta tgcggcatca gagcagattg   7200

tactgagagt gcaccatatg cggtgtgaaa taccgcacag atgcgtaagg agaaaatacc   7260

gcatcaggaa attgtaaacg ttaatatttt gttaaaattc gcgttaaatt tttgttaaat   7320

cagctcattt tttaaccaat aggccgaaat cggcaaaatc ccttataaat caaaagaata   7380

gaccgagata gggttgagtg ttgttccagt ttggaacaag agtccactat taaagaacgt   7440

ggactccaac gtcaaagggc gaaaaaccgt ctatcagggc gatggcccac tacgtgaacc   7500

atcaccctaa tcaagttttt tggggtcgag gtgccgtaaa gcactaaatc ggaaccctaa   7560

agggagcccc cgatttagag cttgacgggg aaagccggcg aacgtggcga gaaaggaagg   7620

gaagaaagcg aaaggagcgg gcgctagggc gctggcaagt gtagcggtca cgctgcgcgt   7680

aaccaccaca cccgccgcgc ttaatgcgcc gctacagggc gcgtcgcgcc attcgccatt   7740

caggctacgc aactgttggg aagggcgatc ggtgcgggcc tcttcgctat tacgccaggc   7800

tgca                                                                7804
```

<210> SEQ ID NO 25
<211> LENGTH: 7667
<212> TYPE: DNA
<213> ORGANISM: Artificial Sequence
<220> FEATURE:
<223> OTHER INFORMATION: PolyA-3XmiR-CB-GFP
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: Enhancer
<220> FEATURE:
<221> NAME/KEY: promoter
<222> LOCATION: (549)..(1795)
<223> OTHER INFORMATION: Chicken beta actin promoter
<220> FEATURE:
<221> NAME/KEY: Intron
<222> LOCATION: (826)..(1795)
<223> OTHER INFORMATION: Intron
<220> FEATURE:
<221> NAME/KEY: misc_feature
<222> LOCATION: (1796)..(1898)
<223> OTHER INFORMATION: Globin
<220> FEATURE:
<221> NAME/KEY: gene
<222> LOCATION: (1935)..(2651)
<223> OTHER INFORMATION: Green fluorescent protein (GFP)
<220> FEATURE:
<221> NAME/KEY: misc_feature
<222> LOCATION: (2681)..(2708)
<223> OTHER INFORMATION: 5' miR
<220> FEATURE:
<221> NAME/KEY: misc_feature
<222> LOCATION: (2709)..(2729)
<223> OTHER INFORMATION: Antisense 901
<220> FEATURE:
<221> NAME/KEY: misc_feature
<222> LOCATION: (2749)..(2767)
<223> OTHER INFORMATION: Sense delta 2
<220> FEATURE:
<221> NAME/KEY: misc_feature
<222> LOCATION: (2772)..(2812)
<223> OTHER INFORMATION: 3' miR
<220> FEATURE:
<221> NAME/KEY: misc_feature
<222> LOCATION: (2854)..(2874)
<223> OTHER INFORMATION: Antisense 914
<220> FEATURE:
<221> NAME/KEY: misc_feature
<222> LOCATION: (2894)..(2912)
<223> OTHER INFORMATION: Sense delta 2
<220> FEATURE:
<221> NAME/KEY: misc_feature
<222> LOCATION: (2917)..(2957)
<223> OTHER INFORMATION: 3' miR
<220> FEATURE:
<221> NAME/KEY: misc_feature
<222> LOCATION: (2970)..(2998)
<223> OTHER INFORMATION: 5' miR
<220> FEATURE:
<221> NAME/KEY: misc_feature
<222> LOCATION: (2999)..(3019)
<223> OTHER INFORMATION: Antisense 943
<220> FEATURE:
<221> NAME/KEY: misc_feature
<222> LOCATION: (3039)..(3057)
<223> OTHER INFORMATION: Sense delta 2
<220> FEATURE:
<221> NAME/KEY: misc_feature
<222> LOCATION: (3062)..(3102)
<223> OTHER INFORMATION: 3' miR
<220> FEATURE:
<221> NAME/KEY: polyA_signal
<222> LOCATION: (3121)..(3333)
<223> OTHER INFORMATION: polyA tail
<220> FEATURE:
<221> NAME/KEY: promoter
<222> LOCATION: (3474)..(3602)
<223> OTHER INFORMATION: thymidine kinase promoter (Tkp)
<220> FEATURE:
<221> NAME/KEY: gene
<222> LOCATION: (3614)..(4417)
<223> OTHER INFORMATION: Neomycin resistance gene
<220> FEATURE:
<221> NAME/KEY: misc_feature
<222> LOCATION: (4670)..(4815)
<223> OTHER INFORMATION: inverted terminal repeats (ITR)
<220> FEATURE:
<221> NAME/KEY: gene
<222> LOCATION: (5835)..(6695)
<223> OTHER INFORMATION: Ampicillin resistance gene

<400> SEQUENCE: 25
gggggggggg ggggggggtt ggccactccc tctctgcgcg ctcgctcgct cactgaggcc 60

```
gggcgaccaa aggtcgcccg acgcccgggc tttgcccggg cggcctcagt gagcgagcga     120
gcgcgcagag agggagtggc caactccatc actaggggtt cctagatctg aattcggtac     180
cctagttatt aatagtaatc aattacgggg tcattagttc atagcccata tatggagttc     240
cgcgttacat aacttacggt aaatggcccg cctggctgac cgcccaacga cccccgccca     300
ttgacgtcaa taatgacgta tgttcccata gtaacgccaa tagggacttt ccattgacgt     360
caatgggtgg actatttacg gtaaactgcc cacttggcag tacatcaagt gtatcatatg     420
ccaagtacgc cccctattga cgtcaatgac ggtaaatggc ccgcctggca ttatgcccag     480
tacatgacct tatgggactt tcctacttgg cagtacatct acgtattagt catcgctatt     540
accatggtcg aggtgagccc cacgttctgc ttcactctcc ccatctcccc cccctcccca     600
cccccaattt tgtatttatt tatttttaa ttattttgtg cagcgatggg ggcggggggg     660
gggggggggc gcgcgccagg cggggcgggg cggggcgagg ggcggggcgg ggcgaggcgg     720
agaggtgcgg cggcagccaa tcagagcggc gcgctccgaa agtttccttt tatggcgagg     780
cggcggcggc ggcggcccta taaaaagcga agcgcgcggc gggcgggagt cgctgcgacg     840
ctgccttcgc cccgtgcccc gctccgccgc cgcctcgcgc cgcccgcccc ggctctgact     900
gaccgcgtta ctcccacagg tgagcgggcg ggacggccct tctcctccgg gctgtaatta     960
gcgcttggtt taatgacggc ttgtttcttt tctgtggctg cgtgaaagcc ttgaggggct    1020
ccgggagggc cctttgtgcg gggggagcg gctcgggggg tgcgtgcgtg tgtgtgtgcg    1080
tggggagcgc cgcgtgcggc ccgcgctgcc cggcggctgt gagcgctgcg ggcgcggcgc    1140
ggggctttgt gcgctccgca gtgtgcgcga ggggagcgcg gccgggggcg gtgccccgcg    1200
gtgcgggggg ggctgcgagg ggaacaaagg ctgcgtgcgg ggtgtgtgcg tgggggggtg    1260
agcagggggt gtgggcgcgg cggtcgggct gtaacccccc cctgcacccc cctccccgag    1320
ttgctgagca cggcccggct tcgggtgcgg ggctccgtac ggggcgtggc gcggggctcg    1380
ccgtgccggg cgggggtgg cggcaggtgg gggtgccggg cggggcgggg ccgcctcggg    1440
ccggggaggg ctcgggggag ggcgcggcg gcccccggag cgccggcggc tgtcgaggcg    1500
cggcgagccg cagccattgc cttttatggt aatcgtgcga gagggcgcag ggacttcctt    1560
tgtcccaaat ctgtgcggag ccgaaatctg ggaggcgccg ccgcaccccc tctagcgggc    1620
gcggggcgaa gcggtgcggc gccggcagga aggaaatggg cggggagggc cttcgtgcgt    1680
cgccgcgccg ccgtcccctt ctccctctcc agcctcgggg ctgtccgcgg ggggacggct    1740
gccttcgggg gggacggggc agggcgggt tcggcttctg gcgtgtgacc ggcggctcta    1800
gagcctctgc taaccatgtt catgccttct tctttttcct acagctcctg ggcaacgtgc    1860
tggttattgt gctgtctcat cattttggca aagaattcct cgaagatcta ggcctgcagg    1920
cggccgccgc caccatgagc aagggcgagg aactgttcac tggcgtggtc ccaattctcg    1980
tggaactgga tggcgatgtg aatgggcaca aattttctgt cagcggagag ggtgaaggtg    2040
atgccacata cggaaagctc accctgaaat tcatctgcac cactggaaag ctccctgtgc    2100
catggccaac actggtcact accctgacct atggcgtgca gtgcttttcc agatacccag    2160
accatatgaa gcagcatgac tttttcaaga gcgccatgcc cgagggctat gtgcaggaga    2220
gaaccatctt tttcaaagat gacgggaact acaagacccg cgctgaagtc aagttcgaag    2280
gtgacaccct ggtgaataga atcgagctga agggcattga ctttaaggag gatggaaaca    2340
ttctcggcca caagctggaa tacaactata actcccacaa tgtgtacatc atggccgaca    2400
agcaaaagaa tggcatcaag gtcaacttca agatcagaca caacattgag gatggatccg    2460
```

```
tgcagctggc cgaccattat caacagaaca ctccaatcgg cgacggccct gtgctcctcc   2520
cagacaacca ttacctgtcc acccagtctg ccctgtctaa agatcccaac gaaaagagag   2580
accacatggt cctgctggag tttgtgaccg ctgctgggat cacacatggc atggacgagc   2640
tgtacaagtg acctgcaggc gccggcgacc ggtgctagcc ctggaggctt gctgaaggct   2700
gtatgctgta agctggcaga ccttctgtcg ttttggccac tgactgacga cagaagctgc   2760
cagcttacag gacacaaggc ctgttactag cactcacatg gaacaaatgg ccaccggtat   2820
gcatcctgga ggcttgctga aggctgtatg ctgaatgtaa gctggcagac cttcgttttg   2880
gccactgact gacgaaggtc tcagcttaca ttcaggacac aaggcctgtt actagcactc   2940
acatggaaca aatggccgct agctcgcgac ctggaggctt gctgaaggct gtatgctgat   3000
aggttccagt aatggacagg ttttggccac tgactgacct gtccatctgg aacctatcag   3060
gacacaaggc ctgttactag cactcacatg gaacaaatgg cctcgcgatg catctagagc   3120
ggccgcgggg atccagacat gataagatac attgatgagt ttggacaaac cacaactaga   3180
atgcagtgaa aaaaatgctt tatttgtgaa atttgtgatg ctattgcttt atttgtaacc   3240
attataagct gcaataaaca agttaacaac aacaattgca ttcattttat gtttcaggtt   3300
cagggggagg tgtgggaggt tttttagtcg acctcgagca gtgtggtttt gcaagaggaa   3360
gcaaaaagcc tctccaccca ggcctggaat gtttccaccc aagtcgaagg cagtgtggtt   3420
ttgcaagagg aagcaaaaag cctctccacc caggcctgga atgtttccac ccaatgtcga   3480
gcaaccccgc ccagcgtctt gtcattggcg aattcgaaca cgcagatgca gtcggggcgg   3540
cgcggtccca ggtccacttc gcatattaag gtgacgcgtg tggcctcgaa caccgagcga   3600
ccctgcagcc aatatgggat cggccattga acaagatgga ttgcacgcag gttctccggc   3660
cgcttgggtg gagaggctat tcggctatga ctgggcacaa cagacaatcg gctgctctga   3720
tgccgccgtg ttccggctgt cagcgcaggg gcgcccggtt ctttttgtca agaccgacct   3780
gtccggtgcc ctgaatgaac tgcaggacga ggcagcgcgg ctatcgtggc tggccacgac   3840
gggcgttcct tgcgcagctg tgctcgacgt tgtcactgaa gcgggaaggg actggctgct   3900
attgggcgaa gtgccggggc aggatctcct gtcatctcac cttgctcctg ccgagaaagt   3960
atccatcatg gctgatgcaa tgcggcggct gcatacgctt gatccggcta cctgcccatt   4020
cgaccaccaa gcgaaacatc gcatcgagcg agcacgtact cggatggaag ccggtcttgt   4080
cgatcaggat gatctggacg aagagcatca ggggctcgcg ccagccgaac tgttcgccag   4140
gctcaaggcg cgcatgcccg acggcgagga tctcgtcgtg acccatggcg atgcctgctt   4200
gccgaatatc atggtggaaa atggccgctt ttctggattc atcgactgtg gccggctggg   4260
tgtggcggac cgctatcagg acatagcgtt ggctacccgt gatattgctg aagagcttgg   4320
cggcgaatgg gctgaccgct tcctcgtgct ttacggtatc gccgctcccg attcgcagcg   4380
catcgccttc tatcgccttc ttgacgagtt cttctgaggg gatccgtcga ctagagctcg   4440
ctgatcagcc tcgactgtgc cttctagttg ccagccatct gttgtttgcc cctcccccgt   4500
gccttccttg accctggaag gtgccactcc cactgtcctt tcctaataaa atgaggaaat   4560
tgcatcgcat tgtctgagta ggtgtcattc tattctgggg ggtggggtgg ggcaggacag   4620
caagggggag gattgggaag acaatagcag gcatgctggg gagagatcta ggaaccccta   4680
gtgatggagt tggccactcc ctctctgcgc gctcgctcgc tcactgaggc cgcccgggca   4740
aagcccgggc gtcgggcgac ctttggtcgc ccggcctcag tgagcgagcg agcgcgcaga   4800
```

-continued

```
gagggagtgg ccaacccccc cccccccccc cctgcagccc tgcattaatg aatcggccaa   4860
cgcgcgggga gaggcggttt gcgtattggg cgctcttccg cttcctcgct cactgactcg   4920
ctgcgctcgg tcgttcggct gcggcgagcg gtatcagctc actcaaaggc ggtaatacgg   4980
ttatccacag aatcagggga taacgcagga aagaacatgt gagcaaaagg ccagcaaaag   5040
gccaggaacc gtaaaaaggc cgcgttgctg gcgtttttcc ataggctccg cccccctgac   5100
gagcatcaca aaaatcgacg ctcaagtcag aggtggcgaa acccgacagg actataaaga   5160
taccaggcgt ttccccctgg aagctccctc gtgcgctctc ctgttccgac cctgccgctt   5220
accggatacc tgtccgcctt tctcccttcg ggaagcgtgg cgctttctca atgctcacgc   5280
tgtaggtatc tcagttcggt gtaggtcgtt cgctccaagc tgggctgtgt gcacgaaccc   5340
cccgttcagc ccgaccgctg cgccttatcc ggtaactatc gtcttgagtc caacccggta   5400
agacacgact tatcgccact ggcagcagcc actggtaaca ggattagcag agcgaggtat   5460
gtaggcggtg ctacagagtt cttgaagtgg tggcctaact acggctacac tagaaggaca   5520
gtatttggta tctgcgctct gctgaagcca gttaccttcg gaaaaagagt tggtagctct   5580
tgatccggca aacaaaccac cgctggtagc ggtggttttt ttgtttgcaa gcagcagatt   5640
acgcgcagaa aaaaaggatc tcaagaagat cctttgatct tttctacggg gtctgacgct   5700
cagtggaacg aaaactcacg ttaagggatt ttggtcatga gattatcaaa aaggatcttc   5760
acctagatcc ttttaaatta aaaatgaagt tttaaatcaa tctaaagtat atatgagtaa   5820
acttggtctg acagttacca atgcttaatc agtgaggcac ctatctcagc gatctgtcta   5880
tttcgttcat ccatagttgc ctgactcccc gtcgtgtaga taactacgat acgggagggc   5940
ttaccatctg gccccagtgc tgcaatgata ccgcgagacc cacgctcacc ggctccagat   6000
ttatcagcaa taaaccagcc agccggaagg gccgagcgca gaagtggtcc tgcaacttta   6060
tccgcctcca tccagtctat taattgttgc cgggaagcta gagtaagtag ttcgccagtt   6120
aatagtttgc gcaacgttgt tgccattgct acaggcatcg tggtgtcacg ctcgtcgttt   6180
ggtatggctt cattcagctc cggttcccaa cgatcaaggc gagttacatg atcccccatg   6240
ttgtgcaaaa aagcggttag ctccttcggt cctccgatcg ttgtcagaag taagttggcc   6300
gcagtgttat cactcatggt tatggcagca ctgcataatt ctcttactgt catgccatcc   6360
gtaagatgct tttctgtgac tggtgagtac tcaaccaagt cattctgaga atagtgtatg   6420
cggcgaccga gttgctcttg cccggcgtca atacgggata ataccgcgcc acatagcaga   6480
actttaaaag tgctcatcat tggaaaacgt tcttcggggc gaaaactctc aaggatctta   6540
ccgctgttga gatccagttc gatgtaaccc actcgtgcac ccaactgatc ttcagcatct   6600
tttactttca ccagcgtttc tgggtgagca aaaacaggaa ggcaaaatgc cgcaaaaaag   6660
ggaataaggg cgacacggaa atgttgaata ctcatactct tcctttttca atattattga   6720
agcatttatc agggttattg tctcatgagc ggatacatat ttgaatgtat ttagaaaaat   6780
aaacaaatag gggttccgcg cacatttccc cgaaaagtgc cacctgacgt ctaagaaacc   6840
attattatca tgacattaac ctataaaaat aggcgtatca cgaggccctt tcgtctcgcg   6900
cgtttcggtg atgacggtga aaacctctga cacatgcagc tcccggagac ggtcacagct   6960
tgtctgtaag cggatgccgg gagcagacaa gcccgtcagg gcgcgtcagc gggtgttggc   7020
gggtgtcggg gctggcttaa ctatgcggca tcagagcaga ttgtactgag agtgcaccat   7080
atgcggtgtg aaataccgca cagatgcgta aggagaaaat accgcatcag gaaattgtaa   7140
acgttaatat tttgttaaaa ttcgcgttaa atttttgtta aatcagctca ttttttaacc   7200
```

```
aataggccga aatcggcaaa atcccttata aatcaaaaga atagaccgag atagggttga   7260

gtgttgttcc agtttggaac aagagtccac tattaaagaa cgtggactcc aacgtcaaag   7320

ggcgaaaaac cgtctatcag ggcgatggcc cactacgtga accatcaccc taatcaagtt   7380

ttttggggtc gaggtgccgt aaagcactaa atcggaaccc taaagggagc ccccgattta   7440

gagcttgacg gggaaagccg gcgaacgtgg cgagaaagga agggaagaaa gcgaaaggag   7500

cgggcgctag ggcgctggca agtgtagcgg tcacgctgcg cgtaaccacc acacccgccg   7560

cgcttaatgc gccgctacag ggcgcgtcgc gccattcgcc attcaggcta cgcaactgtt   7620

gggaagggcg atcggtgcgg gcctcttcgc tattacgcca ggctgca                 7667
```

```
<210> SEQ ID NO 26
<211> LENGTH: 7337
<212> TYPE: DNA
<213> ORGANISM: Artificial Sequence
<220> FEATURE:
<223> OTHER INFORMATION: Intronic-3XmiR-CB-GFP
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: Chicken beta actin intron
<220> FEATURE:
<221> NAME/KEY: misc_feature
<222> LOCATION: (1502)..(1529)
<223> OTHER INFORMATION: 5' miR
<220> FEATURE:
<221> NAME/KEY: misc_feature
<222> LOCATION: (1530)..(1550)
<223> OTHER INFORMATION: Antisense 901
<220> FEATURE:
<221> NAME/KEY: misc_feature
<222> LOCATION: (1570)..(1588)
<223> OTHER INFORMATION: Sense delta 2
<220> FEATURE:
<221> NAME/KEY: misc_feature
<222> LOCATION: (1593)..(1633)
<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914
<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
```

<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: gene
<222> LOCATION: (2072)..(2788)
<223> OTHER INFORMATION: GFP
<220> FEATURE:
<221> NAME/KEY: polyA_signal
<222> LOCATION: (2789)..(3003)
<223> OTHER INFORMATION: polyA tail
<220> FEATURE:
<221> NAME/KEY: promoter
<222> LOCATION: (3144)..(3272)
<223> OTHER INFORMATION: thymidine kinase promoter (Tkp)
<220> FEATURE:
<221> NAME/KEY: gene
<222> LOCATION: (3284)..(4087)
<223> OTHER INFORMATION: Neomycin resistance gene
<220> FEATURE:
<221> NAME/KEY: misc_feature
<222> LOCATION: (4340)..(4485)
<223> OTHER INFORMATION: Inverted terminal repeats (ITR)
<220> FEATURE:
<221> NAME/KEY: gene
<222> LOCATION: (5505)..(6365)
<223> OTHER INFORMATION: Ampicillin (complement)

<400> SEQUENCE: 26

```
gggggggggg gggggggtt ggccactccc tctctgcgcg ctcgctcgct cactgaggcc     60

gggcgaccaa aggtcgcccg acgcccgggc tttgcccggg cggcctcagt gagcgagcga    120

gcgcgcagag agggagtggc caactccatc actaggggtt cctagatctg aattcggtac    180

cctagttatt aatagtaatc aattacgggg tcattagttc atagcccata tatggagttc    240

cgcgttacat aacttacggt aaatggcccg cctggctgac cgcccaacga cccccgccca    300

ttgacgtcaa taatgacgta tgttcccata gtaacgccaa tagggacttt ccattgacgt    360

caatgggtgg actatttacg gtaaactgcc cacttggcag tacatcaagt gtatcatatg    420

ccaagtacgc cccctattga cgtcaatgac ggtaaatggc ccgcctggca ttatgcccag    480

tacatgacct tatgggactt tcctacttgg cagtacatct acgtattagt catcgctatt    540

accatggtcg aggtgagccc cacgttctgc ttcactctcc ccatctcccc cccctcccca    600

cccccaattt tgtatttatt tattttttaa ttattttgtg cagcgatggg ggcggggggg    660

ggggggggc gcgcgccagg cggggcgggg cggggcgagg ggcggggcgg ggcgaggcgg    720

agaggtgcgg cggcagccaa tcagagcggc gcgctccgaa agtttccttt tatggcgagg    780

cggcggcggc ggcggcccta taaaaagcga agcgcgcggc gggcgggagt cgctgcgacg    840

ctgccttcgc cccgtgcccc gctccgccgc cgcctcgcgc cgcccgcccc ggctctgact    900

gaccgcgtta ctcccacagg tgagcgggcg ggacggccct tctcctccgg gctgtaatta    960

gcgcttggtt taatgacggc ttgtttcttt tctgtggctg cgtgaaagcc ttgaggggct   1020

ccgggagggc cctttgtgcg gggggagcg gctcgggggg tgcgtgcgtg tgtgtgtgcg   1080

tggggagcgc cgcgtgcggc ccgcgctgcc cggcggctgt gagcgctgcg ggcgcggcgc   1140

ggggctttgt gcgctccgca gtgtgcgcga ggggagcgcg gccgggggcg gtgccccgcg   1200

gtgcgggggg ggctgcgagg ggaacaaagg ctgcgtgcgg ggtgtgtgcg tgggggggtg   1260

agcagggggt gtgggcgcgg cggtcgggct gtaacccccc cctgcacccc cctccccgag   1320
```

```
ttgctgagca cggcccggct tcgggtgcgg ggctccgtac ggggcgtggc gcggggctcg   1380
ccgtgccggg cggggggtgg cggcaggtgg gggtgccggg cggggcgggg ccgcctcggg   1440
ccggggaggg ctcgggggag gggcgcggcg gcccccggag cgccggcgac cggtgctagc   1500
cctggaggct tgctgaaggc tgtatgctgt aagctggcag accttctgtc gttttggcca   1560
ctgactgacg acagaagctg ccagcttaca ggacacaagg cctgttacta gcactcacat   1620
ggaacaaatg gccaccggta tgcatcctgg aggcttgctg aaggctgtat gctgaatgta   1680
agctggcaga ccttcgtttt ggccactgac tgacgaaggt ctcagcttac attcaggaca   1740
caaggcctgt tactagcact cacatggaac aaatggccgc tagctcgcga cctggaggct   1800
tgctgaaggc tgtatgctga taggttccag taatggacag gttttggcca ctgactgacc   1860
tgtccatctg gaacctatca ggacacaagg cctgttacta gcactcacat ggaacaaatg   1920
gcctcgcgat gcatctagag cctctgctaa ccatgttcat gccttcttct tttcctaca   1980
gctcctgggc aacgtgctgg ttattgtgct gtctcatcat tttggcaaag aattcctcga   2040
agatctaggc ctgcaggcgg ccgccgccac catgagcaag ggcgaggaac tgttcactgg   2100
cgtggtccca attctcgtgg aactggatgg cgatgtgaat gggcacaaat tttctgtcag   2160
cggagagggt gaaggtgatg ccacatacgg aaagctcacc ctgaaattca tctgcaccac   2220
tggaaagctc cctgtgccat ggccaacact ggtcactacc ctgacctatg gcgtgcagtg   2280
cttttccaga tacccagacc atatgaagca gcatgacttt ttcaagagcg ccatgcccga   2340
gggctatgtg caggagagaa ccatcttttt caaagatgac gggaactaca agacccgcgc   2400
tgaagtcaag ttcgaaggtg acaccctggt gaatagaatc gagctgaagg gcattgactt   2460
taaggaggat ggaaacattc tcggccacaa gctggaatac aactataact cccacaatgt   2520
gtacatcatg gccgacaagc aaaagaatgg catcaaggtc aacttcaaga tcagacacaa   2580
cattgaggat ggatccgtgc agctggccga ccattatcaa cagaacactc caatcggcga   2640
cggccctgtg ctcctcccag acaaccatta cctgtccacc cagtctgccc tgtctaaaga   2700
tcccaacgaa aagagagacc acatggtcct gctggagttt gtgaccgctg ctgggatcac   2760
acatggcatg gacgagctgt acaagtgagc ggccgcgggg atccagacat gataagatac   2820
attgatgagt ttggacaaac cacaactaga atgcagtgaa aaaaatgctt tatttgtgaa   2880
atttgtgatg ctattgcttt atttgtaacc attataagct gcaataaaca agttaacaac   2940
aacaattgca ttcattttat gtttcaggtt cagggggagg tgtgggaggt tttttagtcg   3000
acctcgagca gtgtggtttt gcaagaggaa gcaaaaagcc tctccaccca ggcctggaat   3060
gtttccaccc aagtcgaagg cagtgtggtt ttgcaagagg aagcaaaaag cctctccacc   3120
caggcctgga atgtttccac ccaatgtcga gcaaccccgc ccagcgtctt gtcattggcg   3180
aattcgaaca cgcagatgca gtcggggcgg cgcggtccca ggtccacttc gcatattaag   3240
gtgacgcgtg tggcctcgaa caccgagcga ccctgcagcc aatatgggat cggccattga   3300
acaagatgga ttgcacgcag gttctccggc cgcttgggtg gagaggctat tcggctatga   3360
ctgggcacaa cagacaatcg gctgctctga tgccgccgtg ttccggctgt cagcgcaggg   3420
gcgcccggtt ctttttgtca agaccgacct gtccggtgcc ctgaatgaac tgcaggacga   3480
ggcagcgcgg ctatcgtggc tggccacgac gggcgttcct tgcgcagctg tgctcgacgt   3540
tgtcactgaa gcgggaaggg actggctgct attgggcgaa gtgccggggc aggatctcct   3600
gtcatctcac cttgctcctg ccgagaaagt atccatcatg gctgatgcaa tgcggcggct   3660
```

```
gcatacgctt gatccggcta cctgcccatt cgaccaccaa gcgaaacatc gcatcgagcg   3720
agcacgtact cggatggaag ccggtcttgt cgatcaggat gatctggacg aagagcatca   3780
ggggctcgcg ccagccgaac tgttcgccag gctcaaggcg cgcatgcccg acggcgagga   3840
tctcgtcgtg acccatggcg atgcctgctt gccgaatatc atggtggaaa atggccgctt   3900
ttctggattc atcgactgtg gccggctggg tgtggcggac cgctatcagg acatagcgtt   3960
ggctacccgt gatattgctg aagagcttgg cggcgaatgg gctgaccgct tcctcgtgct   4020
ttacggtatc gccgctcccg attcgcagcg catcgccttc tatcgccttc ttgacgagtt   4080
cttctgaggg gatccgtcga ctagagctcg ctgatcagcc tcgactgtgc cttctagttg   4140
ccagccatct gttgtttgcc cctcccccgt gccttccttg accctggaag gtgccactcc   4200
cactgtcctt tcctaataaa atgaggaaat tgcatcgcat tgtctgagta ggtgtcattc   4260
tattctgggg ggtggggtgg ggcaggacag caagggggag gattgggaag acaatagcag   4320
gcatgctggg gagagatcta ggaaccccta gtgatggagt tggccactcc ctctctgcgc   4380
gctcgctcgc tcactgaggc cgcccgggca aagcccgggc gtcgggcgac ctttggtcgc   4440
ccggcctcag tgagcgagcg agcgcgcaga gagggagtgg ccaacccccc cccccccccc   4500
cctgcagccc tgcattaatg aatcggccaa cgcgcgggga gaggcggttt gcgtattggg   4560
cgctcttccg cttcctcgct cactgactcg ctgcgctcgg tcgttcggct gcggcgagcg   4620
gtatcagctc actcaaaggc ggtaatacgg ttatccacag aatcagggga taacgcagga   4680
aagaacatgt gagcaaaagg ccagcaaaag gccaggaacc gtaaaaaggc cgcgttgctg   4740
gcgtttttcc ataggctccg cccccctgac gagcatcaca aaaatcgacg ctcaagtcag   4800
aggtggcgaa acccgacagg actataaaga taccaggcgt ttccccctgg aagctccctc   4860
gtgcgctctc ctgttccgac cctgccgctt accggatacc tgtccgcctt tctcccttcg   4920
ggaagcgtgg cgctttctca atgctcacgc tgtaggtatc tcagttcggt gtaggtcgtt   4980
cgctccaagc tgggctgtgt gcacgaaccc cccgttcagc ccgaccgctg cgccttatcc   5040
ggtaactatc gtcttgagtc caacccggta agacacgact tatcgccact ggcagcagcc   5100
actggtaaca ggattagcag agcgaggtat gtaggcggtg ctacagagtt cttgaagtgg   5160
tggcctaact acggctacac tagaaggaca gtatttggta tctgcgctct gctgaagcca   5220
gttaccttcg gaaaaagagt tggtagctct tgatccggca aacaaaccac cgctggtagc   5280
ggtggttttt ttgtttgcaa gcagcagatt acgcgcagaa aaaaaggatc tcaagaagat   5340
cctttgatct tttctacggg gtctgacgct cagtggaacg aaaactcacg ttaagggatt   5400
ttggtcatga gattatcaaa aaggatcttc acctagatcc ttttaaatta aaaatgaagt   5460
tttaaatcaa tctaaagtat atatgagtaa acttggtctg acagttacca atgcttaatc   5520
agtgaggcac ctatctcagc gatctgtcta tttcgttcat ccatagttgc ctgactcccc   5580
gtcgtgtaga taactacgat acgggagggc ttaccatctg gccccagtgc tgcaatgata   5640
ccgcgagacc cacgctcacc ggctccagat ttatcagcaa taaaccagcc agccggaagg   5700
gccgagcgca gaagtggtcc tgcaacttta tccgcctcca tccagtctat taattgttgc   5760
cgggaagcta gagtaagtag ttcgccagtt aatagtttgc gcaacgttgt tgccattgct   5820
acaggcatcg tggtgtcacg ctcgtcgttt ggtatggctt cattcagctc cggttcccaa   5880
cgatcaaggc gagttacatg atcccccatg ttgtgcaaaa aagcggttag ctccttcggt   5940
cctccgatcg ttgtcagaag taagttggcc gcagtgttat cactcatggt tatggcagca   6000
ctgcataatt ctcttactgt catgccatcc gtaagatgct tttctgtgac tggtgagtac   6060
```

```
tcaaccaagt cattctgaga atagtgtatg cggcgaccga gttgctcttg cccggcgtca   6120
atacgggata ataccgcgcc acatagcaga actttaaaag tgctcatcat tggaaaacgt   6180
tcttcggggc gaaaactctc aaggatctta ccgctgttga gatccagttc gatgtaaccc   6240
actcgtgcac ccaactgatc ttcagcatct tttactttca ccagcgtttc tgggtgagca   6300
aaaacaggaa ggcaaaatgc cgcaaaaaag ggaataaggg cgacacggaa atgttgaata   6360
ctcatactct tcctttttca atattattga agcatttatc agggttattg tctcatgagc   6420
ggatacatat ttgaatgtat ttagaaaaat aaacaaatag gggttccgcg cacatttccc   6480
cgaaaagtgc cacctgacgt ctaagaaacc attattatca tgacattaac ctataaaaat   6540
aggcgtatca cgaggccctt tcgtctcgcg cgtttcggtg atgacggtga aaacctctga   6600
cacatgcagc tcccggagac ggtcacagct tgtctgtaag cggatgccgg gagcagacaa   6660
gcccgtcagg gcgcgtcagc gggtgttggc gggtgtcggg gctggcttaa ctatgcggca   6720
tcagagcaga ttgtactgag agtgcaccat atgcggtgtg aaataccgca cagatgcgta   6780
aggagaaaat accgcatcag gaaattgtaa acgttaatat tttgttaaaa ttcgcgttaa   6840
atttttgtta aatcagctca ttttttaacc aataggccga aatcggcaaa atcccttata   6900
aatcaaaaga atagaccgag atagggttga gtgttgttcc agtttggaac aagagtccac   6960
tattaaagaa cgtggactcc aacgtcaaag ggcgaaaaac cgtctatcag ggcgatggcc   7020
cactacgtga accatcaccc taatcaagtt ttttggggtc gaggtgccgt aaagcactaa   7080
atcggaaccc taaagggagc ccccgattta gagcttgacg gggaaagccg gcgaacgtgg   7140
cgagaaagga agggaagaaa gcgaaaggag cgggcgctag ggcgctggca agtgtagcgg   7200
tcacgctgcg cgtaaccacc acacccgccg cgcttaatgc gccgctacag ggcgcgtcgc   7260
gccattcgcc attcaggcta cgcaactgtt gggaagggcg atcggtgcgg gcctcttcgc   7320
tattacgcca ggctgca                                                  7337
```

```
<210> SEQ ID NO 27
<211> LENGTH: 8223
<212> TYPE: DNA
<213> ORGANISM: Artificial Sequence
<220> FEATURE:
<223> OTHER INFORMATION: PolyA-3XmiR-CB-AAT
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: enhancer
<220> FEATURE:
<221> NAME/KEY: promoter
<222> LOCATION: (549)..(1795)
<223> OTHER INFORMATION: Chicken beta actin promoter
<220> FEATURE:
<221> NAME/KEY: Intron
<222> LOCATION: (826)..(1795)
<223> OTHER INFORMATION: Intron
<220> FEATURE:
<221> NAME/KEY: misc_feature
<222> LOCATION: (1796)..(1898)
<223> OTHER INFORMATION: Globin
<220> FEATURE:
<221> NAME/KEY: gene
<222> LOCATION: (1921)..(3174)
<223> OTHER INFORMATION: Hardened alpha-1 antitrypsin (AAT)
<220> FEATURE:
<221> NAME/KEY: misc_signal
<222> LOCATION: (3175)..(3204)
```

<223> OTHER INFORMATION: Cmyc-tag
<220> FEATURE:
<221> NAME/KEY: misc_feature
<222> LOCATION: (3237)..(3264)
<223> OTHER INFORMATION: 5' miR
<220> FEATURE:
<221> NAME/KEY: misc_feature
<222> LOCATION: (3265)..(3285)
<223> OTHER INFORMATION: Antisense 901
<220> FEATURE:
<221> NAME/KEY: misc_feature
<222> LOCATION: (3305)..(3323)
<223> OTHER INFORMATION: Sense delta 2
<220> FEATURE:
<221> NAME/KEY: misc_feature
<222> LOCATION: (3328)..(3368)
<223> OTHER INFORMATION: 3' miR
<220> FEATURE:
<221> NAME/KEY: misc_feature
<222> LOCATION: (3381)..(3409)
<223> OTHER INFORMATION: 5' miR
<220> FEATURE:
<221> NAME/KEY: misc_feature
<222> LOCATION: (3410)..(3430)
<223> OTHER INFORMATION: Antisense 914
<220> FEATURE:
<221> NAME/KEY: misc_feature
<222> LOCATION: (3450)..(3468)
<223> OTHER INFORMATION: Sense delta 2
<220> FEATURE:
<221> NAME/KEY: misc_feature
<222> LOCATION: (3473)..(3513)
<223> OTHER INFORMATION: 3' miR
<220> FEATURE:
<221> NAME/KEY: misc_feature
<222> LOCATION: (3526)..(3554)
<223> OTHER INFORMATION: 5' miR
<220> FEATURE:
<221> NAME/KEY: misc_feature
<222> LOCATION: (3555)..(3575)
<223> OTHER INFORMATION: Antisense 943
<220> FEATURE:
<221> NAME/KEY: misc_feature
<222> LOCATION: (3595)..(3613)
<223> OTHER INFORMATION: Sense delta 2
<220> FEATURE:
<221> NAME/KEY: misc_feature
<222> LOCATION: (3618)..(3658)
<223> OTHER INFORMATION: 3' miR
<220> FEATURE:
<221> NAME/KEY: polyA_signal
<222> LOCATION: (3677)..(3889)
<223> OTHER INFORMATION: polyA tail
<220> FEATURE:
<221> NAME/KEY: promoter
<222> LOCATION: (4030)..(4158)
<223> OTHER INFORMATION: thymidine kinase promoter (Tkp)
<220> FEATURE:
<221> NAME/KEY: gene
<222> LOCATION: (4170)..(4973)
<223> OTHER INFORMATION: Neomycin resistance gene
<220> FEATURE:
<221> NAME/KEY: misc_feature
<222> LOCATION: (5226)..(5371)
<223> OTHER INFORMATION: Inverted terminal repeats (ITR)
<220> FEATURE:
<221> NAME/KEY: gene
<222> LOCATION: (6391)..(7251)
<223> OTHER INFORMATION: Ampicillin resistance gene (complement)

<400> SEQUENCE: 27
gggggggggg ggggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
cctagttatt aatagtaatc aattacgggg tcattagttc atagcccata tatggagttc 240

```
cgcgttacat aacttacggt aaatggcccg cctggctgac cgcccaacga cccccgccca    300
ttgacgtcaa taatgacgta tgttcccata gtaacgccaa tagggacttt ccattgacgt    360
caatgggtgg actatttacg gtaaactgcc cacttggcag tacatcaagt gtatcatatg    420
ccaagtacgc cccctattga cgtcaatgac ggtaaatggc ccgcctggca ttatgcccag    480
tacatgacct tatgggactt tcctacttgg cagtacatct acgtattagt catcgctatt    540
accatggtcg aggtgagccc cacgttctgc ttcactctcc ccatctcccc cccctcccca    600
cccccaattt tgtatttatt tatttttaa ttattttgtg cagcgatggg ggcgggggg      660
gggggggggc gcgcgccagg cggggcgggg cggggcgagg ggcggggcgg ggcgaggcgg    720
agaggtgcgg cggcagccaa tcagagcggc gcgctccgaa agtttccttt tatggcgagg    780
cggcggcggc ggcggcccta taaaaagcga agcgcgcggc gggcgggagt cgctgcgacg    840
ctgccttcgc cccgtgcccc gctccgccgc cgcctcgcgc cgcccgcccc ggctctgact    900
gaccgcgtta ctcccacagg tgagcgggcg ggacggccct tctcctccgg gctgtaatta    960
gcgcttggtt taatgacggc ttgtttcttt tctgtggctg cgtgaaagcc ttgaggggct   1020
ccgggagggc cctttgtgcg gggggagcgg gctcgggggg tgcgtgcgtg tgtgtgtgcg   1080
tggggagcgc cgcgtgcggc ccgcgctgcc cggcggctgt gagcgctgcg ggcgcggcgc   1140
ggggctttgt gcgctccgca gtgtgcgcga ggggagcgcg gccgggggcg gtgccccgcg   1200
gtgcgggggg ggctgcgagg ggaacaaagg ctgcgtgcgg ggtgtgtgcg tgggggggtg   1260
agcagggggt gtgggcgcgg cggtcgggct gtaacccccc cctgcacccc cctccccgag   1320
ttgctgagca cggcccggct tcgggtgcgg ggctccgtac ggggcgtggc gcggggctcg   1380
ccgtgccggg cggggggtgg cggcaggtgg gggtgccggg cggggcgggg ccgcctcggg   1440
ccggggaggg ctcgggggag gggcgcggcg gcccccggag cgccggcggc tgtcgaggcg   1500
cggcgagccg cagccattgc cttttatggt aatcgtgcga gagggcgcag ggacttcctt   1560
tgtcccaaat ctgtgcggag ccgaaatctg ggaggcgccg ccgcaccccc tctagcgggc   1620
gcggggcgaa gcggtgcggc gccggcagga aggaaatggg cggggagggc cttcgtgcgt   1680
cgccgcgccg ccgtcccctt ctccctctcc agcctcgggg ctgtccgcgg ggggacggct   1740
gccttcgggg gggacggggc agggcggggt tcggcttctg gcgtgtgacc ggcggctcta   1800
gagcctctgc taaccatgtt catgccttct tctttttcct acagctcctg ggcaacgtgc   1860
tggttattgt gctgtctcat cattttggca aagaattcct cgaagatcta ggcctgcagg   1920
atgccgtctt ctgtctcgtg gggcatcctc ctgctggcag gcctgtgctg cctggtccct   1980
gtctccctgg ctgaggatcc ccagggagat gctgcccaga agacagatac atcccaccat   2040
gatcaggatc acccaacctt caacaagatc acccccaacc tggctgagtt cgccttcagc   2100
ctataccgcc agctggcaca ccagtccaac agcaccaata tcttcttctc cccagtgagc   2160
atcgctacag cctttgcaat gctctccctg gggaccaagg ctgacactca cgatgaaatc   2220
ctggagggcc tgaatttcaa cctcacggag attccggagg ctcagatcca tgaaggcttc   2280
caggaactcc tccgtaccct caaccagcca gacagccagc tccagctgac caccggcaat   2340
ggcctgttcc tcagcgaggg cctgaagcta gtggataagt tttggagga tgttaaaaag    2400
ttgtaccact cagaagcctt cactgtcaac ttcggggaca ccgaagaggc caagaaacag   2460
atcaacgatt acgtggagaa gggtactcaa gggaaaattg tggatttggt caaggagctt   2520
gacagagaca cagtttttgc tctggtgaat tacatcttct ttaaaggcaa atgggagaga   2580
```

```
ccctttgaag tcaaggacac cgaggaagag gacttccacg tggaccaggt gaccaccgtg   2640
aaggtgccta tgatgaagcg tttaggcatg tttaacatcc agcactgtaa gaagctgtcc   2700
agctgggtgc tgctgatgaa atacctgggc aatgccaccg ccatcttctt cctgcctgat   2760
gaggggaaac tacagcacct ggaaaatgaa ctcacccacg atatcatcac caagttcctg   2820
gaaaatgaag atcgccgtag cgcttctctg cacctgccca agttaagcat caccggcacg   2880
tacgacctga agagcgtcct gggtcaactg ggcatcacta aggtcttcag caatggggct   2940
gacctctccg gggtcacaga ggaggcaccc ctgaagctct ccaaggccgt gcataaggct   3000
gtgctgacca tcgacgagaa agggactgaa gctgctgggg ccatgttttt agaggccata   3060
cccatgtcta tccccccga ggtcaagttc aacaaaccct ttgtcttctt aatgattgaa   3120
caaaatacca agtctcccct cttcatggga aaagtggtga atcccaccca aaaagagcag   3180
aagctgatca gcgaggagga cctgtagcct gcaggcgccg gcgaccggtg ctagccctgg   3240
aggcttgctg aaggctgtat gctgtaagct ggcagacctt ctgtcgtttt ggccactgac   3300
tgacgacaga agctgccagc ttacaggaca caaggcctgt tactagcact cacatggaac   3360
aaatggccac cggtatgcat cctggaggct tgctgaaggc tgtatgctga atgtaagctg   3420
gcagaccttc gttttggcca ctgactgacg aaggtctcag cttacattca ggacacaagg   3480
cctgttacta gcactcacat ggaacaaatg gccgctagct cgcgacctgg aggcttgctg   3540
aaggctgtat gctgataggt tccagtaatg gacaggtttt ggccactgac tgacctgtcc   3600
atctggaacc tatcaggaca caaggcctgt tactagcact cacatggaac aaatggcctc   3660
gcgatgcatc tagagcggcc gcggggatcc agacatgata agatacattg atgagtttgg   3720
acaaaccaca actagaatgc agtgaaaaaa atgctttatt tgtgaaattt gtgatgctat   3780
tgctttattt gtaaccatta taagctgcaa taaacaagtt aacaacaaca attgcattca   3840
ttttatgttt caggttcagg gggaggtgtg ggaggttttt tagtcgacct cgagcagtgt   3900
ggttttgcaa gaggaagcaa aaagcctctc cacccaggcc tggaatgttt ccacccaagt   3960
cgaaggcagt gtggttttgc aagaggaagc aaaaagcctc tccacccagg cctggaatgt   4020
ttccacccaa tgtcgagcaa ccccgcccag cgtcttgtca ttggcgaatt cgaacacgca   4080
gatgcagtcg gggcggcgcg gtcccaggtc cacttcgcat attaaggtga cgcgtgtggc   4140
ctcgaacacc gagcgaccct gcagccaata tgggatcggc cattgaacaa gatggattgc   4200
acgcaggttc tccggccgct tgggtggaga ggctattcgg ctatgactgg gcacaacaga   4260
caatcggctg ctctgatgcc gccgtgttcc ggctgtcagc gcaggggcgc ccggttcttt   4320
ttgtcaagac cgacctgtcc ggtgccctga atgaactgca ggacgaggca gcgcggctat   4380
cgtggctggc cacgacgggc gttccttgcg cagctgtgct cgacgttgtc actgaagcgg   4440
gaagggactg gctgctattg ggcgaagtgc cggggcagga tctcctgtca tctcaccttg   4500
ctcctgccga gaaagtatcc atcatggctg atgcaatgcg gcggctgcat acgcttgatc   4560
cggctacctg cccattcgac caccaagcga aacatcgcat cgagcgagca cgtactcgga   4620
tggaagccgg tcttgtcgat caggatgatc tggacgaaga gcatcagggg ctcgcgccag   4680
ccgaactgtt cgccaggctc aaggcgcgca tgcccgacgg cgaggatctc gtcgtgaccc   4740
atggcgatgc ctgcttgccg aatatcatgg tggaaaatgg ccgcttttct ggattcatcg   4800
actgtggccg gctgggtgtg gcggaccgct atcaggacat agcgttggct acccgtgata   4860
ttgctgaaga gcttggcggc gaatgggctg accgcttcct cgtgctttac ggtatcgccg   4920
ctcccgattc gcagcgcatc gccttctatc gccttcttga cgagttcttc tgaggggatc   4980
```

```
cgtcgactag agctcgctga tcagcctcga ctgtgccttc tagttgccag ccatctgttg   5040
tttgcccctc ccccgtgcct tccttgaccc tggaaggtgc cactcccact gtcctttcct   5100
aataaaatga ggaaattgca tcgcattgtc tgagtaggtg tcattctatt ctggggggtg   5160
gggtggggca ggacagcaag ggggaggatt gggaagacaa tagcaggcat gctggggaga   5220
gatctaggaa cccctagtga tggagttggc cactccctct ctgcgcgctc gctcgctcac   5280
tgaggccgcc cgggcaaagc ccgggcgtcg ggcgaccttt ggtcgcccgg cctcagtgag   5340
cgagcgagcg cgcagagagg gagtggccaa cccccccccc cccccccctg cagccctgca   5400
ttaatgaatc ggccaacgcg cggggagagg cggtttgcgt attgggcgct cttccgcttc   5460
ctcgctcact gactcgctgc gctcggtcgt tcggctgcgg cgagcggtat cagctcactc   5520
aaaggcggta atacggttat ccacagaatc aggggataac gcaggaaaga acatgtgagc   5580
aaaaggccag caaaaggcca ggaaccgtaa aaaggccgcg ttgctggcgt ttttccatag   5640
gctccgcccc cctgacgagc atcacaaaaa tcgacgctca agtcagaggt ggcgaaaccc   5700
gacaggacta taaagatacc aggcgtttcc ccctggaagc tccctcgtgc gctctcctgt   5760
tccgaccctg ccgcttaccg gatacctgtc cgcctttctc ccttcgggaa gcgtggcgct   5820
ttctcaatgc tcacgctgta ggtatctcag ttcggtgtag gtcgttcgct ccaagctggg   5880
ctgtgtgcac gaaccccccg ttcagcccga ccgctgcgcc ttatccggta actatcgtct   5940
tgagtccaac ccggtaagac acgacttatc gccactggca gcagccactg gtaacaggat   6000
tagcagagcg aggtatgtag gcggtgctac agagttcttg aagtggtggc ctaactacgg   6060
ctacactaga aggacagtat ttggtatctg cgctctgctg aagccagtta ccttcggaaa   6120
aagagttggt agctcttgat ccggcaaaca aaccaccgct ggtagcggtg gtttttttgt   6180
ttgcaagcag cagattacgc gcagaaaaaa aggatctcaa gaagatcctt tgatcttttc   6240
tacggggtct gacgctcagt ggaacgaaaa ctcacgttaa gggattttgg tcatgagatt   6300
atcaaaaagg atcttcacct agatcctttt aaattaaaaa tgaagtttta aatcaatcta   6360
aagtatatat gagtaaactt ggtctgacag ttaccaatgc ttaatcagtg aggcacctat   6420
ctcagcgatc tgtctatttc gttcatccat agttgcctga ctccccgtcg tgtagataac   6480
tacgatacgg gagggcttac catctggccc cagtgctgca atgataccgc gagacccacg   6540
ctcaccggct ccagatttat cagcaataaa ccagccagcc ggaagggccg agcgcagaag   6600
tggtcctgca actttatccg cctccatcca gtctattaat tgttgccggg aagctagagt   6660
aagtagttcg ccagttaata gtttgcgcaa cgttgttgcc attgctacag gcatcgtggt   6720
gtcacgctcg tcgtttggta tggcttcatt cagctccggt tcccaacgat caaggcgagt   6780
tacatgatcc cccatgttgt gcaaaaaagc ggttagctcc ttcggtcctc cgatcgttgt   6840
cagaagtaag ttggccgcag tgttatcact catggttatg gcagcactgc ataattctct   6900
tactgtcatg ccatccgtaa gatgcttttc tgtgactggt gagtactcaa ccaagtcatt   6960
ctgagaatag tgtatgcggc gaccgagttg ctcttgcccg gcgtcaatac gggataatac   7020
cgcgccacat agcagaactt taaaagtgct catcattgga aaacgttctt cggggcgaaa   7080
actctcaagg atcttaccgc tgttgagatc cagttcgatg taacccactc gtgcacccaa   7140
ctgatcttca gcatctttta ctttcaccag cgtttctggg tgagcaaaaa caggaaggca   7200
aaatgccgca aaaaagggaa taagggcgac acggaaatgt tgaatactca tactcttcct   7260
ttttcaatat tattgaagca tttatcaggg ttattgtctc atgagcggat acatatttga   7320
```

```
atgtatttag aaaaataaac aaataggggt tccgcgcaca tttccccgaa aagtgccacc   7380

tgacgtctaa gaaaccatta ttatcatgac attaacctat aaaaataggc gtatcacgag   7440

gccctttcgt ctcgcgcgtt tcggtgatga cggtgaaaac ctctgacaca tgcagctccc   7500

ggagacggtc acagcttgtc tgtaagcgga tgccgggagc agacaagccc gtcagggcgc   7560

gtcagcgggt gttggcgggt gtcggggctg gcttaactat gcggcatcag agcagattgt   7620

actgagagtg caccatatgc ggtgtgaaat accgcacaga tgcgtaagga gaaaataccg   7680

catcaggaaa ttgtaaacgt taatattttg ttaaaattcg cgttaaattt ttgttaaatc   7740

agctcatttt ttaaccaata ggccgaaatc ggcaaaatcc cttataaatc aaaagaatag   7800

accgagatag ggttgagtgt tgttccagtt tggaacaaga gtccactatt aaagaacgtg   7860

gactccaacg tcaaagggcg aaaaaccgtc tatcagggcg atggcccact acgtgaacca   7920

tcaccctaat caagtttttt ggggtcgagg tgccgtaaag cactaaatcg gaaccctaaa   7980

gggagccccc gatttagagc ttgacgggga aagccggcga acgtggcgag aaaggaaggg   8040

aagaaagcga aaggagcggg cgctagggcg ctggcaagtg tagcggtcac gctgcgcgta   8100

accaccacac ccgccgcgct taatgcgccg ctacagggcg cgtcgcgcca ttcgccattc   8160

aggctacgca actgttggga agggcgatcg gtgcgggcct cttcgctatt acgccaggct   8220

gca                                                                 8223
```

<210> SEQ ID NO 28
<211> LENGTH: 8360
<212> TYPE: DNA
<213> ORGANISM: Artificial Sequence
<220> FEATURE:
<223> OTHER INFORMATION: Double-6XmiR-CB-AAT
<220> FEATURE:
<221> NAME/KEY: misc_feature
<222> LOCATION: (17)..(163)
<223> OTHER INFORMATION: Inverted terminal repeats (ITR)
<220> FEATURE:
<221> NAME/KEY: enhancer
<222> LOCATION: (182)..(548)
<223> OTHER INFORMATION: Enhancer
<220> FEATURE:
<221> NAME/KEY: promoter
<222> LOCATION: (549)..(1482)
<223> OTHER INFORMATION: Chicken beta actin promoter
<220> FEATURE:
<221> NAME/KEY: Intron
<222> LOCATION: (826)..(1482)
<223> OTHER INFORMATION: Intron
<220> FEATURE:
<221> NAME/KEY: misc_feature
<222> LOCATION: (1503)..(1529)
<223> OTHER INFORMATION: 5' miR
<220> FEATURE:
<221> NAME/KEY: misc_feature
<222> LOCATION: (1530)..(1550)
<223> OTHER INFORMATION: Antisense 901
<220> FEATURE:
<221> NAME/KEY: misc_feature
<222> LOCATION: (1570)..(1588)
<223> OTHER INFORMATION: Sense delta 2
<220> FEATURE:
<221> NAME/KEY: misc_feature
<222> LOCATION: (1593)..(1633)
<223> OTHER INFORMATION: 3' miR
<220> FEATURE:
<221> NAME/KEY: misc_feature
<222> LOCATION: (1646)..(1674)
<223> OTHER INFORMATION: 5' miR
<220> FEATURE:
<221> NAME/KEY: misc_feature
<222> LOCATION: (1675)..(1695)
<223> OTHER INFORMATION: Antisense 914

<220> FEATURE:
<221> NAME/KEY: misc_feature
<222> LOCATION: (1715)..(1733)
<223> OTHER INFORMATION: Sense delta 2
<220> FEATURE:
<221> NAME/KEY: misc_feature
<222> LOCATION: (1738)..(1778)
<223> OTHER INFORMATION: 3' miR
<220> FEATURE:
<221> NAME/KEY: misc_feature
<222> LOCATION: (1791)..(1819)
<223> OTHER INFORMATION: 5' miR
<220> FEATURE:
<221> NAME/KEY: misc_feature
<222> LOCATION: (1820)..(1840)
<223> OTHER INFORMATION: Antisense 943
<220> FEATURE:
<221> NAME/KEY: misc_feature
<222> LOCATION: (1860)..(1878)
<223> OTHER INFORMATION: Sense delta 2
<220> FEATURE:
<221> NAME/KEY: misc_feature
<222> LOCATION: (1883)..(1923)
<223> OTHER INFORMATION: 3' miR
<220> FEATURE:
<221> NAME/KEY: misc_feature
<222> LOCATION: (1936)..(2035)
<223> OTHER INFORMATION: Globin
<220> FEATURE:
<221> NAME/KEY: gene
<222> LOCATION: (2058)..(3311)
<223> OTHER INFORMATION: Hardened alpha-1 antitrypsin (AAT)
<220> FEATURE:
<221> NAME/KEY: misc_signal
<222> LOCATION: (3312)..(3341)
<223> OTHER INFORMATION: Cmyc-tag
<220> FEATURE:
<221> NAME/KEY: misc_feature
<222> LOCATION: (3374)..(3401)
<223> OTHER INFORMATION: 5' miR
<220> FEATURE:
<221> NAME/KEY: misc_feature
<222> LOCATION: (3402)..(3422)
<223> OTHER INFORMATION: Antisense 901
<220> FEATURE:
<221> NAME/KEY: misc_feature
<222> LOCATION: (3442)..(3460)
<223> OTHER INFORMATION: Sense delta 2
<220> FEATURE:
<221> NAME/KEY: misc_feature
<222> LOCATION: (3465)..(3505)
<223> OTHER INFORMATION: 3' miR
<220> FEATURE:
<221> NAME/KEY: misc_feature
<222> LOCATION: (3518)..(3546)
<223> OTHER INFORMATION: 5' miR
<220> FEATURE:
<221> NAME/KEY: misc_feature
<222> LOCATION: (3547)..(3567)
<223> OTHER INFORMATION: Antisense 914
<220> FEATURE:
<221> NAME/KEY: misc_feature
<222> LOCATION: (3587)..(3605)
<223> OTHER INFORMATION: Sense delta 2
<220> FEATURE:
<221> NAME/KEY: misc_feature
<222> LOCATION: (3610)..(3650)
<223> OTHER INFORMATION: 3' miR
<220> FEATURE:
<221> NAME/KEY: misc_feature
<222> LOCATION: (3663)..(3691)
<223> OTHER INFORMATION: 5' miR
<220> FEATURE:
<221> NAME/KEY: misc_feature
<222> LOCATION: (3692)..(3712)
<223> OTHER INFORMATION: Antisense 943
<220> FEATURE:
<221> NAME/KEY: misc_feature
<222> LOCATION: (3732)..(3750)

<223> OTHER INFORMATION: Sense delta 2
<220> FEATURE:
<221> NAME/KEY: misc_feature
<222> LOCATION: (3755)..(3795)
<223> OTHER INFORMATION: 3' miR
<220> FEATURE:
<221> NAME/KEY: polyA_signal
<222> LOCATION: (3814)..(4026)
<223> OTHER INFORMATION: polyA tail
<220> FEATURE:
<221> NAME/KEY: promoter
<222> LOCATION: (4167)..(4295)
<223> OTHER INFORMATION: thymidine kinase promoter (Tkp)
<220> FEATURE:
<221> NAME/KEY: gene
<222> LOCATION: (4307)..(5110)
<223> OTHER INFORMATION: Neomycin resistance gene
<220> FEATURE:
<221> NAME/KEY: misc_feature
<222> LOCATION: (5363)..(5508)
<223> OTHER INFORMATION: Inverted terminal repeats (ITR)
<220> FEATURE:
<221> NAME/KEY: gene
<222> LOCATION: (6528)..(7388)
<223> OTHER INFORMATION: Ampicillin resistance gene (complement)

<400> SEQUENCE: 28
gggggggggg gggggggtt ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctagatctg aattcggtac 180
cctagttatt aatagtaatc aattacgggg tcattagttc atagcccata tatggagttc 240
cgcgttacat aacttacggt aaatggcccg cctggctgac cgcccaacga cccccgccca 300
ttgacgtcaa taatgacgta tgttcccata gtaacgccaa tagggacttt ccattgacgt 360
caatgggtgg actatttacg gtaaactgcc cacttggcag tacatcaagt gtatcatatg 420
ccaagtacgc cccctattga cgtcaatgac ggtaaatggc ccgcctggca ttatgcccag 480
tacatgacct tatgggactt tcctacttgg cagtacatct acgtattagt catcgctatt 540
accatggtcg aggtgagccc cacgttctgc ttcactctcc ccatctcccc cccctcccca 600
cccccaattt tgtatttatt tatttttaa ttattttgtg cagcgatggg ggcggggggg 660
gggggggggc gcgcgccagg cggggcgggg cggggcgagg ggcggggcgg ggcgaggcgg 720
agaggtgcgg cggcagccaa tcagagcggc gcgctccgaa agtttccttt tatggcgagg 780
cggcggcggc ggcggcccta taaaaagcga agcgcgcggc gggcgggagt cgctgcgacg 840
ctgccttcgc cccgtgcccc gctccgccgc cgcctcgcgc cgcccgcccc ggctctgact 900
gaccgcgtta ctcccacagg tgagcgggcg ggacggccct tctcctccgg gctgtaatta 960
gcgcttggtt taatgacggc ttgtttcttt tctgtggctg cgtgaaagcc ttgaggggct 1020
ccgggagggc cctttgtgcg gggggggagcg gctcgggggg tgcgtgcgtg tgtgtgtgcg 1080
tggggagcgc cgcgtgcggc ccgcgctgcc cggcggctgt gagcgctgcg ggcgcggcgc 1140
ggggctttgt gcgctccgca gtgtgcgcga ggggagcgcg gccgggggcg gtgccccgcg 1200
gtgcgggggg ggctgcgagg ggaacaaagg ctgcgtgcgg ggtgtgtgcg tgggggggtg 1260
agcagggggt gtgggcgcgg cggtcgggct gtaacccccc cctgcacccc cctccccgag 1320
ttgctgagca cggcccggct tcgggtgcgg ggctccgtac ggggcgtggc gcggggctcg 1380
ccgtgccggg cgggggggtgg cggcaggtgg gggtgccggg cggggcgggg ccgcctcggg 1440
ccggggaggg ctcgggggag ggcgcggcg gccccggag cgccggcgac cggtgctagc 1500
cctggaggct tgctgaaggc tgtatgctgt aagctggcag accttctgtc gttttggcca 1560

```
ctgactgacg acagaagctg ccagcttaca ggacacaagg cctgttacta gcactcacat   1620
ggaacaaatg gccaccggta tgcatcctgg aggcttgctg aaggctgtat gctgaatgta   1680
agctggcaga ccttcgtttt ggccactgac tgacgaaggt ctcagcttac attcaggaca   1740
caaggcctgt tactagcact cacatggaac aaatggccgc tagctcgcga cctggaggct   1800
tgctgaaggc tgtatgctga taggttccag taatggacag gttttggcca ctgactgacc   1860
tgtccatctg gaacctatca ggacacaagg cctgttacta gcactcacat ggaacaaatg   1920
gcctcgcgat gcatctagag cctctgctaa ccatgttcat gccttcttct ttttcctaca   1980
gctcctgggc aacgtgctgg ttattgtgct gtctcatcat tttggcaaag aattcctcga   2040
agatctaggc ctgcaggatg ccgtcttctg tctcgtgggg catcctcctg ctggcaggcc   2100
tgtgctgcct ggtccctgtc tccctggctg aggatcccca gggagatgct gcccagaaga   2160
cagatacatc ccaccatgat caggatcacc caaccttcaa caagatcacc cccaacctgg   2220
ctgagttcgc cttcagccta taccgccagc tggcacacca gtccaacagc accaatatct   2280
tcttctcccc agtgagcatc gctacagcct ttgcaatgct ctccctgggg accaaggctg   2340
acactcacga tgaaatcctg gagggcctga atttcaacct cacggagatt ccggaggctc   2400
agatccatga aggcttccag gaactcctcc gtaccctcaa ccagccagac agccagctcc   2460
agctgaccac cggcaatggc ctgttcctca gcgagggcct gaagctagtg gataagtttt   2520
tggaggatgt taaaaagttg taccactcag aagccttcac tgtcaacttc ggggacaccg   2580
aagaggccaa gaaacagatc aacgattacg tggagaaggg tactcaaggg aaaattgtgg   2640
atttggtcaa ggagcttgac agagacacag tttttgctct ggtgaattac atcttcttta   2700
aaggcaaatg ggagagaccc tttgaagtca aggacaccga ggaagaggac ttccacgtgg   2760
accaggtgac caccgtgaag gtgcctatga tgaagcgttt aggcatgttt aacatccagc   2820
actgtaagaa gctgtccagc tgggtgctgc tgatgaaata cctgggcaat gccaccgcca   2880
tcttcttcct gcctgatgag gggaaactac agcacctgga aaatgaactc acccacgata   2940
tcatcaccaa gttcctggaa aatgaagatc gccgtagcgc ttctctgcac ctgcccaagt   3000
taagcatcac cggcacgtac gacctgaaga gcgtcctggg tcaactgggc atcactaagg   3060
tcttcagcaa tggggctgac ctctccgggg tcacagagga ggcacccctg aagctctcca   3120
aggccgtgca taaggctgtg ctgaccatcg acgagaaagg gactgaagct gctggggcca   3180
tgtttttaga ggccataccc atgtctatcc cccccgaggt caagttcaac aaaccctttg   3240
tcttcttaat gattgaacaa aataccaagt ctcccctctt catgggaaaa gtggtgaatc   3300
ccacccaaaa agagcagaag ctgatcagcg aggaggacct gtagcctgca ggcgccggcg   3360
accggtgcta gccctggagg cttgctgaag gctgtatgct gtaagctggc agaccttctg   3420
tcgttttggc cactgactga cgacagaagc tgccagctta caggacacaa ggcctgttac   3480
tagcactcac atggaacaaa tggccaccgg tatgcatcct ggaggcttgc tgaaggctgt   3540
atgctgaatg taagctggca gaccttcgtt ttggccactg actgacgaag gtctcagctt   3600
acattcagga cacaaggcct gttactagca ctcacatgga acaaatggcc gctagctcgc   3660
gacctggagg cttgctgaag gctgtatgct gataggttcc agtaatggac aggttttggc   3720
cactgactga cctgtccatc tggaacctat caggacacaa ggcctgttac tagcactcac   3780
atggaacaaa tggcctcgcg atgcatctag agcggccgcg gggatccaga catgataaga   3840
tacattgatg agtttggaca aaccacaact agaatgcagt gaaaaaaatg ctttatttgt   3900
```

-continued

```
gaaatttgtg atgctattgc tttatttgta accattataa gctgcaataa acaagttaac   3960
aacaacaatt gcattcattt tatgtttcag gttcaggggg aggtgtggga ggttttttag   4020
tcgacctcga gcagtgtggt tttgcaagag gaagcaaaaa gcctctccac ccaggcctgg   4080
aatgtttcca cccaagtcga aggcagtgtg gttttgcaag aggaagcaaa aagcctctcc   4140
acccaggcct ggaatgtttc cacccaatgt cgagcaaccc cgcccagcgt cttgtcattg   4200
gcgaattcga acacgcagat gcagtcgggg cggcgcggtc ccaggtccac ttcgcatatt   4260
aaggtgacgc gtgtggcctc gaacaccgag cgaccctgca gccaatatgg gatcggccat   4320
tgaacaagat ggattgcacg caggttctcc ggccgcttgg gtggagaggc tattcggcta   4380
tgactgggca caacagacaa tcggctgctc tgatgccgcc gtgttccggc tgtcagcgca   4440
ggggcgcccg gttctttttg tcaagaccga cctgtccggt gccctgaatg aactgcagga   4500
cgaggcagcg cggctatcgt ggctggccac gacgggcgtt ccttgcgcag ctgtgctcga   4560
cgttgtcact gaagcgggaa gggactggct gctattgggc gaagtgccgg ggcaggatct   4620
cctgtcatct caccttgctc ctgccgagaa agtatccatc atggctgatg caatgcggcg   4680
gctgcatacg cttgatccgg ctacctgccc attcgaccac caagcgaaac atcgcatcga   4740
gcgagcacgt actcggatgg aagccggtct tgtcgatcag gatgatctgg acgaagagca   4800
tcaggggctc gcgccagccg aactgttcgc caggctcaag gcgcgcatgc ccgacggcga   4860
ggatctcgtc gtgacccatg gcgatgcctg cttgccgaat atcatggtgg aaaatggccg   4920
cttttctgga ttcatcgact gtggccggct gggtgtggcg gaccgctatc aggacatagc   4980
gttggctacc cgtgatattg ctgaagagct tggcggcgaa tgggctgacc gcttcctcgt   5040
gctttacggt atcgccgctc ccgattcgca gcgcatcgcc ttctatcgcc ttcttgacga   5100
gttcttctga ggggatccgt cgactagagc tcgctgatca gcctcgactg tgccttctag   5160
ttgccagcca tctgttgttt gcccctcccc cgtgccttcc ttgaccctgg aaggtgccac   5220
tcccactgtc ctttcctaat aaaatgagga aattgcatcg cattgtctga gtaggtgtca   5280
ttctattctg gggggtgggg tggggcagga cagcaagggg gaggattggg aagacaatag   5340
caggcatgct ggggagagat ctaggaaccc ctagtgatgg agttggccac tccctctctg   5400
cgcgctcgct cgctcactga ggccgcccgg gcaaagcccg ggcgtcgggc gacctttggt   5460
cgcccggcct cagtgagcga gcgagcgcgc agagagggag tggccaaccc cccccccccc   5520
cccctgcag ccctgcatta atgaatcggc caacgcgcgg ggagaggcgg tttgcgtatt   5580
gggcgctctt ccgcttcctc gctcactgac tcgctgcgct cggtcgttcg gctgcggcga   5640
gcggtatcag ctcactcaaa ggcggtaata cggttatcca cagaatcagg ggataacgca   5700
ggaaagaaca tgtgagcaaa aggccagcaa aaggccagga accgtaaaaa ggccgcgttg   5760
ctggcgtttt tccataggct ccgcccccct gacgagcatc acaaaaatcg acgctcaagt   5820
cagaggtggc gaaacccgac aggactataa agataccagg cgtttccccc tggaagctcc   5880
ctcgtgcgct ctcctgttcc gaccctgccg cttaccggat acctgtccgc ctttctccct   5940
tcgggaagcg tggcgctttc tcaatgctca cgctgtaggt atctcagttc ggtgtaggtc   6000
gttcgctcca agctgggctg tgtgcacgaa ccccccgttc agcccgaccg ctgcgcctta   6060
tccggtaact atcgtcttga gtccaacccg gtaagacacg acttatcgcc actggcagca   6120
gccactggta acaggattag cagagcgagg tatgtaggcg gtgctacaga gttcttgaag   6180
tggtggccta actacggcta cactagaagg acagtatttg gtatctgcgc tctgctgaag   6240
ccagttacct tcggaaaaag agttggtagc tcttgatccg gcaaacaaac caccgctggt   6300
```

```
agcggtggtt tttttgtttg caagcagcag attacgcgca gaaaaaaagg atctcaagaa   6360

gatcctttga tcttttctac ggggtctgac gctcagtgga acgaaaactc acgttaaggg   6420

attttggtca tgagattatc aaaaaggatc ttcacctaga tccttttaaa ttaaaaatga   6480

agttttaaat caatctaaag tatatatgag taaacttggt ctgacagtta ccaatgctta   6540

atcagtgagg cacctatctc agcgatctgt ctatttcgtt catccatagt tgcctgactc   6600

cccgtcgtgt agataactac gatacgggag ggcttaccat ctggccccag tgctgcaatg   6660

ataccgcgag acccacgctc accggctcca gatttatcag caataaacca gccagccgga   6720

agggccgagc gcagaagtgg tcctgcaact ttatccgcct ccatccagtc tattaattgt   6780

tgccgggaag ctagagtaag tagttcgcca gttaatagtt tgcgcaacgt tgttgccatt   6840

gctacaggca tcgtggtgtc acgctcgtcg tttggtatgg cttcattcag ctccggttcc   6900

caacgatcaa ggcgagttac atgatccccc atgttgtgca aaaaagcggt tagctccttc   6960

ggtcctccga tcgttgtcag aagtaagttg gccgcagtgt tatcactcat ggttatggca   7020

gcactgcata attctcttac tgtcatgcca tccgtaagat gcttttctgt gactggtgag   7080

tactcaacca agtcattctg agaatagtgt atgcggcgac cgagttgctc ttgcccggcg   7140

tcaatacggg ataataccgc gccacatagc agaactttaa aagtgctcat cattggaaaa   7200

cgttcttcgg ggcgaaaact ctcaaggatc ttaccgctgt tgagatccag ttcgatgtaa   7260

cccactcgtg cacccaactg atcttcagca tcttttactt tcaccagcgt ttctgggtga   7320

gcaaaaacag gaaggcaaaa tgccgcaaaa aagggaataa gggcgacacg gaaatgttga   7380

atactcatac tcttcctttt tcaatattat tgaagcattt atcagggtta ttgtctcatg   7440

agcggataca tatttgaatg tatttagaaa aataaacaaa taggggttcc gcgcacattt   7500

ccccgaaaag tgccacctga cgtctaagaa accattatta tcatgacatt aacctataaa   7560

aataggcgta tcacgaggcc ctttcgtctc gcgcgtttcg gtgatgacgg tgaaaacctc   7620

tgacacatgc agctcccgga gacggtcaca gcttgtctgt aagcggatgc cgggagcaga   7680

caagcccgtc agggcgcgtc agcgggtgtt ggcgggtgtc ggggctggct taactatgcg   7740

gcatcagagc agattgtact gagagtgcac catatgcggt gtgaaatacc gcacagatgc   7800

gtaaggagaa aataccgcat caggaaattg taaacgttaa tattttgtta aaattcgcgt   7860

taaatttttg ttaaatcagc tcatttttta accaataggc cgaaatcggc aaaatccctt   7920

ataaatcaaa agaatagacc gagatagggt tgagtgttgt tccagtttgg aacaagagtc   7980

cactattaaa gaacgtggac tccaacgtca aagggcgaaa aaccgtctat cagggcgatg   8040

gcccactacg tgaaccatca ccctaatcaa gttttttggg gtcgaggtgc cgtaaagcac   8100

taaatcggaa ccctaaaggg agcccccgat ttagagcttg acggggaaag ccggcgaacg   8160

tggcgagaaa ggaagggaag aaagcgaaag gagcgggcgc tagggcgctg gcaagtgtag   8220

cggtcacgct gcgcgtaacc accacacccg ccgcgcttaa tgcgccgcta cagggcgcgt   8280

cgcgccattc gccattcagg ctacgcaact gttgggaagg gcgatcggtg cgggcctctt   8340

cgctattacg ccaggctgca                                                8360
```

<210> SEQ ID NO 29
<211> LENGTH: 18
<212> TYPE: DNA
<213> ORGANISM: Artificial Sequence
<220> FEATURE:
<223> OTHER INFORMATION: Forward primer for PIM and PIZ

```
<400> SEQUENCE: 29

ccaaggccgt gcataagg                                                     18


<210> SEQ ID NO 30
<211> LENGTH: 18
<212> TYPE: DNA
<213> ORGANISM: Artificial Sequence
<220> FEATURE:
<223> OTHER INFORMATION: Reverse primer for PIM and PIZ

<400> SEQUENCE: 30

ggccccagca gcttcagt                                                     18


<210> SEQ ID NO 31
<211> LENGTH: 18
<212> TYPE: DNA
<213> ORGANISM: Artificial Sequence
<220> FEATURE:
<223> OTHER INFORMATION: Probe for PIZ (mutant AAT)
<220> FEATURE:
<221> NAME/KEY: misc_signal
<222> LOCATION: (1)..(1)
<223> OTHER INFORMATION: 6FAM probe molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_signal
<222> LOCATION: (18)..(18)
<223> OTHER INFORMATION: MGBNFQ probe molecule
<220> FEATURE:
<221> NAME/KEY: misc_feature
<222> LOCATION: (18)..(18)
<223> OTHER INFORMATION: n is a, c, g, or t

<400> SEQUENCE: 31

nctgaccatc gacaagan                                                     18


<210> SEQ ID NO 32
<211> LENGTH: 18
<212> TYPE: DNA
<213> ORGANISM: Artificial Sequence
<220> FEATURE:
<223> OTHER INFORMATION: Probe for PIM (wild-type AAT)
<220> FEATURE:
<221> NAME/KEY: misc_signal
<222> LOCATION: (1)..(1)
<223> OTHER INFORMATION: 6FAM probe molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_signal
<222> LOCATION: (18)..(18)
<223> OTHER INFORMATION: MGBNFQ probe molecule
<220> FEATURE:
<221> NAME/KEY: misc_feature
<222> LOCATION: (18)..(18)
<223> OTHER INFORMATION: n is a, c, g, or t

<400> SEQUENCE: 32

nctgaccatc gacgagan                                                     18
```

RAAV-BASED COMPOSITIONS AND METHODS FOR TREATING ALPHA-1 ANTI-TRYPSIN DEFICIENCIES

RELATED APPLICATIONS

This application is a National State Application PCT/US2012/034446, field on Apr. 20, 2012, and entitled "RAAV-BASED COMPOSITIONS AND METHODS FOR TREATING ALPHA-1 ANTI-TRYPSIN DEFICIENCIES," which claims priority under 35 U.S.C. §119(e) to U.S. Provisional Application Ser. No. 61/477,671, entitled "RAAV-BASED COMPOSITIONS AND METHODS FOR TREATING ALPHA-1 ANTI-TRYPSIN DEFICIENCIES" filed on Apr. 21, 2011, which is herein incorporated by reference in its entirety.

FEDERALLY SPONSORED RESEARCH

This invention was made with Government support from the National Institutes of Health under Grant Numbers HL69877 and P30 DK 32520. The Government has certain rights in the invention.

FIELD OF THE INVENTION

The invention relates to methods and compositions for treating genetic disease using rAAV-based vectors.

BACKGROUND OF THE INVENTION

Numerous diseases are associated with inherited or somatic mutations. In many cases, these mutations are present in the transcript region of genes, the products of which control important physiological functions including, for example, gene expression, cell signaling, tissue structure, and the metabolism and catabolism of various biomolecules. Mutations in these genes, which are often only single nucleotide changes (e.g., non-sense mutations, missense mutations), can have negative effects on the expression, stability and/or function of the gene product resulting in alterations in one or more physiological functions.

A number of different mutations have been identified in the Alpha-1 antitrypsin (AAT) gene. AAT is one of the primary circulating serum anti-proteases in humans. AAT inhibits a variety of serine proteinases, with neutrophil elastase being one of the most physiologically important, as well as inhibiting a number of metalloproteinases and other pro-inflammatory and pro-apoptotic molecules. AAT is normally produced within hepatocytes and macrophages, where hepatocyte-derived AAT forms the bulk of the physiologic reserve of AAT.

Approximately 4% of the North American and Northern European populations possess at least one copy of a mutant allele, known as PI*Z (Z-AAT) which results from a single amino acid substitution of lysine for glutamate at position 342 in the mature protein (position 366 in the precursor protein). In the homozygous state, this mutation leads to severe deficiency of AAT, and can result in two distinct pathologic states: a lung disease which is primarily due to the loss of antiprotease function, and a liver disease (present to a significant degree in approximately 10-15% of patients) due to a toxic gain of function of the Z-AAT mutant protein.

Investigational clinical gene therapy products for gene augmentation of AAT have been developed as potential treatments for lung disease using the recombinant adeno-associated viral (rAAV) vectors. Researchers have also applied genetic technologies in an effort to down-regulate the levels of AAT mRNA. One approach was to utilize hammerhead ribozymes designed to cleave AAT mRNA at a specific site. Another approach involves the use of RNA interference to decrease levels of the mutant mRNA transcript.

SUMMARY OF THE INVENTION

Aspects of the invention relate to improved gene therapy-based methods for treating genetic disease. Some aspects of the invention relate to improved gene therapy compositions and related methodology for treating lung disease and/or liver disease using the recombinant adeno-associated viral vectors. In some embodiments, the methods utilize rAAV (e.g., rAAV9, rAAV2, rAAV1) based vectors for augmenting AAT expression. In some embodiments, compositions and methods are provided for decreasing the expression of Pi*Z mutant AAT protein. In such embodiments, the compositions and methods are useful for halting and/or ameliorating hepatocellular damage and other tissue damage associated with the mutant AAT.

According to some aspects of the invention, the compositions and methods are useful for knocking down PiZ protein while at the same time increasing levels of the M-AAT protein (the wild-type AAT protein). In some embodiments, a non-toxic dual function vector is provided that is capable of knocking-down Z-AAT while augmenting M-AAT. According to some embodiments, methods and compositions for long-term expression of therapeutic miRNAs are provided that utilize the recombinant adeno-associated virus (rAAV) platform. In some embodiments, therapeutic compositions and methods described herein take advantage of the miRNA pathway by altering the seed sequence of natural miRNAs to target the endogenous AAT gene. In some embodiments, the methods are safer and less toxic than shRNA-based approaches.

According to other aspects of the invention, rAAV-based compositions and methods are provided that simultaneously direct silencing agents to the liver to decrease Z-AAT expression and direct gene augmentation to other sites. However, in some embodiments, the liver is an optimal target tissue for augmentation. In some embodiments, a miRNA-based approach is provided to stably down-regulate Z-AAT within hepatocytes. In some embodiments, the approach allows for simultaneous M-AAT gene augmentation from the same rAAV gene delivery vector without serious perturbation of the overall hepatic miRNA profile. In some embodiments, the specific vector used is a systemically delivered rAAV9-capsid derived vector. According to some aspects of the invention, this approach has broad utility in genetic disorders stemming from dominant negative and gain of function mutations as well as for delivering artificial miRNAs to be delivered in conjunction with therapeutic genes.

According to some aspects of the invention, isolated nucleic acids are provided. In some embodiments, the isolated nucleic acids comprise (a) a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a first protein; and (b) a second region encoding an exogenous mRNA that encodes a second protein, wherein the second protein has an amino acid sequence that is at least 85% identical to the first protein, wherein the one or more first miRNAs do not comprise a nucleic acid having sufficient sequence complementary to hybridize with and inhibit expression of the exogenous mRNA, and wherein the first region is positioned within an untranslated portion of the second region. In some embodiments, the untranslated portion is an intron. In some embodiments, the first region is between the first codon of the exogenous mRNA and 1000 nucleotides upstream of the first codon.

In some embodiments, the isolated nucleic acids comprise (a) a first region encoding one or more first miRNAs comprising a nucleic acid having sufficient sequence complementary with an endogenous mRNA of a subject to hybridize with and inhibit expression of the endogenous mRNA, wherein the endogenous mRNA encodes a first protein; and (b) a second region encoding an exogenous mRNA that encodes a second protein, wherein the second protein has an amino acid sequence that is at least 85% identical to the first protein, wherein the one or more first miRNAs do not comprise a nucleic acid having sufficient sequence complementary to hybridize with and inhibit expression of the exogenous mRNA, and wherein the first region is positioned downstream of a portion of the second region encoding the poly-A tail of the exogenous mRNA.

In some embodiments, the isolated nucleic acids further comprise a third region encoding a one or more second miRNAs comprising a nucleic acid having sufficient sequence complementary to hybridize with and inhibit expression of the endogenous mRNA, wherein the third region is positioned within an untranslated portion of the second region. In some embodiments, the untranslated portion is an intron. In some embodiments, the first region is between the last codon of the exogenous mRNA and a position 1000 nucleotides downstream of the last codon. In some embodiments, the third region is between the first codon of the exogenous mRNA and a position 1000 nucleotides upstream of the first codon.

In some embodiments of the isolated nucleic acids, the first region encodes two first miRNAs. In some embodiments, the first region encodes three first miRNAs. In some embodiments, the third region encodes two second miRNAs. In some embodiments, the third region encodes three second miRNAs. In some embodiments, one or more of the first miRNAs have the same nucleic acid sequence as one or more of the second miRNAs. In some embodiments, each of the first miRNAs has the same nucleic acid sequence as one of the second miRNAs. In some embodiments, the second protein has an amino acid sequence that is at least 90% identical to the first protein. In some embodiments, the second protein has an amino acid sequence that is at least 95% identical to the first protein. In some embodiments, the second protein has an amino acid sequence that is at least 98% identical to the first protein. In some embodiments, the second protein has an amino acid sequence that is at least 99% identical to the first protein. In some embodiments, the second protein has an amino acid sequence that is 100% identical to the first protein.

In some embodiments of the isolated nucleic acids, the first protein is Alpha 1-Antitrypsin (AAT) protein. In some embodiments, the AAT protein is a human AAT protein. In some embodiments, the AAT protein has sequence as set forth in SEQ ID NO: 1 or 2 or one or more mutations thereof as identified in Table 1, e.g. SEQ ID NO: 3 or 4. In some embodiments, the first mRNA comprises a nucleic acid encoded by a sequence as set forth in SEQ ID NOS: 5-16. In some embodiments, the one or more miRNAs have a nucleic acid sequence encoded by a sequence from the group consisting of SEQ ID NOS: 17-19 and 21-23. In some embodiments of the isolated nucleic acids, the exogenous mRNA has one or more silent mutations compared with the endogenous mRNA. In some embodiments, the exogenous mRNA has a nucleic acid sequence encoded by a sequence as set forth in SEQ ID NO: 20.

In some embodiments, the isolated nucleic acids further comprise an inverted terminal repeats (ITR) of an AAV serotypes selected from the group consisting of: AAV1, AAV2, AAV5, AAV6, AAV6.2, AAV7, AAV8, AAV9, AAV10, AAV11 and variants thereof. In some embodiments, the isolated nucleic acids further comprise a promoter operably linked with the region(s) encoding the one or more first miRNAs, the exogenous mRNA, and/or the one or more second miRNAs. In certain embodiments, the promoter is a tissue-specific promoter. In certain embodiments, the promoter is a β-actin promoter.

According to some aspects of the invention, recombinant Adeno-Associated Viruses (AAVs) are provided that comprise any of the isolated nucleic acids disclosed herein. In some embodiments, the recombinant AAVs further comprise one or more capsid proteins of one or more AAV serotypes selected from the group consisting of: AAV1, AAV2, AAV3, AAV4, AAV5, AAV6, AAV7, AAV8, AAV9, AAV10, AAV11 and variants thereof.

According to some aspects of the invention, compositions are provided that comprise any of the isolated nucleic acids disclosed herein. According to some aspects of the invention, compositions are provided that comprise any of the recombinant AAVs disclosed herein. In some embodiments, the compositions further comprise a pharmaceutically acceptable carrier.

According to some aspects of the invention, kits are provided that comprise one or more containers housing a composition, isolated nucleic acid or rAAV of the invention. In some embodiments, the kits further comprise written instructions for administering an rAAV to a subject.

According to some aspects of the invention, methods are provided for expressing Alpha 1-Antitrypsin (AAT) protein in a subject. In some embodiments, the methods comprise administering to a subject an effective amount of any recombinant Adeno-Associated Virus (rAAV) disclosed herein. In some embodiments, the rAAV is administered with a pharmaceutically acceptable carrier.

In some embodiments of the methods, the subject has or suspected of having an Alpha 1-Antitrypsin deficiency. In certain embodiments, the subject has a mutation in an AAT gene. In certain embodiments, the mutation encodes a mutant AAT protein. In some embodiments, the methods further comprise determining that the subject has the mutation. In certain embodiments, the mutation is a mutation listed in Table 1. In certain embodiments, the mutation is a missense mutation. In certain embodiments, the mutation results in a glutamate to lysine substitution at amino acid position 366 according to the amino acid sequence set forth as SEQ ID NO: 3. In certain embodiments, the mutant AAT protein fails to fold properly.

In some embodiments of the methods, the effective amount of rAAV is $10^{10}$, $10^{11}$, $10^{12}$, or $10^{13}$ genome copies. In some embodiments, administering is performed intravascularly, intravenously, intrathecally, intraperatoneally, intramuscularly, subcutaneously or intranasally. In certain embodiments, administering is performed by injection into the hepatic portal vein.

In some embodiments of the methods, administering is performed ex vivo by isolating cells or tissue from a subject, contacting the cell or tissue with an effective amount of an rAAV, thereby producing transfected cells or tissue, and administering the transfected cells or tissue to the subject. In certain embodiments, the tissue is adipose tissue. In certain embodiments, the cells are stem cells derived from adipose tissue. In some embodiments, administering the transfected cells is performed intravascularly, intravenously, intrathecally, intraperatoneally, intramuscularly, subcutaneously or intranasally. In certain embodiments, administering the transfected cells is performed by transplantation of transfected cells into a target tissue. In certain embodiments, the target tissue is lung or liver In some embodiments of the methods, the subject is a mouse, a rat, a rabbit, a dog, a cat, a sheep, a pig, a non-human primate or a human. In certain embodiments, the subject is a human.

In some embodiments of the methods, after administration of the rAAV the level of expression of the first protein is determined in the subject. In some embodiments, after administration of the rAAV the level of expression of the second protein is determined in the subject. In some embodiments, administering is performed on two or more occasions. In certain embodiments, the level of the first protein and/or the level of the second protein in the subject are determined after at least one administration.

In some embodiments of the methods, the serum level of the first protein in the subject is reduced by at least 85% following administration of the rAAV. In some embodiments, the serum level of the first protein in the subject is reduced by at least 90% following administration of the rAAV. In some embodiments, the serum level of the first protein in the subject is reduced by at least 95% following administration of the rAAV. In some embodiments, the serum level of the first protein in the subject is reduced by at least 85% within 2 weeks following administration of the rAAV. In some embodiments, the serum level of the first protein in the subject is reduced by at least 90% within 2 weeks following administration of the rAAV. In some embodiments, the serum level of the first protein in the subject is reduced by at least 85% within 4 weeks of administration of the rAAV. In some embodiments, after 7 weeks of administration of the rAAV, the serum level of the first protein is at a level of at least 50% compared with the serum level of the first protein prior to administration of the rAAV. In some embodiments, after 7 weeks of administration of the rAAV, the serum level of the first protein is at a level of at least 75% compared with the serum level of the first protein prior to administration of the rAAV.

In some embodiments of the methods, after administration of the rAAV at least one clinical outcome parameter associated with the AAT deficiency is evaluated in the subject. In some embodiments, the at least one clinical outcome parameter evaluated after administration of the rAAV is compared with the at least one clinical outcome parameter determined prior to administration of the rAAV to determine effectiveness of the rAAV, wherein an improvement in the clinical outcome parameter after administration of the rAAV indicates effectiveness of the rAAV. In some embodiments, the clinical outcome parameter is selected from the group consisting of: serum levels of the first protein, serum levels of the second protein, presence of intracellular AAT globules, presence of inflammatory foci, breathing capacity, cough frequency, phlegm production, frequency of chest colds or pneumonia, and tolerance for exercise. In some embodiments, the intracellular AAT globules or inflammatory foci are evaluated in lung tissue or liver tissue.

DETAILED DESCRIPTION OF CERTAIN EMBODIMENTS OF THE INVENTION

Figure 1A:
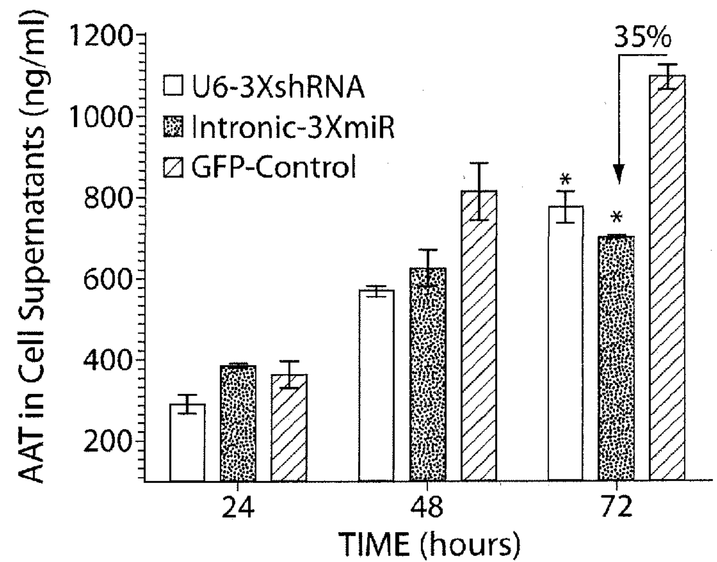
FIG. 1 Comparison of shRNA and miRNA mediated knockdown of human AAT. HEK-293 cells were contrasfected with human Z-AAT plasmid and either a plasmid expressing 3 anti-AAT shRNAs from a U6 promoter or a plasmid expressing 3 anti-AAT miRNA from a hybrid chicken beta actin promoter. (a) Culture media was harvested at 24, 48 and 72 hours and was analyzed for the AAT concentration by ELISA. (b) At 72 hours cells were harvested and lysed for AAT concentration by ELISA. *<0.05 as determined by a two-way unpaired student t-test.

Aspects of the invention relate to improved gene therapy compositions and related methods for treating Alpha-1 Antitrypsin (AAT, also sometimes called SERPINA1) deficiencies using the recombinant adeno-associated viral (rAAV) vectors. In some embodiments, a non-toxic dual function vector is provided that is capable of knocking-down mutant AAT while expressing wild-type AAT. The rAAV-based vectors and related methods provide for long-term expression of therapeutic miRNAs and expression of wild-type protein. According to other aspects, rAAV-based compositions and methods are provided that simultaneously direct silencing agents to the liver to decrease Z-AAT expression and direct gene expression to other sites (e.g., lung tissue). In some embodiments, compositions and methods are provided that are useful for treating the AAT deficiency by knocking down PiZ protein (a mutant AAT protein) while at the same time increasing levels of the M-AAT protein (the wild-type AAT protein). It will be appreciated that the rAAV-based therapeutic approaches disclosed herein can be applied to other gain-of-function or dominant-negative genetic disorders such as Huntington's disease, which previously have not been amiable to a single vector gene therapy approach.

Certain rAAV vectors provided herein incorporate miRNA sequences targeting the AAT gene while driving the expression of hardened wild-type AAT gene (a wild-type AAT gene that is not targeted by the miRNA), thus achieving concomitant mutant AAT knockdown e.g., in the liver, with increased expression of wildtype AAT. In one embodiment, transgenic mice expressing the human PiZ allele were injected with control or dual function rAAV9 vectors expressing both miRNAs and a hardened AAT gene with a cMyc tag. In this embodiment, serum PiZ levels were consistently knocked down by an average of 80% from baseline levels with the knockdown being stable and persistent over a 13 week period. In one embodiment, cohorts receiving dual function vectors exhibited knockdown of PiZ AAT while secreting increased serum levels of wild-type AAT as determined by a PiZ and PiM specific ELISAs. In this embodiment, liver histology revealed significantly decreased globular accumulation of misfolded PiZ AAT in hepatocytes along with a reduction in inflammatory infiltrates when compared to controls.

In one embodiment, global miRNA expression profiles of the liver were minimally affected by artificial miRNAs delivered via rAAV, with only a few miRNAs showing statistically significant differences. In one embodiment, a difference was seen in miR-1 which was reduced in PiZ transgenic mice receiving rAAV vectors to normal levels seen in wild-type B6 mice. In one embodiment, the levels of miR-122 were unaffected in all mice receiving rAAVs expressing miRNA targeting the AAT gene. Accordingly, in some embodiments, dual function rAAV vectors are effective at knocking down PIZ AAT while simultaneously augmenting wild-type AAT without disturbing endogenous miRNA liver profiles.

Alpha-1 Antitrypsin Deficiency

Alpha-1 antitrypsin (AAT), also known in the art as serpin peptidase inhibitor, clade A (SERPINA1), is a protein that functions as proteinase (protease) inhibitor. AAT is mainly produced in the liver, but functions in the lungs and liver, primarily. As used herein the term, "alpha-1 antitrypsin deficiency" refers to a condition resulting from a deficiency of functional AAT in a subject. In some embodiments, a subject having an AAT deficiency produces insufficient amounts of alpha-1 antitrypsin. In some embodiments, a subject having an AAT deficiency produces a mutant AAT. In some embodiments, insufficient amounts of AAT or expression of mutant AAT results in damage to a subject's lung and/or liver. In some embodiments, the AAT deficiency leads to emphysema and/or liver disease. Typically, AAT deficiencies result from one or more genetic defects in the AAT gene. The one or more defects may be present in one or more copies (e.g., alleles) of the AAT gene in a subject. Typically, AAT deficiencies are most common among Europeans and North Americans of European descent. However, AAT deficiencies may be found in subjects of other descents as well.

Subjects (e.g., adult subjects) with severe AAT deficiencies are likely to develop emphysema. Onset of emphysema often occurs before age 40 in human subjects having AAT deficiencies. Smoking can increase the risk of emphysema in subjects having AAT deficiencies. Symptoms of AAT deficiencies include shortness of breath, with and without exertion, and other symptoms commonly associated with chronic obstructive pulmonary disease (COPD). Other symptoms of AAT deficiencies include symptoms of severe liver disease (e.g., cirrhosis), unintentional weight loss, and wheezing. A physical examination may reveal a barrel-shaped chest, wheezing, or decreased breath sounds in a subject who has an AAT deficiency.

The following exemplary tests may assist with diagnosing a subject as having an AAT deficiency: an alpha-1 antitrypsin blood test, examination of arterial blood gases, a chest x-ray, a CT scan of the chest, genetic testing, and lung function test. In some cases, a subject having or suspected of having an AAT deficiency is subjected to genetic testing to detect the presence of one or more mutations in the AAT gene. In some embodiments, one or more of the mutations listed in Table 1 are detected in the subject.

In some cases, a physician may suspect that a subject has an AAT deficiency if the subject has emphysema at an early age (e.g., before the age of 45), emphysema without ever having smoked or without ever having been exposed to toxins, emphysema with a family history of an AAT deficiency, liver disease or hepatitis when no other cause can be found, liver disease or hepatitis and a family history of an AAT deficiency.

In some embodiments, alpha-1 antitrypsin deficiency can result in two distinct pathologic states: a lung disease which is primarily due to the loss of anti-protease function, and a liver disease due to a toxic gain of function of the mutant AAT protein (e.g., mutant PiZ-AAT). For example, since mutant AAT-PiZ exhibits a gain-of-function hepatocellular toxicity accumulating in the endoplasmic reticulum, therapies aimed at decreasing AAT-PiZ mRNA levels may ameliorate or even reverse the liver pathology. In addition, increased secretion of functional AAT protein protects the lungs from neutrophil elastase and associated proteolytic enzymes. Applicants have developed several rAAV vectors that provide for delivery of microRNAs targeted against mutant AAT, within the same proviral cassette as a gene encoding wild-type AAT. In some embodiments, the microRNAs are delivered using rAAV vectors that have previously been used in clinical trials.

Isolated Nucleic Acids

In general, the invention provides isolated nucleic acids, which may be rAAV vectors, useful for treating genetic disease. The isolated nucleic acids typically comprise one or more regions that encode one or more inhibitory RNAs that target an endogenous mRNA of a subject. The isolated nucleic acids also typically comprise one or more regions that encode one or more exogenous mRNAs. The protein(s) encoded by the one or more exogenous mRNAs may or may not be different in sequence composition than the protein(s) encoded by the one or more endogenous mRNAs. For example, the one or more endogenous mRNAs may encode a wild-type and mutant version of a particular protein, such as may be the case when a subject is heterozygous for a particular mutation, and the exogenous mRNA may encode a wild-type mRNA of the same particular protein. In this case, typically the sequence of the exogenous mRNA and endogenous mRNA encoding the wild-type protein are sufficiently different such that the exogenous mRNA is not targeted by the one or more inhibitory RNAs. This may be accomplished, for example, by introducing one or more silent mutations into the exogenous mRNA such that it encodes the same protein as the endogenous mRNA but has a different nucleic acid sequence. In this case, the exogenous mRNA may be referred to as "hardened." Alternatively, the inhibitory RNA (e.g. miRNA) can target the 5' and/or 3' untranslated regions of the endogenous mRNA. These 5' and/or 3' regions can then be removed or replaced in the exogenous mRNA such that the exogenous mRNA is not targeted by the one or more inhibitory RNAs.

In another example, the one or more endogenous mRNAs may encode only mutant versions of a particular protein, such as may be the case when a subject is homozygous for a particular mutation, and the exogenous mRNA may encode a wild-type mRNA of the same particular protein. In this case, the sequence of the exogenous mRNA may be hardened as described above, or the one or more inhibitory RNAs may be designed to discriminate the mutated endogenous mRNA from the exogenous mRNA.

In some cases, the isolated nucleic acids typically comprise a first region that encodes one or more first inhibitory RNAs (e.g., miRNAs) comprising a nucleic acid having sufficient sequence complementary with an endogenous mRNA of a subject to hybridize with and inhibit expression of the endogenous mRNA, in which the endogenous mRNA encodes a first protein. The isolated nucleic acids also typically include a second region encoding an exogenous mRNA that encodes a second protein, in which the second protein has an amino acid sequence that is at least 85% identical to the first protein, in which the one or more first inhibitory RNAs do not comprise a nucleic acid having sufficient sequence complementary to hybridize with and inhibit expression of the exogenous mRNA. For example, the first region may be positioned at any suitable location. The first region may be positioned within an untranslated portion of the second region. The first region may be positioned in any untranslated portion of the nucleic acid, including, for example, an intron, a 5' or 3' untranslated region, etc.

In some cases, it may be desirable to position the first region upstream of the first codon of the exogenous mRNA. For example, the first region may be positioned between the first codon of the exogenous mRNA and 2000 nucleotides upstream of the first codon. The first region may be positioned between the first codon of the exogenous mRNA and 1000 nucleotides upstream of the first codon. The first region may be positioned between the first codon of the exogenous mRNA and 500 nucleotides upstream of the first codon. The first region may be positioned between the first codon of the exogenous mRNA and 250 nucleotides upstream of the first codon. The first region may be positioned between the first codon of the exogenous mRNA and 150 nucleotides upstream of the first codon.

In some cases, the first region may be positioned downstream of a portion of the second region encoding the poly-A tail of the exogenous mRNA. The first region may be between the last codon of the exogenous mRNA and a position 2000 nucleotides downstream of the last codon. The first region may be between the last codon of the exogenous mRNA and a position 1000 nucleotides downstream of the last codon. The first region may be between the last codon of the exogenous mRNA and a position 500 nucleotides downstream of the last codon. The first region may be between the last codon of the exogenous mRNA and a position 250 nucleotides downstream of the last codon. The first region may be between the last codon of the exogenous mRNA and a position 150 nucleotides downstream of the last codon.

The nucleic acid may also comprise a third region encoding a one or more second inhibitory RNAs (e.g., miRNAs) comprising a nucleic acid having sufficient sequence complementary to hybridize with and inhibit expression of the endogenous mRNA. As with the first region, the third region may be positioned at any suitable location. For example, the third region may be positioned in an untranslated portion of the second region, including, for example, an intron, a 5' or 3' untranslated region, etc. The third region may be positioned upstream of a portion of the second region encoding the first codon of the exogenous mRNA. The third region may be positioned downstream of a portion of the second region encoding the poly-A tail of the exogenous mRNA. In some cases, when the first region is positioned upstream of the first codon, the third region is positioned downstream of the portion of the second region encoding the poly-A tail of the exogenous mRNA, and vice versa.

In some cases, the first region and third regions encode the same set of one or more inhibitory RNAs (e.g., miRNAs). In other cases, the first region and third regions encode a different set of one or more inhibitory RNAs (e.g., miRNAs). In some cases, the one or more inhibitory RNAs (e.g., miRNAs) encoded by the first region target one or more of the same genes as the one or more inhibitory RNAs (e.g., miRNAs) encoded by the third region. In some cases, the one or more inhibitory RNAs (e.g., miRNAs) encoded by the first region do not target any of the same genes as the one or more inhibitory RNAs (e.g., miRNAs) encoded by the third region. It is to be appreciated that inhibitory RNAs (e.g., miRNAs) which target a gene have sufficient complementarity with the gene to bind to and inhibit expression (e.g., by degradation or inhibition of translation) of the corresponding mRNA.

The first and third regions may also encode a different number of inhibitory RNAs (e.g., miRNAs). For example, the first region and third regions may independently encode 1, 2, 3, 4, 5, 6 or more inhibitory RNAs (e.g., miRNAs). The first and third regions are not limited to comprising any one particular inhibitory RNA, and may include, for example, a miRNA, an shRNA, a TuD RNA, a microRNA sponge, an antisense RNA, a ribozyme, an aptamer, or other appropriate inhibitory RNA. In some cases, the first region and/or third region comprises one or more miRNAs. The one or more miRNAs may comprise a nucleic acid sequence encoded by a sequence selected from the group consisting of SEQ ID NOS: 17-19 and 21-23.

As disclosed herein, the second protein may have an amino acid sequence that is at least 85% identical to the first protein. Accordingly, the second protein may have an amino acid sequence that is at least 88%, at least 90%, at least 95%, at least 98%, at least 99% or more identical to the first protein. In some case, the second protein differs from the first protein by 1, 2, 3, 4, 5, 6, 7, 8, 9, 10 or more amino acids. In some cases, one or more of the differences between the first protein and second protein are conservative amino acid substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Accordingly, conservative amino acid substitutions may provide functionally equivalent variants, or homologs of an endogenous protein.

It should be appreciated that in some cases the second protein may be a marker protein (e.g., a fluorescent protein, a fusion protein, a tagged protein, etc.). Such constructs may be useful, for example, for studying the distribution of the encoded proteins within a cell or within a subject and are also useful for evaluating the efficiency of rAAV targeting and distribution in a subject.

In some embodiments of the isolated nucleic acids, the first protein is alpha-1 antitrypsin (AAT) protein. An exemplary sequence of a wild-type AAT is provided at SEQ ID NO: 1 or 2. Accordingly, in some cases, the endogenous mRNA may comprise the RNA sequence specified by the sequence set forth in SEQ ID NO: 5. The endogenous mRNA may comprise the RNA sequence as specified by any one of the sequences set forth in SEQ ID NOS: 6-16. In some cases, the AAT protein is a human AAT protein. The AAT protein may have a sequence as set forth in SEQ ID NO: 1 or 2 or one or more mutations thereof as identified in Table 1, e.g. SEQ ID NO: 3 or 4. The exogenous mRNA may have one or more silent mutations compared with the endogenous mRNA. The exogenous mRNA may comprise the RNA sequence specified by the sequence set forth in SEQ ID NO: 20. The exogenous mRNA sequence may or may not encode a peptide tag (e.g., a myc tag, a his-tag, etc.) linked to the encoded protein. Often, in a construct used for clinical purposes, the exogenous mRNA sequence does not encode a peptide tag linked to the encoded protein.

As described further below, the isolated nucleic acids may comprise inverted terminal repeats (ITR) of an AAV serotypes selected from the group consisting of: AAV1, AAV2, AAV5, AAV6, AAV6.2, AAV7, AAV8, AAV9, AAV10, AAV11 and variants thereof. The isolated nucleic acids may also include a promoter operably linked with the one or more first inhibitory RNAs, the exogenous mRNA, and/or the one or more second inhibitory RNAs. The promoter may be tissue-specific promoter, a constitutive promoter or inducible promoter.

TABLE 1

Mutations in Human AAT - Entrez Gene ID: 5265

| Chr. position | mRNA position | dbSNPrs# cluster id | Function | dbSNP allele | Protein residue | Codon position | Amino acid position |
|---|---|---|---|---|---|---|---|
| 94844794 | 1822 | rs78787657 | missense | A | Lys [K] | 1 | 417 |
| | | | contig reference | C | Gln [Q] | 1 | 417 |
| 94844797 | 1819 | rs3191200 | missense | C | Pro [P] | 1 | 416 |
| | | | contig reference | A | Thr [T] | 1 | 416 |
| 94844842 | 1774 | rs17850837 | missense | A | Lys [K] | 1 | 401 |
| | | | contig reference | C | Gln [Q] | 1 | 401 |
| 94844843 | 1773 | rs1303 | missense | C | Asp [D] | 3 | 400 |
| | | | contig reference | A | Glu [E] | 3 | 400 |
| 94844855 | 1761 | rs13170 | synonymous | T | Phe [F] | 3 | 396 |
| | | | contig reference | C | Phe [F] | 3 | 396 |
| 94844866 | 1750 | rs61761869 | missense | T | Ser [S] | 1 | 393 |
| | | | contig reference | C | Pro [P] | 1 | 393 |
| 94844887 | 1729 | rs12233 | missense | T | Ser [S] | 1 | 386 |
| | | | contig reference | C | Pro [P] | 1 | 386 |
| 94844912 | 1704 | rs28929473 | missense | T | Phe [F] | 3 | 377 |
| | | | contig reference | A | Leu [L] | 3 | 377 |
| 94844926 | 1690 | rs12077 | missense | T | Trp [W] | 1 | 373 |
| | | | contig reference | G | Gly [G] | 1 | 373 |
| 94844942 | 1674 | rs1050520 | synonymous | G | Lys [K] | 3 | 367 |
| | | | contig reference | A | Lys [K] | 3 | 367 |
| 94844947 | 1669 | rs28929474 | missense | A | Lys [K] | 1 | 366 |
| | | | contig reference | G | Glu [E] | 1 | 366 |
| 94844954 | 1662 | rs1050469 | synonymous | G | Thr [T] | 3 | 363 |
| | | | contig reference | C | Thr [T] | 3 | 363 |
| 94844957 | 1659 | rs1802961 | synonymous | T | Leu [L] | 3 | 362 |
| | | | contig reference | G | Leu [L] | 3 | 362 |
| 94844959 | 1657 | rs1131154 | missense | A | Met [M] | 1 | 362 |
| | | | contig reference | C | Leu [L] | 1 | 362 |
| 94844960 | 1656 | rs13868 | synonymous | A | Val [V] | 3 | 361 |
| | | | contig reference | G | Val [V] | 3 | 361 |
| 94844961 | 1655 | rs1131139 | missense | C | Ala [A] | 2 | 361 |
| | | | contig reference | T | Val [V] | 2 | 361 |

TABLE 1-continued

| Chr. position | mRNA position | dbSNPrs# cluster id | Function | dbSNP allele | Protein residue | Codon position | Amino acid position |
|---|---|---|---|---|---|---|---|
| Mutations in Human AAT - Entrez Gene ID: 5265 | | | | | | | |
| 94844962 | 1654 | rs72555357 | frame shift | | | 1 | 361 |
| | | | contig reference | G | Val [V] | 1 | 361 |
| 94844965 | 1651 | rs1802959 | missense | A | Thr [T] | 1 | 360 |
| | | | contig reference | G | Ala [A] | 1 | 360 |
| 94844972 | 1644 | rs10427 | synonymous | C | Val [V] | 3 | 357 |
| | | | contig reference | G | Val [V] | 3 | 357 |
| 94844975 | 1641 | rs9630 | synonymous | T | Ala [A] | 3 | 356 |
| | | | contig reference | C | Ala [A] | 3 | 356 |
| 94844977 | 1639 | rs67216923 | frame shift | | | 1 | 356 |
| | | | frame shift | (15bp) | | 1 | 356 |
| | | | contig reference | G | Ala [A] | 1 | 356 |
| 94845814 | 1625 | rs72555374 | frame shift | | | 2 | 351 |
| | | | contig reference | T | Leu [L] | 2 | 351 |
| 94845845 | 1594 | rs28929471 | missense | A | Asn [N] | 1 | 341 |
| | | | contig reference | G | Asp [D] | 1 | 341 |
| 94845893 | 1546 | rs1802962 | missense | T | Cys [C] | 1 | 325 |
| | | | contig reference | A | Ser [S] | 1 | 325 |
| 94845902 | 1537 | rs55704149 | missense | T | Tyr [Y] | 1 | 322 |
| | | | contig reference | G | Asp [D] | 1 | 322 |
| 94845914 | 1525 | rs117001071 | missense | T | Ser [S] | 1 | 318 |
| | | | contig reference | A | Thr [T] | 1 | 318 |
| 94845917 | 1521 | rs35624994 | frame shift | | Ser [S] | 3 | 316 |
| | | | frame shift | C | Ser [S] | 3 | 316 |
| | | | contig reference | CA | Ser [S] | 3 | 316 |
| 94847218 | 1480 | rs1802963 | nonsense | T | xxx [X] | 1 | 303 |
| | | | contig reference | G | Glu [E] | 1 | 303 |
| 94847262 | 1436 | rs17580 | missense | T | Val [V] | 2 | 288 |
| | | | contig reference | A | Glu [E] | 2 | 288 |
| 94847285 | 1413 | rs1049800 | synonymous | C | Asp [D] | 3 | 280 |
| | | | contig reference | T | Asp [D] | 3 | 280 |
| 94847306 | 1392 | rs2230075 | synonymous | T | Thr [T] | 3 | 273 |
| | | | contig reference | C | Thr [T] | 3 | 273 |
| 94847351 | 1347 | rs34112109 | synonymous | A | Lys [K] | 3 | 258 |
| | | | contig reference | G | Lys [K] | 3 | 258 |
| 94847357 | 1341 | rs8350 | missense | G | Trp [W] | 3 | 256 |
| | | | contig reference | T | Cys [C] | 3 | 256 |
| 94847386 | 1312 | rs28929470 | missense | T | Cys [C] | 1 | 247 |
| | | | contig reference | C | Arg [R] | 1 | 247 |
| 94847407 | 1291 | rs72552401 | missense | A | Met [M] | 1 | 240 |
| | | | contig reference | G | Val [V] | 1 | 240 |
| 94847415 | 1283 | rs6647 | missense | C | Ala [A] | 2 | 237 |
| | | | contig reference | T | Val [V] | 2 | 237 |
| 94847452 | 1246 | rs11558264 | missense | C | Gln [Q] | 1 | 225 |
| | | | contig reference | A | Lys [K] | 1 | 225 |
| 94847466 | 1232 | rs11558257 | missense | T | Ile [I] | 2 | 220 |
| | | | contig reference | G | Arg [R] | 2 | 220 |
| 94847475 | 1223 | rs11558265 | missense | C | Thr [T] | 2 | 217 |
| | | | contig reference | A | Lys [K] | 2 | 217 |
| 94849029 | 1119 | rs113813309 | synonymous | T | Asn [N] | 3 | 182 |
| | | | contig reference | C | Asn [N] | 3 | 182 |
| 94849053 | 1095 | rs72552402 | synonymous | T | Thr [T] | 3 | 174 |
| | | | contig reference | C | Thr [T] | 3 | 174 |
| 94849061 | 1087 | rs112030253 | missense | A | Arg [R] | 1 | 172 |
| | | | contig reference | G | Gly [G] | 1 | 172 |
| 94849109 | 1039 | rs78640395 | nonsense | T | xxx [X] | 1 | 156 |
| | | | contig reference | G | Glu [E] | 1 | 156 |
| 94849140 | 1008 | rs11558263 | missense | A | Arg [R] | 3 | 145 |
| | | | contig reference | C | Ser [S] | 3 | 145 |
| 94849151 | 997 | rs20546 | synonymous | T | Leu [L] | 1 | 142 |
| | | | contig reference | C | Leu [L] | 1 | 142 |
| 94849160 | 988 | rs11558261 | missense | A | Ser [S] | 1 | 139 |
| | | | contig reference | G | Gly [G] | 1 | 139 |
| 94849201 | 947 | rs709932 | missense | A | His [H] | 2 | 125 |
| | | | contig reference | G | Arg [R] | 2 | 125 |
| 94849228 | 920 | rs28931572 | missense | A | Asn [N] | 2 | 116 |
| | | | contig reference | T | Ile [I] | 2 | 116 |
| 94849303 | 845 | rs28931568 | missense | A | Glu [E] | 2 | 91 |
| | | | contig reference | G | Gly [G] | 2 | 91 |
| 94849325 | 823 | rs111850950 | missense | A | Thr [T] | 1 | 84 |
| | | | contig reference | G | Ala [A] | 1 | 84 |
| 94849331 | 817 | rs113817720 | missense | A | Thr [T] | 1 | 82 |
| | | | contig reference | G | Ala [A] | 1 | 82 |
| 94849345 | 803 | rs55819880 | missense | T | Phe [F] | 2 | 77 |
| | | | contig reference | C | Ser [S] | 2 | 77 |

TABLE 1-continued

| Mutations in Human AAT - Entrez Gene ID: 5265 | | | | | | | |
|---|---|---|---|---|---|---|---|
| Chr. position | mRNA position | dbSNPrs# cluster id | Function | dbSNP allele | Protein residue | Codon position | Amino acid position |
| 94849364 | 784 | rs11575873 | missense | C | Arg [R] | 1 | 71 |
| | | | contig reference | A | Ser [S] | 1 | 71 |
| 94849381 | 767 | rs28931569 | missense | C | Pro [P] | 2 | 65 |
| | | | contig reference | T | Leu [L] | 2 | 65 |
| 94849388 | 760 | rs28931570 | missense | T | Cys [C] | 1 | 63 |
| | | | contig reference | C | Arg [R] | 1 | 63 |
| 94849466 | 682 | rs11558262 | missense | G | Ala [A] | 1 | 37 |
| | | | contig reference | A | Thr [T] | 1 | 37 |
| 94849492 | 656 | rs11558259 | missense | G | Arg [R] | 2 | 28 |
| | | | contig reference | A | Gln [Q] | 2 | 28 |
| 94849548 | 600 | rs11558260 | synonymous | T | Ile [I] | 3 | 9 |
| | | | contig reference | C | Ile [I] | 3 | 9 |
| | | | start codon | | | | 1 |

Methods of Use

The invention also provides methods for expressing alpha 1-antitrypsin (AAT) protein in a subject. Typically, the subject has or suspected of having an AAT deficiency. The methods typically involve administering to a subject an effective amount of a recombinant Adeno-Associated Virus (rAAV) harboring any of the isolated nucleic acids disclosed herein. In general, the “effective amount” of a rAAV refers to an amount sufficient to elicit the desired biological response. In some embodiments, the effective amount refers to the amount of rAAV effective for transducing a cell or tissue ex vivo. In other embodiments, the effective amount refers to the amount effective for direct administration of rAAV to a subject. As will be appreciated by those of ordinary skill in this art, the effective amount of the recombinant AAV of the invention varies depending on such factors as the desired biological endpoint, the pharmacokinetics of the expression products, the condition being treated, the mode of administration, and the subject. Typically, the rAAV is administered with a pharmaceutically acceptable carrier.

The subject may have a mutation in an AAT gene. The mutation may result in decreased expression of wild-type (normal) AAT protein. The subject may be homozygous for the mutation. The subject may be heterozygous for the mutation. The mutation may be a missense mutation. The mutation may be a nonsense mutation. The mutation may be a mutation listed in Table 1. The mutation may result in expression of a mutant AAT protein. The mutant protein may be a gain-of-function mutant or a loss-of-function mutant. The mutant AAT protein may be incapable of inhibiting protease activity. The mutant AAT protein may fail to fold properly. The mutant AAT protein may result in the formation of protein aggregates. The mutant AAT protein may result in the formation of intracellular AAT globules. The mutation may result in a glutamate to lysine substitution at amino acid position 366 in the precursor protein according to the amino acid sequence set forth as SEQ ID NO: 3. In the mature protein, this same mutation occurs at amino acid position 342 (SEQ ID NO: 4). The methods may also involve determining whether the subject has a mutation. Accordingly the methods may involve obtaining a genotype of the AAT gene in the subject.

In some cases, after administration of the rAAV the level of expression of the first protein and/or second protein is determined in the subject. The administration may be performed on one or more occasions. When the administration is performed on one or more occasions, the level of the first protein and/or the level of the second protein in the subject are often determined after at least one administration. In some cases, the serum level of the first protein in the subject is reduced by at least 85% following administration of the rAAV. The serum level of the first protein in the subject may be reduced by at least 90% following administration of the rAAV. The serum level of the first protein in the subject may be reduced by at least 95% following administration of the rAAV. However, in some cases, the serum level of the first protein in the subject is reduced by at least 40%, at least 50%, at least 60%, at least 70%, or at least 80% following administration of the rAAV.

The level (e.g., serum level) of the first protein in the subject may be reduced by at least 85% within 2 weeks following administration of the rAAV. The serum level of the first protein in the subject may be reduced by at least 90% within 2 weeks following administration of the rAAV. The serum level of the first protein in the subject may be reduced by at least 85% within 4 weeks of administration of the rAAV. The reduction may be observed within 1 day, within 2 days, within 3 days, within 4 days, within 5 days, within 6 days, within 1 week, within 2 weeks, within 3 weeks, within 4 weeks or more.

The reduction in the level of the first protein may be sustained for at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or more. In some cases, after 7 weeks of administration of the rAAV, the serum level of the first protein is at a level of at least 50% compared with the serum level of the first protein prior to administration of the rAAV. In certain cases, after 7 weeks of administration of the rAAV, the serum level of the first protein is at a level of at least 75% compared with the serum level of the first protein prior to administration of the rAAV.

In some instances, after administration of the rAAV at least one clinical outcome parameter associated with the AAT deficiency is evaluated in the subject. Typically, the clinical outcome parameter evaluated after administration of the rAAV is compared with the clinical outcome parameter determined at a time prior to administration of the rAAV to determine effectiveness of the rAAV. Often an improvement in the clinical outcome parameter after administration of the rAAV indicates effectiveness of the rAAV. Any appropriate clinical outcome parameter may be used. Typically, the clinical outcome parameter is indicative of the one or more symptoms of an AAT deficiency. For example, the clinical outcome parameter may be selected from the group consisting of: serum levels of the first protein, serum levels of the second protein, presence of intracellular AAT globules, presence of inflammatory foci, breathing capacity, cough frequency, phlegm production, frequency of chest colds or pneumonia, and tolerance for exercise. Intracellular AAT globules or inflammatory foci are evaluated in tissues affected by the AAT deficiency, including, for example, lung tissue or liver tissue.

Recombinant AAVs

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected. In some embodiments, the rAAV comprises a capsid protein having an amino acid sequence corresponding to any one of AAV1, AAV2, AAV3, AAV4, AAV5, AAV6, AAV7, AAV8, AAV9, AAV10, AAV11 and variants thereof. The recombinant AAVs typically harbor an isolated nucleic acid of the invention.

Methods for obtaining recombinant AAVs having a desired capsid protein are well known in the art (See, for example, US 2003/0138772, the contents of which are incorporated herein by reference in their entirety). AAV capsid proteins that may be used in the rAAVs of the invention a include, for example, those disclosed in G. Gao, et al., J. Virol, 78(12):6381-6388 (June 2004); G. Gao, et al, Proc Natl Acad Sci USA, 100(10): 6081-6086 (May 13, 2003); US 2003-0138772, US 2007/0036760, US 2009/0197338, and WO 2010/138263, the contents of which relating to AAVs capsid proteins and associated nucleotide and amino acid sequences are incorporated herein by reference. Typically the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein. In still another alternative, a selected stable host cell may contain selected component(s) under the control of a constitutive promoter and other selected component (s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In some aspects, the invention provides isolated cells. As used herein with respect to cell, the term "isolated" refers to a cell that has been isolated from its natural environment (e.g., from a tissue or subject). As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The foregoing methods for packaging recombinant vectors in desired AAV capsids to produce the rAAVs of the invention are not meant to be limiting and other suitable methods will be apparent to the skilled artisan.

Recombinant AAV Vectors

The isolated nucleic acids of the invention may be recombinant AAV vectors. The recombinant AAV vector may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more inhibitory RNAs (e.g., miRNAs) comprising a nucleic acid that targets an endogenous mRNA of a subject. The transgene may also comprise a region encoding an exogenous mRNA that encodes a protein (e.g., a protein that has an amino acid sequence that is at least 85% identical to the protein encoded by the endogenous mRNA), in which the one or more inhibitory RNAs do not target the exogenous mRNA.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 by in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

For nucleic acids encoding proteins, a polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is derived from SV-40, and is referred to as the SV-40 T intron sequence. Any intron may be from the β-Actin gene. Another vector element that may be used is an internal ribosome entry site (IRES).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, and the dihydrofolate reductase promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In another embodiment, the native promoter, or fragment thereof, for the transgene will be used. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the promoter is a chicken β-actin promoter.

In some embodiments, one or more bindings sites for one or more of miRNAs are incorporated in a transgene of a rAAV vector, to inhibit the expression of the transgene in one or more tissues of a subject harboring the transgenes, e.g., non-liver tissues, non-lung tissues. The skilled artisan will appreciate that binding sites may be selected to control the expression of a transgene in a tissue specific manner. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., liver tissue, lung tissue) and administration subcutaneously, intraopancreatically, intranasally, parenterally, intravenously, intramuscularly, intrathecally, intracerebrally, orally, intraperitoneally, by inhalation or by another route. Routes of administration may be combined, if desired. Delivery of certain rAAVs to a subject may be, for example, by administration into the bloodstream of the subject. Administration into the bloodstream may be by injection into a vein, an artery, or any other vascular conduit.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, intracerebrally, orally, intraperitoneally, or by inhalation.

It can be appreciated by one skilled in the art that desirable administration of rAAV-based therapeutic constructs can also include ex vivo administration. In some embodiments, ex vivo administration comprises (1) isolation of cells or tissue(s) of interest from a subject, (2) contacting the cells or tissue(s) with rAAVs in sufficient amounts to transfect the cells or tissue to provide sufficient levels of gene transfer and expression without undue adverse effect, and (3) transferring cells or tissue back into the subject. In some embodiments, cells or tissues may be cultured ex vivo for several days before and/or after transfection.

Cells or tissues can be isolated from a subject by any suitable method. For example, cells or tissues may be isolated by surgery, biopsy (e.g., biopsy of skin tissue, lung tissue, liver tissue, adipose tissue), or collection of biological fluids such as blood. In some embodiments, cells are isolated from bone marrow. In some embodiments, cells are isolated from adipose tissue. In some embodiments, cells are isolated from a lipoaspirate. Appropriate methods for isolating cells from adipose tissue for ex vivo transfection are known in the art. See, e.g., Kuroda, M., et al., (2011), Journal of Diabetes Investigation, 2: 333-340; Kouki Morizono, et al. Human Gene Therapy. January 2003, 14(1): 59-66; and Patricia A. Zuk, Viral Transduction of Adipose-Derived Stem Cells, Methods in Molecular Biology, 1, Volume 702, Adipose-Derived Stem Cells, Part 4, Pages 345-357.

In some embodiments, the isolated cells comprise stem cells, pluripotent stem cells, lipoaspirate derived stem cells, liver cells (e.g., hepatocytes), hematopeotic stem cells, mesenchymal stem cells, stromal cells, hematopeotic cells, blood cells, fibroblasts, endothelial cells, epithelial cells, or other suitable cells. In some embodiments, cells to be transfected are induced pluripotent stem cells prepared from cells isolated from the subject.

In an embodiment, cells or tissue(s) are transduced at a multiplicity of infection (MOI) of at least 10 infectious units (i.u.) of a rAAV per cell (for example, 10, 100, 1,000, 5,000, 10,000, 100,000 or more i.u.) or at a functionally equivalent viral copy number. In one embodiment, cells or tissue(s) are transduced at a MOI of 10 to 10,000 i.u. Routes for transfer of transfected cells or tissue(s) into a subject include, but are not limited to, subcutaneously, intraopancreatically, intranasally, parenterally, intravenously, intravascularly, intramuscularly, intrathecally, intracerebrally, intraperitoneally, or by inhalation. In some embodiments, transfected cells are administered by hepatic portal vein injection. In some embodiments, transfected cells are administered intravascularly. Methods for ex vivo administration of rAAV are well known in the art (see, e.g., Naldini, L. Nature Reviews Genetics (2011) 12, 301-315, Li, H. et al. Molecular Therapy (2010) 18, 1553-1558, and Loiler et al. Gene Therapy (2003) 10, 1551-1558).

Recombinant AAV Compositions

The rAAVs may be delivered to a subject in compositions according to any appropriate methods known in the art. The rAAV, preferably suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Macaque). The compositions of the invention may comprise a rAAV alone, or in combination with one or more other viruses (e.g., a second rAAV encoding having one or more different transgenes).

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. Still others will be apparent to the skilled artisan.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 μl to about 100 ml of solution containing from about $10^9$ to $10^{16}$ genome copies per subject. Other volumes of solution may be used. The volume used will typically depend, among other things, on the size of the subject, the dose of the rAAV, and the route of administration. For example, for intravenous administration a volume in range of 10 μl to 100 μl, 100 μl to 1 ml, 1 ml to 10 ml, or more may be used. In some cases, a dosage between about $10^{10}$ to $10^{12}$ rAAV genome copies per subject is appropriate. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The isolated nucleic acids, compositions, rAAV vectors, rAAVs, etc. described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

Exemplary embodiments of the invention will be described in more detail by the following examples. These embodiments are exemplary of the invention, which one skilled in the art will recognize is not limited to the exemplary embodiments.

EXAMPLES

Introduction to the Examples

Alpha-1 antitrypsin (AAT) deficiency is one of the most commonly inherited diseases in North America, with a carrier frequency of approximately 4% in the US population. The most common mutation arises as a single base pair change (Glu342Lys, PI*Z, SEQ ID 4) and leads to the synthesis of the mutant Z-AAT protein, which polymerizes and accumulates within hepatocytes, precluding its efficient secretion. The subsequent relative deficiency of serum AAT predisposes to chronic lung disease. Twelve to 15% of homozygous PI*ZZ patients develop significant liver disease, ranging from neonatal hepatitis, cholestatic jaundice and cirrhosis to adult-onset cirrhosis and hepatocellular carcinoma. Liver injury is considered to be a consequence of the pathological accumulation of mutant Z-AAT protein polymers within the endoplasmic reticulum of hepatocytes.

Strategies to alleviate the liver disease are focused on decreasing the presence of the mutant Z-AAT protein in the hepatocytes by either reducing expression of the mutant protein, or augmenting its proteolysis or secretion. In vivo studies of an allele-specific small interfering RNA (siRNA) directed against PI*Z AAT in the Pi*Z transgenic mouse model of AAT deficiency have been performed. In vitro studies using U6-driven shRNA clones in recombinant adeno-associated virus (rAAV) backbones have identified an effective allele-specific siRNA sequence (termed p10) that can reduce Pi*Z AAT protein levels while minimizing knockdown of the normal Pi*M AAT. Using the AAV8 capsid, rAAV-U6-p10 was packaged and administered by hepatic portal vein injection into Pi*Z transgenic mice for direct in vivo targeting of the liver. A similarly delivered AAV8-packaged non-specific siRNA, rAAV-U6-NC, served as a control (NC). Histological data from these studies revealed areas of complete or partial elimination of Z-AAT protein in the liver at 10 days post-injection in the p10 cohort. Analysis of the serum Z-AAT levels shows a kinetically significant reduction for 4 weeks post-injection in the p10 cohort when compared to NC control cohort. To examine the allele-specificity, AAV8-packaged Pi*M-AAT was co-administered with each shRNA construct. For both the p10+Pi*M and NC+Pi*M groups, there was considerable expression of AAT in the liver by histological staining and there was no significant difference in serum AAT levels.

The Pi*Z mutation (Glu342Lys) within exon 5 of alpha-1 antitrypsin (AAT) causes a plasma AAT deficiency (A1AD) which exposes lung tissue to uncontrolled proteolytic attack and can result in emphysema. Pi*Z mutant AAT is retained within the hepatocytes and causes a liver disease in ~12% of patients with the deficiency. Delivering wild-type copies of AAT does not address the liver pathology so down-regulation strategies including siRNA have been targeted to AAT message within hepatocytes. Since mutant AAT-PiZ exhibits a gain-of-function hepatocellular toxicity accumulating in the endoplasmic reticulum, decreasing AAT-Pi*Z mRNA levels (and therefore the protein) may ameliorate or even reverse the liver pathology. In addition, increased secretion of functional AAT protein will theoretically protect the lungs from neutrophil elastase and associated proteolytic enzymes.

The strategies described herein include the development of rAAV mediated therapies to both augment serum levels of normal AAT and down-regulate mutant AAT using miRNA. To achieve expression and secretion of wild-type AAT while simultaneously reducing AAT-PiZ levels. Three miRNA sequences targeting the AAT gene were selected in some embodiments and cloned into two different locations of the expression cassette. The first location is within the intron of the CB promoter driving expression of GFP, and the second location was between the polyA sequence and the 3' end of the gene, an additional construct with miRNAs at both locations was also created. These three constructs were packaged into rAAV8 and delivered to transgenic mice expressing the mutant form of human AAT (hAAT Pi*Z) at $6\times10^{11}$ vector particles per mouse via the tail vein. These experiments showed about a 60% to 80% reduction in secreted AAT protein in mice serum when compared with CB-GFP control vector injected group. It was determined that the 3XD construct was the most efficient for knocking down hAAT, in some embodiments. Liver immuno-histology also showed hAAT Pi*Z protein clearance at 4 weeks after vector delivery. Using an AAT sequence with silent base pair changes to prevent the miRNA silencing allows both up regulation of wildtype AAT gene expression while simultaneously knocking down levels of mutant protein with a single rAAV vector construct.

Materials and Methods rAAV9 Packaging and Purification: Recombinant AAV9 vectors used in this study were generated, purified, and titered by the UMass Gene Therapy Vector Core as previously described.

Cell Culture and Transfection: HEK-293 cells were cultured in Dulbecco's modified Eagle's medium supplemented with 10% fetal bovine serum and 100 mg/1 of penicillin-streptomycin (Gemini Bio-products Cat#400-109, Woodland, Calif.). Cells were maintained in a humidified incubator at 37° C. and 5% CO2. Plasmids were transiently transfected using Lipofectamine 2000 (Cat#11668-027 Invitrogen, Carlsbad, Calif.) according to the manufacturer's instructions. Cell culture supernatants or cell lyses were collected accordingly.

Serum AAT ELISAs

Human AAT ELISA: Total AAT protein levels were detected by ELISA. High binding extra, 96-well plate (Immulon 4, cat#3855 Dynatech Laboratories, Inc., Chantilly, Va.) were coated with 100 μl of goat anti-hAAT (1:500 diluted; cat#55111MP Biomedicals, Irvine Calif.) in Voller's buffer overnight at 4° C. After blocking with 1% non-fat dry milk in PBS-T, duplicate standard curves (hAAT; cat#16-16-011609, Athens Research and Technology, Athens, Ga.,) and serially diluted unknown samples were incubated in the plate at room temperature for 1 hr, a second antibody, Goat anti-hAAT (HRP) (1:5000 diluted, cat #ab7635-5, Abcam Inc, Cambridge, Mass.) was incubated at room temperature for 1 h. The plate was washed with phosphate-buffered saline (PBS)-Tween 20 between reactions. After reaction with TMB peroxidase substrate (KPL, Inc, Gaithersburg, Md.) reactions were stopped by adding 2 N $H_2SO_4$ (cat#A300-500 Fisher, Pittsburgh, Pa.). Plates were read at 450 nm on a VersaMax microplate reader (Molecular Devices).

Z-AAT ELISA: Human Z-AAT protein levels were detected by ELISA using coating antibody (1:100 diluted mouse-anti-human Alpha-1-Antitrypsin-Z, clone F50.4.1 Monoclonal Antibody cat#MON5038, Cell Sciences, Inc., Canton, Mass.). Standard curves were created using PIZ mouse serum with 5% BSA (cat#B4287 Sigma, St. Louis, Mo.). Serially diluted unknown samples were incubated in the plate at 37° C. for 1 hr, secondary antibody and following the step were same as the standard human-AAT ELISA described above, except secondary antibody was diluted in 5% BSA and incubated in the plate at 37° C. for 1 hr.

c-Myc ELISA: c-Myc tag levels were quantified by a similar method as described above. Plates were coated with a c-Myc antibody (1:1000 diluted Goat anti-c-Myc, MA cat#AB19234 Abcam, Cambridge Mass.), plates were then blocked with 5% BSA at 37° C. for 1 hr. Standard curves were generated from supernatants collected from c-Myc-AAT transfected cells.

Real-time RT-PCR

RNA Extraction: Flash frozen mouse liver tissue was ground up in a pestle and mortar and used to extract either small or total RNA using the mirVana miRNA RNA Isolation Kit (cat#AM1560 Ambion, Austin, Tex.) according to the manufacturer's instructions.

microRNA qRT-PCR: microRNA was primed and reverse-transcribed with TaqMan MicroRNA reverse transcription Kit (cat#4366596, Applied Biosystems Foster City, Calif.). Quantitative PCR were performed in duplicate with gene specific RT-miRNA primers and PCR Assays were designed by Applied Biosystems, using TaqMan Gene Expression Master mix (cat#436916, Applied Biosystems, Foster City, Calif.) in a StepOne Plus real-time PCR instrument (Applied Biosystems, Foster City, Calif.).

PIM and PIZ qRT-PCR: Total RNA was primed with oligo (dT) and reverse-transcribed with SuperScript III First-Strand Synthesis kit for RT-PCR (Cat#18989-51, Invitrogen, Carlsbad, Calif.). Quantitative PCR were performed by gene-specific primer pairs. PIM and PIZ share the primers but differ in the probes. Forward primer CCAAGGCCGTGCATAAGG (SEQ ID NO: 29), Reverse primer: GGCCCCAGCAGCTTCAGT (SEQ ID NO: 30), PIZ probe: 6FAM-CTGACCATCGACAAGA-MGBNFQ (SEQ ID NO: 31) and PIM probe: 6FAM-CTGACCATCGACGAGA-MGBNFQ (SEQ ID NO: 32), Reactions were performed using TaqMan Gene Expression Master mix (cat#436916, Applied Biosystems, Foster City, Calif.) in a StepOne Plus real-time PCR instrument (Applied Biosystems, Foster City, Calif.).

Z-AAT Transgenic Mice and rAAV9 Delivery: The PiZ-transgenic mice used in this study have been described previously[8]. All animal procedures were performed according to the guidelines of the Institutional Animal Care and Use Committee of the University of Massachusetts Medical School. Recombinant AAV9 vector was administered by mouse tail veil injection. The injections were performed in the most accessible vessels veins that run the length of both lateral aspects of the tail by grasping the tail at the distal end. Bleeds were performed through the facial vein pre-injection and every week after tail vein rAAV9 delivery until termination of the studies.

Liver Histology: For determination of histological changes, liver samples were fixed in 10% neutral-buffered formalin (Fisher Scientific), and embedded in paraffin. Sections (5 μm) were stained with hematoxylin and eosin and periodic acid-Schiff (PAS) with or without diastase digestion.

Immuno-histochemistry for hAAT was performed as previously described[14], briefly tissue sections (5 μm) were deparaffinized, rehydrated, and blocked for endogenous peroxidase with 3% hydrogen peroxide in methanol for 10 minutes. To detect hAAT expression, tissue sections were incubated with primary antibody, rabbit antihuman AAT (1:800; RDI/Fitzgerald Industries, Concord, Mass.), for overnight at 4° C. Staining was detected using ABC-Rb-HRP and DAB kits (Vector Laboratories, Burlingame, Calif.).

Histology Image Analysis. Slides were stained for PASD to remove glycogen. Whole digital slide images were created using an Aperio CS ScanScope (V, CA) and analyzed using the positive pixel count algorithm (version 9). PASD-positive globules were expressed as the proportion of strong positive pixels to total pixels using a hue value of 0.9, hue width of 0.15, and color saturation threshold of 0.25. The intensity threshold for strong positivity was set to an upper limit of 100.

Analysis of Z-AAT Protein Monomer and Polymer. For soluble/insoluble protein separation, 10 mg of whole liver was added to 2 ml buffer at 4° C. (50 mmol/1 Tris-HCl (pH 8.0), 150 mmol/1 NaCl, 5 mmol/1 KCl, 5 mmol/1 MgCl2, 0.5% Triton X-100, and 80 μl of complete protease inhibitor stock). The tissue was homogenized in a prechilled Dounce homogenizer for 30 repetitions, then vortexed vigorously. A 1-ml aliquot was passed through a 28-gauge needle 10 times. The total protein concentration of the sample was determined, and a 5-μg total liver protein sample was aliquoted and centrifuged at 10,000 g for 30 minutes at 4° C. Supernatant (soluble (S) fraction) was immediately removed into fresh tubes; extreme care was taken to avoid disturbing the pellet (insoluble (I) fraction). The insoluble polymers pellet (I fraction) was denatured and solubilized via addition of 10 1 chilled cell lysis buffer (1% Triton X-100, 0.05% deoxycholate, 10 mmol/1 EDTA in phosphate-buffered saline), vortexed for 30 seconds, sonicated on ice for 10 minutes and vortexed. To each soluble and insoluble sample, 2.5 sample buffer (50% 5 sample buffer (5% sodium dodecyl sulfate, 50% glycerol, 0.5 mol/l Tris (pH 6.8)), 10% mercaptoethanol, 40% ddH2O) was added at a volume of 50% of the sample volume. Samples were boiled and loaded for sodium dodecyl sulfate-polyacrylamide gel electrophoresis (SDS-PAGE); equal amounts of total liver protein were loaded per soluble-insoluble pair in quantitative experiments. Densitometry was performed using Image J Software (NIH, Bethesda, Md.).

Serum Chemistries: Serum samples were analyzed by UMass Mouse Phenotyping Center Analytical Core, using the NExCT Clinical Chemistry Analyzer (Alfa Wassermann Diagnostic Technologies, West Caldwell, N.J.). Serum was analyzed for alanine aminotransferase (ALT) and aspartate aminotransferase (AST) according the manufacturers specifications.

miRNA Microarray Expression Analysis: 8 μg of total RNA were isolated from flash frozen mouse livers using the mirVana miRNA isolation kit (Ambion). The experimental design included six groups with RNA samples from 5 mice each which were assayed on single color arrays for a total of 30 independent microarrays. In brief, the RNA was labeled with Cy5 and hybridized to dual-channel microarray μParaFlo microfluidics chips (LC Sciences) containing miRNA probes to mouse mature miRNAs available in the Sanger miRBase database (Release 16.0) as previously described[15]. Each of the spotted detection probes consisted of a nucleotide sequence complementary to a specific miRNA sequence and a long non-nucleotide spacer that extended the specific sequence away from the chip surface. Fluorescence images were collected using a laser scanner (GenePix 4000B, Molecular Device) and digitized using Array-Pro image analysis software (Media Cybernetics). The data was analyzed including background subtraction, using a LOWESS (locally weighted regression) method on the background-subtracted data as previously described[16]. The normalization is to remove system related variations, such as sample amount variations, and signal gain differences of scanners. Detection was determined to be positive only if transcripts had a signal intensity higher than 3× (background SD) and spot CV<0.5. CV as calculated by (SD)/(signal intensity), and in which repeating probes on the array produced signals from at least 50% of the repeating probes above detection level. Data is represented as a Log 2 transformation. The data was further filtered to remove miRNAs with (normalized) intensity values below a threshold value of 32 across all samples. t-Test were performed between "control" and "test" sample groups where T-values are calculated for each miRNA, and p-values are computed from the theoretical t-distribution. If $p<0.05$, it is plotted as red spot in a log scatter plot.

Figure 1B:
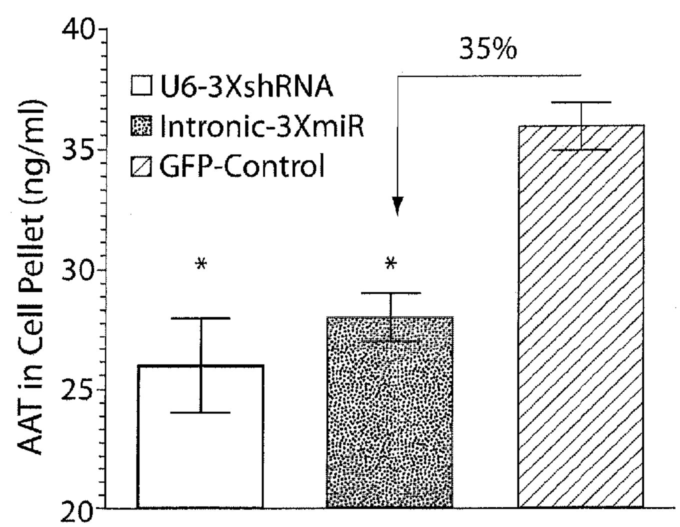

Artificial miRNAs are as Efficient as shRNAs at Downregulating Alpha-1 Antitrypsin In Vitro Efficient Z-AAT knockdown has been demonstrated in vivo and in vitro using shRNAs expressed from a pol III U6 promoter using rAAV8. In order to determine if an alternative and potentially safer approach could be employed using polymerase II driven miRNA expression, three distinct miRNAs targeting the human AAT gene were cloned into the intron of a hybrid chicken beta-actin (CB) promoter driving GFP expression (Table 2 and FIG. 1). An in vitro comparison of the previously used U6 driven shRNAs against the pol II driven miRNAs was carried out on cell lines expressing the human Pi*Z AAT gene. Initially a delay in Z-AAT knockdown with the miRNAs at 24 hrs was observed, but an eventual comparable ~35% reduction in secreted AAT protein by 48 and 72 hrs was observed for both constructs as compared to GFP controls (FIG. 1*a*). A similar reduction was observed in intracellular AAT protein levels assayed from the cell pellets at 72 hrs (FIG. 1*b*).

rAAV9 Expressed miRNAs Mediate Efficient AAT Knockdown In vivo

Figure 2:
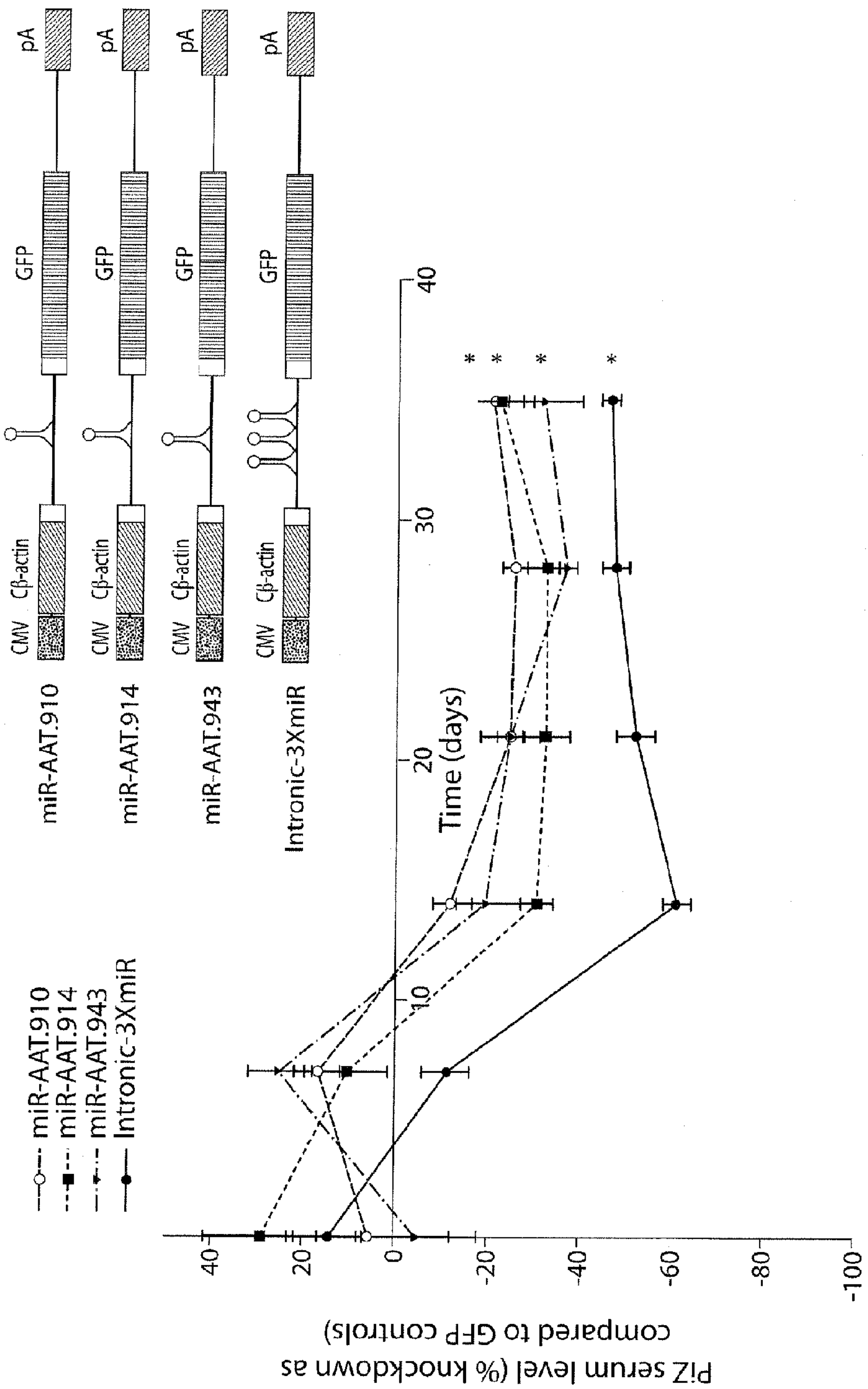
FIG. 2 In vivo silencing of human AAT by rAAV9 expressed miRNAs. Transgenic mice expressing the human PiZ allele were injected with $5\times10^{11}$ vector particles or rAAV9 expressing miRNAs against AAT under the control of the hybrid chicken beta-actin promoter via the tail vein. Serums from each cohort were collected on a weekly basis and were used to assess Z-AAT concentration by ELISA. Data is expressed as group means+SEM (n=6).
Figure 3A:
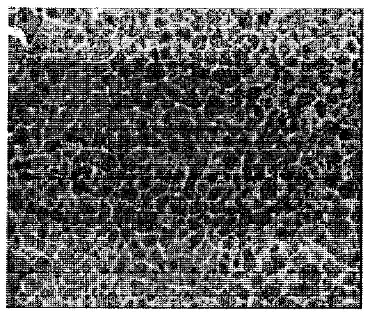
FIG. 3 Liver histology for PiZ transgenic mice 5 weeks post-rAAV9 delivery. Livers from mice receiving rAAV9 vectors with miRNAs and GFP controls were formalin-fixed and stained for AAT, or with a PAS-D assay. Mouse liver sections stained using an anti-human AAT antibody from a mouse treated with (a) intronic-3XmiR or (b) GFP controls. Mouse Liver sections stained with diastase-resistant Periodic Acid Schiff assay from (e&f) intronic-3XmiR or (c&d) GFP controls. (g) Quantitative pixel image analysis of whole liver sections was performed by comparing pixel counts of PASD-positive globules in GFP controls (N=7) to pixel counts of PASD-positive globules in intronic-3XmiR (N=7).
Figure 3B:
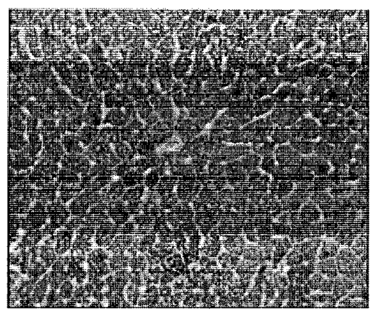
Figure 3C:
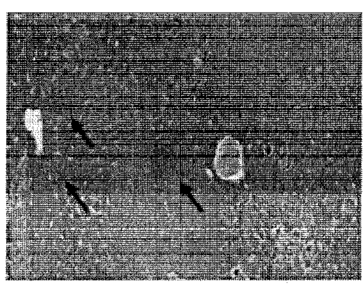
Figure 3D:
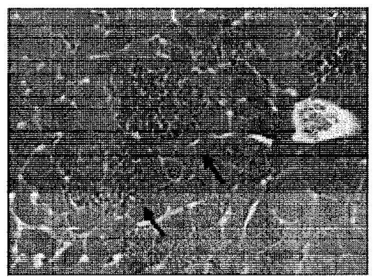
Figure 3E:
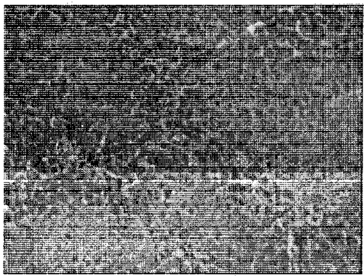
Figure 3F:
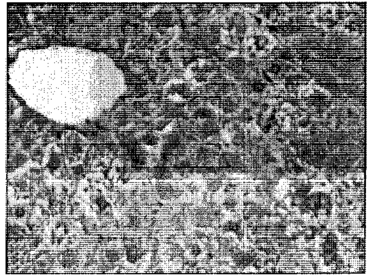
Figure 3G:
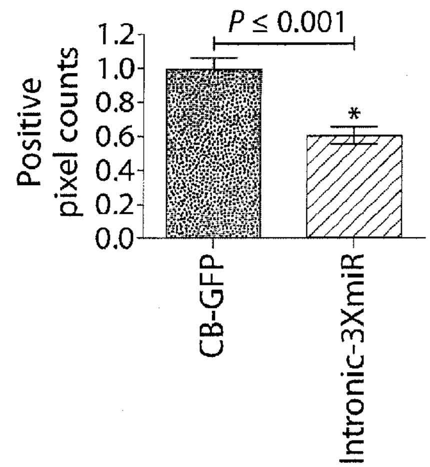

Based on the in vitro findings, the construct with the three intronic miRNA sequences (intronic 3XmiR) along with three other constructs containing the individual miRNAs directed against the Z-AAT were packaged in rAAV and tested in vivo in the PiZ transgenic mice. Five groups of 5 week old mice received: rAAV9-CB-GFP, rAAV9-CBintronic3xmiR-GFP or vector with either one of the individual miRNA via a tail vein injection with 5.0×1011 vector particles (vps) of rAAV9. Mice were bled weekly for a total of 5 weeks to check for circulating Z-AAT levels and were sacrificed on day 35 post rAAV delivery. As shown in FIG. 2, mice receiving 3X intronic miRNAs (intronic 3Xmir) had on average a sustained 50-60% decrease in serum AAT levels when compared to baseline values while mice receiving the single intronic miRNAs had on average a knockdown of 30% as compared to mice receiving the GFP control vector.

To evaluate the effect that miRNA mediated knockdown was having at the organ level, the livers of these mice were evaluated 5 weeks post rAAV delivery for abundance of intracellular Z-AAT. As can be appreciated from liver immunostains for human AAT in FIG. 3, there was a marked decrease in AAT positive staining in the livers belonging to mice in the rAAV9-intronic3XmiR-GFP treated group. In addition to the drastic reduction in AAT positive staining, likewise there was a dramatic decrease in intracellular AAT globules as determined by diastase resistant PAS (PASD) positive staining. Importantly the reduction in both PASD and hAAT staining was accompanied by a reduction in inflammatory foci in the GFP group (FIG. 3). This suggests that the reduction in hAAT accumulation in the PiZ mice livers may be alleviating inflammation as evidenced by the reduction in inflammatory infiltrates.

Figure 4:
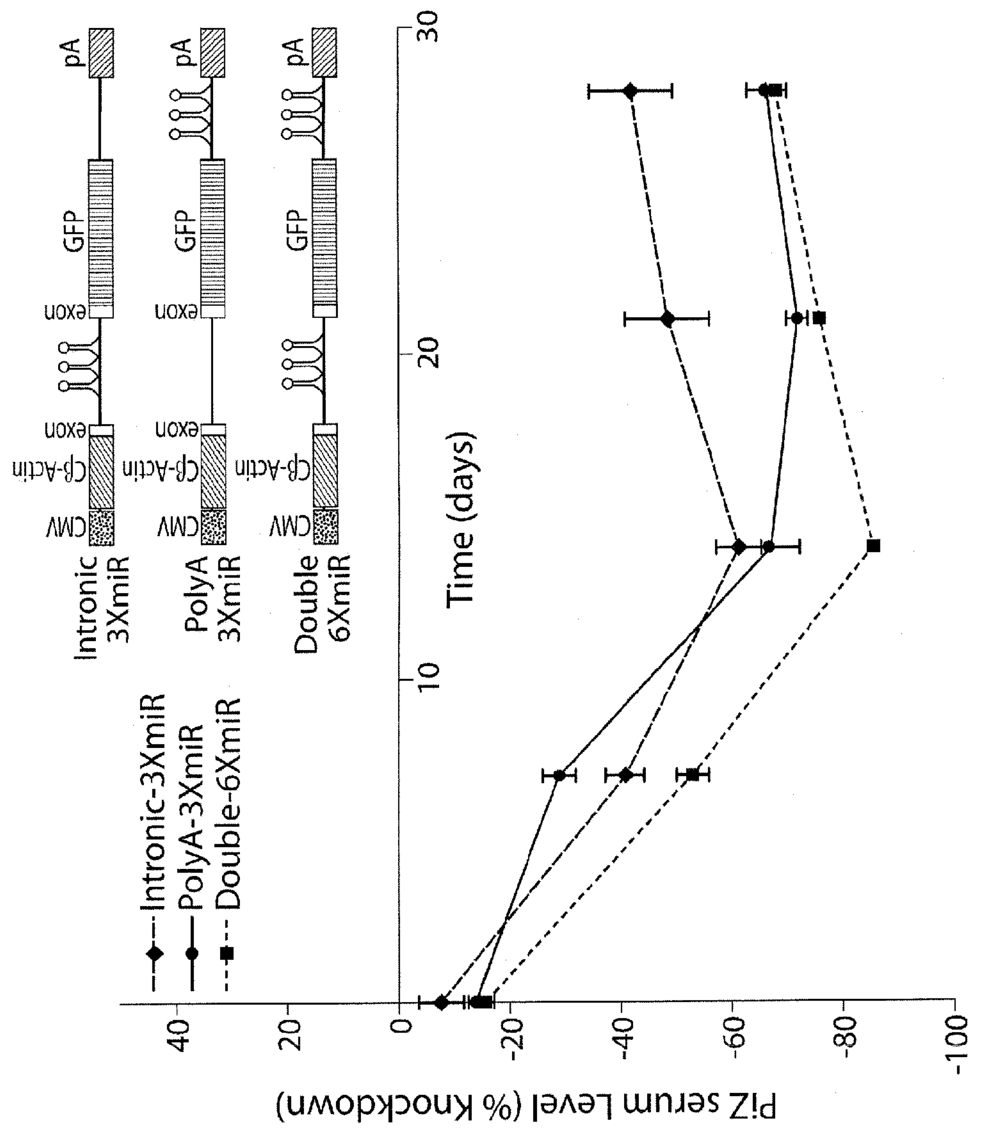
FIG. 4 In vivo optimization of anti-AAT miRNA delivery within rAAV9 vectors. Transgenic mice expressing the human PiZ allele were injected with $5\times10^{11}$ vector particles or rAAV9 expressing miRNAs against AAT under the control of the hybrid chicken beta-actin promoter via the tail vein. Serums from each cohort were collected on a weekly basis and were used to assess Z-AAT concentration by ELISA.
Figure 5:
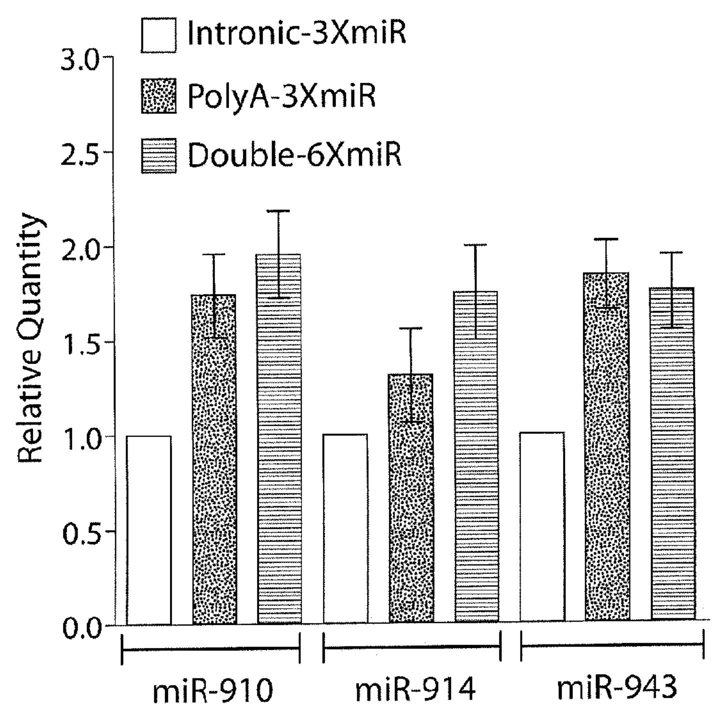
FIG. 5 Quantitative RT-PCR for artificial miRNA in vivo. Total RNA from mouse livers was used to assay for the presence of the 3 artificial anti-AAT miRNAs from mice receiving rAAV9-miRNA vectors. *<0.05 as determined by a two-way unpaired student t-test.

Onset and Degree of Knockdown are Dependent on miRNA Location within the Expression Cassette While delivering 3 miRNAs within the intron of the CB promoter was successful at lowering Z-AAT expression, it was unclear whether the location of the miRNAs within the expression cassette had any effect on their efficiency. It was investigated whether cloning the 3 miRNAs between the 3' end of the GFP gene and the polyA tail would have an effect on the kinetics of AAT knockdown Likewise it was evaluated whether cloning the 3 miRNAs at both locations would increase (e.g., double) the amount of miRNAs being produced and lead to a further enhancement of AAT knockdown. As in the previous experiments, Z-AAT transgenic mice received $5\times10^{11}$ vector particles of rAAV9 vectors expressing the miRNAs either from the intron (intronic-3XmiR), polyA region (PolyA-3XmiR) or at both locations at once (Double-6XmiR) (see diagram in FIG. 4). Analysis of serum Z-AAT levels revealed that by four weeks the PolyA-3XmiR and Double-6XmiR were more effective than the intronic-3XmiR vector at clearing serum Z-AAT levels by 85-70% and in some cases by up to 95% with the Double-6XmiR vector (FIG. 4). Real-time quantitative RT-PCR analysis of liver tissue from these mice was performed to assay for the abundance of each of the three artificial vector derived miRs (910, 914, 943). As indicated in FIG. 5, both the PolyA-3XmiR and Double-6XmiR vectors produced about two-fold more copies of each of the miRs (FIG. 5).

Figure 6A:
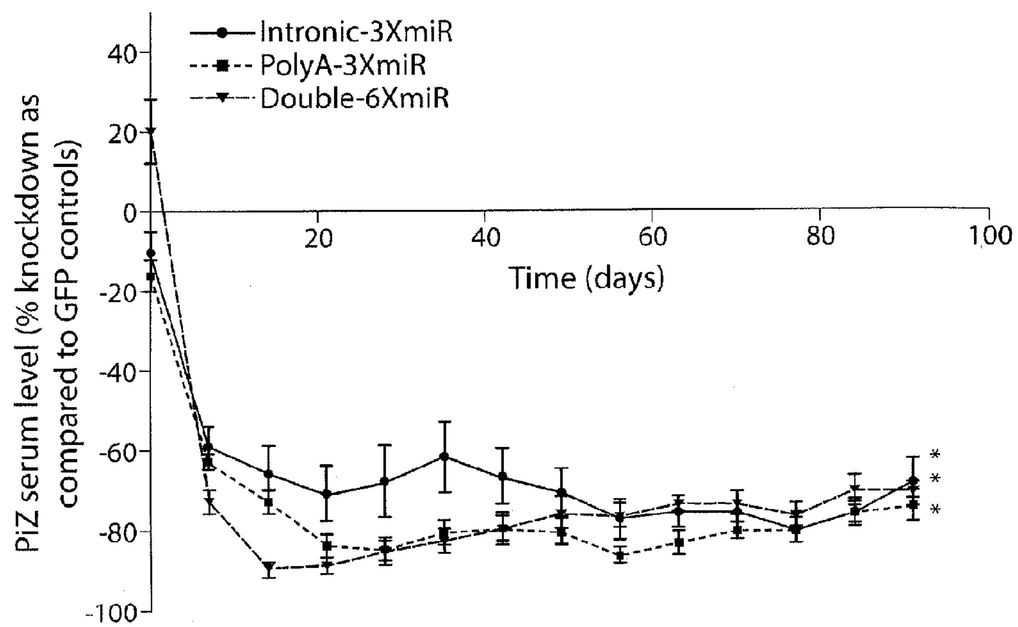
FIG. 6 Long-term In vivo silencing of human AAT by rAAV9 expressed miRNAs. Transgenic mice expressing the human PiZ allele were injected with 1×1012 vector particles or rAAV9 expressing miRNAs against AAT under the control of the hybrid chicken beta-actin promoter via the tail vein. (a) Serums from each cohort were collected on a weekly basis and were used to assess Z-AAT concentration by ELISA. (b) ATT from liver lysates of mice was analyzed by immunoblot after monomer and polymer separation. The 52 kDa Z-AAT was from livers processed and separated into a monomer and polymer pool. Densitometric analysis was performed for the (c) monomer and (d) polymer pools using Image J software. Baseline serums and those collected two weeks-post rAAV9 delivery were used to analyze liver function as determined by (e) ALT and (f) AST concentration. Data is expressed as group means+SEM. *<0.05 as determined by a two-way unpaired student ¬t-test comparing rAAV9 cohorts vs. baseline.
Figure 6B:
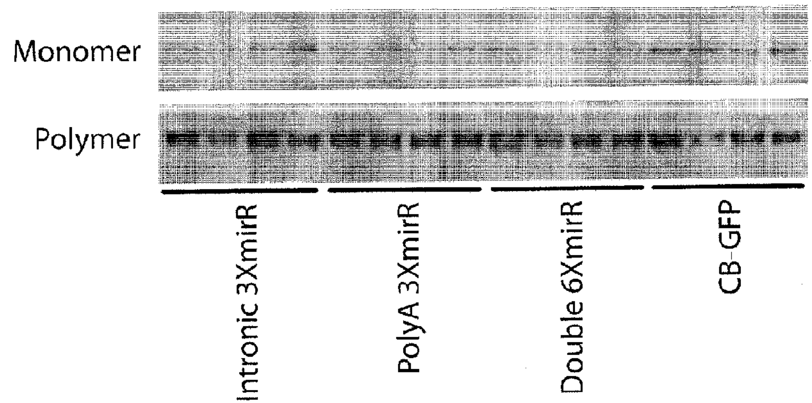
Figure 6C:
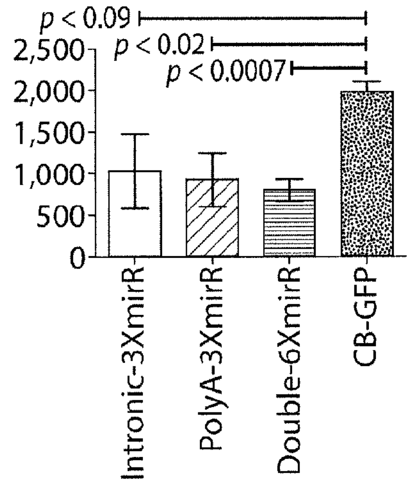
Figure 6D:
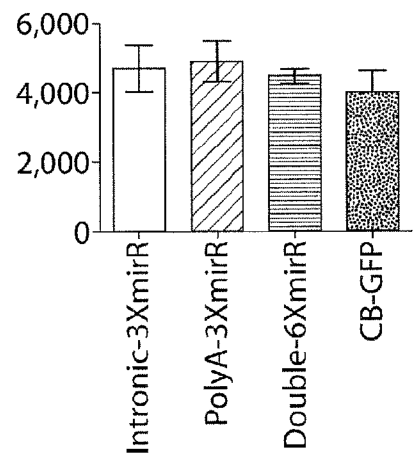
Figure 6E:
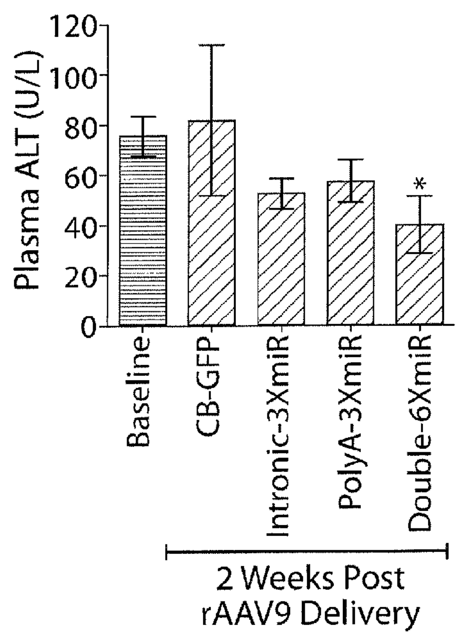
Figure 6F:
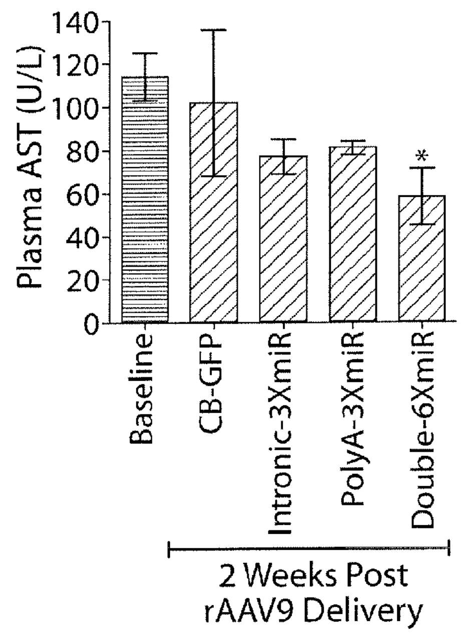

Having achieved a short-term clinically significant knockdown of more than 50% of Z-AAT protein levels it was necessary to determine if this knockdown could be sustained for longer periods of time. Once again the three vector constructs were delivered via the tail vein at a slightly higher titer of $1.0\times10^{12}$ vector particles per mouse and serum Z-AAT levels were monitored weekly for 3 months. The knockdown onset of the three vector varied within 7 weeks, the Double-6XmiR vector achieved 90% knockdown 2 weeks after delivery, the PolyA-3XmiR reached this mark by the third week while the intronic-3XmiR vector remained in the range of 50-65% knockdown for the first 7 weeks (FIG. 6*a*). Further analysis of liver homogenates to determine whether this reduction was in the monomer or polymer pools of Z-AAT was performed on all groups. Monomer and polymer Z-AAT fractions were separated under nondenaturing conditions after which, the fractions were denatured and quantitatively assessed by immunoblotting. A reduction was observed in all groups in the monomer pool 3 months after miRNA treatment. Densitometric analysis of the bands showed significant differences in the PolyA-3XmiR and Double-6XmiR as compared to mice treated with a control vector (FIG. 6 *b-d*). This knockdown observed at two weeks in FIG. 6*a* was accompanied by significant reduction in serum ALT and AST in the Double-6XmiR group with clear decreasing trends in the two other groups expressing anti-AAT miRs (FIGS. 6*e* and 6*f*). Although Z-AAT levels rose slightly for animals in the Double-6XmiR and PolyA-3XmiR groups between week 7 and 13, all three vectors stabilized at a sustained level of about 75% knockdown of Z-AAT for the remainder of the study (FIG. 6).

Figure 7A:
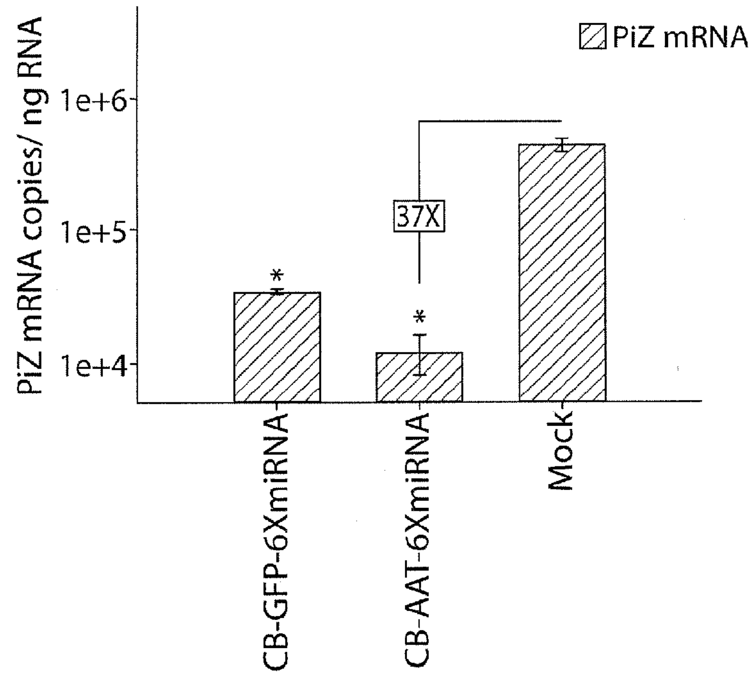
FIG. 7 In vitro assessment of dual-function pro-viral plasmid. HEK-293 cells were contrasfected with human Z-AAT plasmid and either the Double-6XmiR-CB-AAT plasmid, a GFP or PBS control. Cells were processed for RNA at 72 hours and were analyzed for (a) PiZ-mRNA or (b) PiM mRNA with qRT-PCR. Data is expressed as group means+SEM (n=6). *<0.05 as determined by a two-way unpaired student t-test.
Figure 7B:
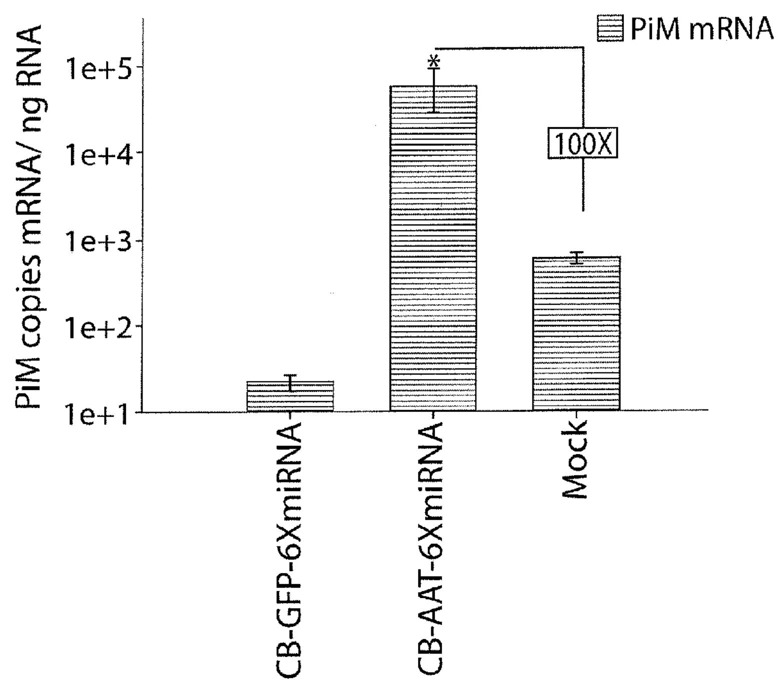

In vitro Delivery of miRNAs Against Z-AAT and Gene Correction with M-AAT Using a Single Vector A dual-function vector that would simultaneously augment protein levels of the wild-type M-AAT protein, thereby addressing both liver disease caused by the toxic gain-of-function of Z-AAT polymers and the loss-of-function caused by the absence of circulating M-AAT, was evaluated. To achieve this, the GFP gene was replaced with a wild-type AAT gene that had silent base pair changes at the miRNAs' target sites, thus making it impervious to the miRNA mediated knockdown. HEK-293 cells were co-transfected with two plasmids, one of the plasmid expressed Z-AAT and the other one was either the Double-6XmiR-GFP, Double-6XmiR-AAT (containing the hardened, knockdown-impervious AAT gene) or a control. The transfected cells were incubated for 72 hrs and RNA was harvested from cell pellets for a quantitative RT-PCR analysis of Z-AAT and M-AAT transcripts. Analysis of Z-AAT mRNA levels revealed the both Double-6XmiR-GFP and Double-6XmiR-AAT produced a significant knockdown of up to 37-fold in Z-AAT mRNA copies as compared to the mock transfected cells (FIG. 7*a*). Furthermore, quantitative RT-PCR for wild-type M-AAT transcripts from the same RNA pool, revealed that the Double-6XmiR-AAT construct upregulated M-AAT expression by more than 100-fold over the endogenous levels observed in control transfected cells (FIG. 7*b*).

In Vivo Delivery of Dual-function Vectors

Figure 8A:
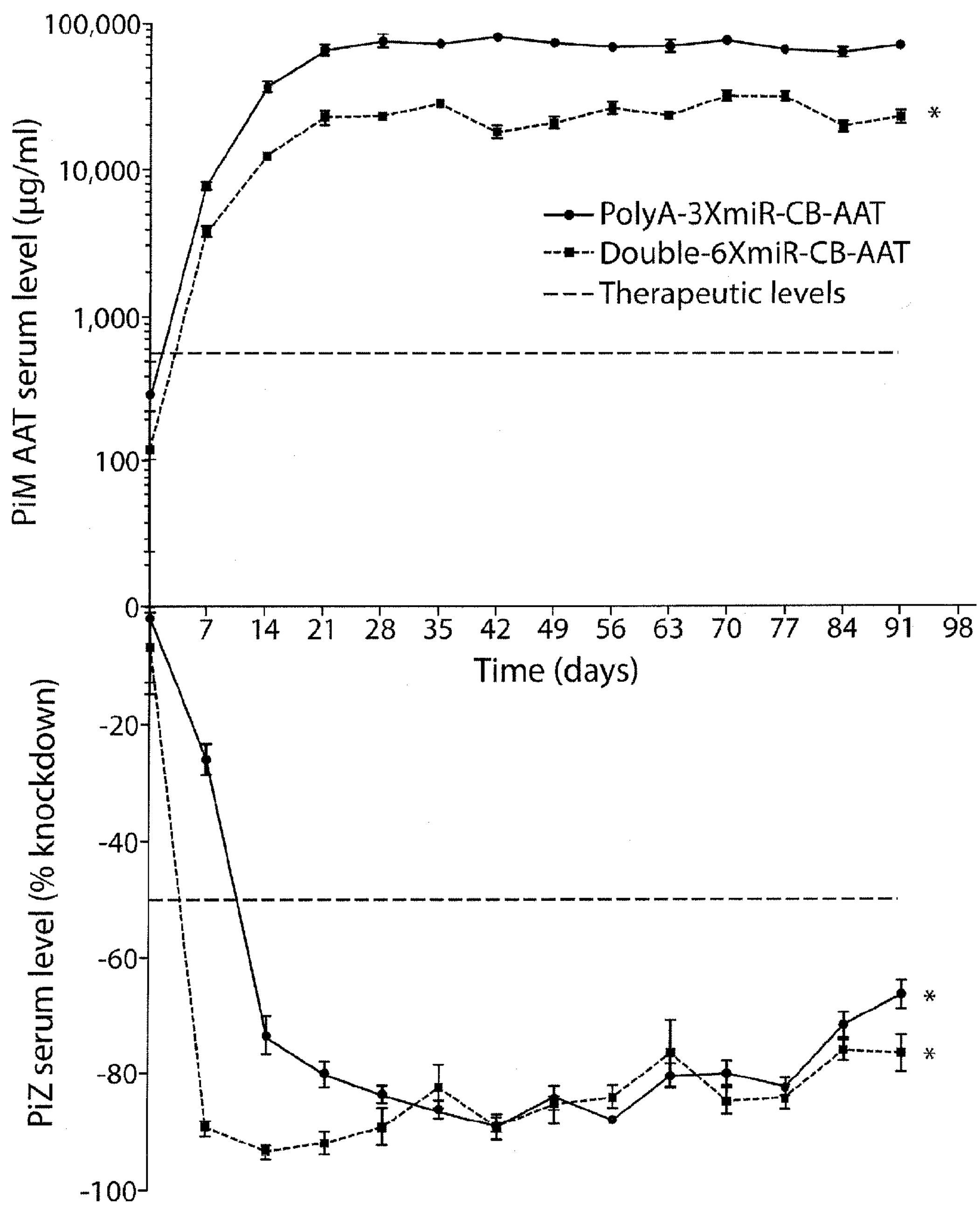
FIG. 8 In vivo knockdown of Z-AAT with simultaneous augmentation of M-AAT after rAAV9 dual function vector delivery. Transgenic mice expressing the human PiZ allele were injected with $1\times10^{12}$ vector particles or rAAV9 expressing miRNAs against AAT and a de-targeted cMyc tagged wildtype M-AAT cDNA under the control of the hybrid chicken beta-actin promoter via the tail vein. (a) Serum from each cohort was collected on a weekly basis and was used to assess Z-AAT concentration by Z-AAT specific ELISA and M-AAT levels by cMyc ELISA. Total RNA from mouse livers was used to assay for the presence of the either (b) Z-AAT mRNA or (c) M-AAT mRNA by qRT-PCR. Data is expressed as group means+SEM (n=6). *<0.05 as determined by a two-way unpaired student t-test.

Taking the in vitro findings into consideration as well as the more rapid onset and the decreased variability in knockdown observed with the Double-6XmiR and PolyA-3XmiR vectors (FIG. 6), both of these miRNA configurations were tested as dual function vectors in vivo. Three cohorts of seven mice each were dosed with $1.0\times10^{12}$ vector particles with either a GFP control, Double-6XmiR-CB-AAT or a PolyA-3XmiR-CB-AAT rAAV9 vectors. Serum was harvested weekly from the mice for 13 weeks and was analyzed for Z-AAT serum levels with a PiZ specific ELISA and for M-AAT levels with an ELISA detecting the cMYC tag on the M-AAT cDNA. Changes in Z-AAT serum levels were comparable to previous experiments, with a sustained knockdown around 75-85% for both vectors (FIG. 8*a* bottom panel). A more rapid onset of knockdown was seen with the Double-6XmiR vector but the PolyA-3XmiR vector achieved similar knockdown by the fourth week. As the Z-AAT knockdown progressed, a concomitant rise in circulating M-AAT was observed from mice receiving the dual function vectors (FIG. 8*a* upper panel).

Figure 8B:
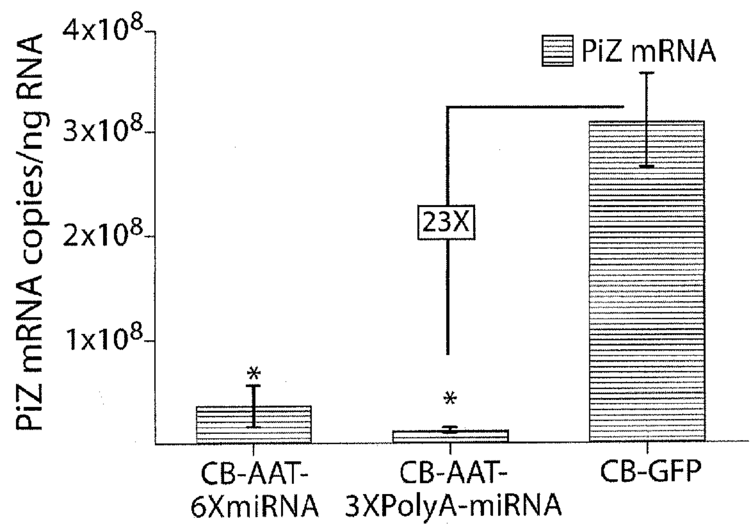
Figure 8C:
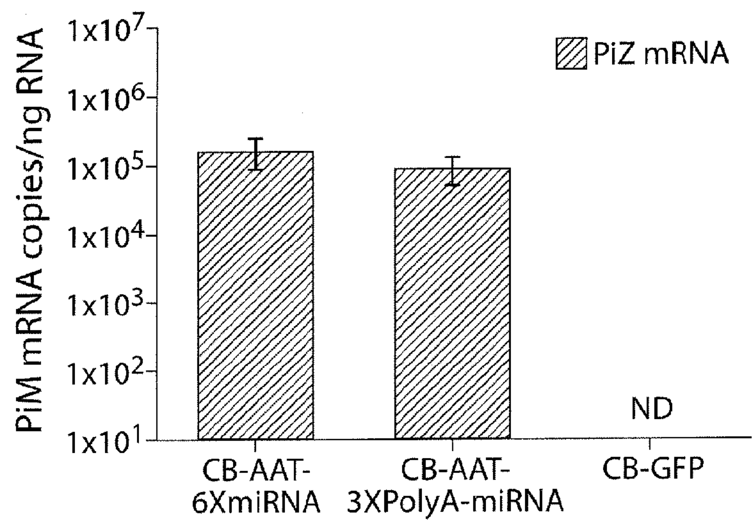

Surprisingly, while the knockdown for both vectors was similar four weeks post delivery, the production of M-AAT was substantially different. The PolyA-3XmiR-CB-AAT vector produced 8-10 times more M-AAT than the Double-6XmiR-CB-AAT vector. Liver RNA was extracted from these mice at the end of the study to quantify the mRNA levels of Z-AAT and M-AAT. A precipitous decrease in Z-AAT mRNA occurred in both cohorts of mice receiving vectors with miRNAs as compared to mice receiving a rAAV9-CB-GFP control (FIG. 8B). A quantitative RT-PCR for M-AAT was also performed, to verify production of M-AAT at the RNA level and to determine if the difference in M-AAT production between dual-function vectors was related to mRNA transcription. Despite the clear difference in M-AAT serum protein levels, there was no statistically significant difference in the M-AAT mRNA levels between the two groups (FIG. 8C). This indicates that mRNA processing and translation but not the level of transcription may be affected in the Double-6XmiR-CB-AAT group, in some cases.

Analysis of Global Liver miRNA Profiles after Delivery of Artificial miRNAs with rAAV9

A microarray analysis of endogenous mouse miRNAs from liver tissue for 6 groups of mice with 5 mice per group was performed on 30 separate microfluidic chips using samples obtained from the long-term Z-AAT knockdown experiments (FIG. 6), along with 5 untreated Z-AAT transgenic mice and 5 C57/BL6 mice. In order to determine basal differences imparted by the human Z-AAT gene in mice, an initial comparison between untreated PiZ mice and wildtype C57BL6 mice was performed. As shown in FIG. 9*a* and Table 3, there were only 4 statistically significant differences among these mice with only miR-1 having a log 2 ratio greater than 2, being upregulated in PiZ mice. The effects of rAAV9-CB-GFP, rAAV9-Double-6XmiR-CB-GFP, rAAV9-PolyA-3XmiR-CB-GFP and rAAV9-intronic-3XmiR-CB-GFP liver transduction on liver miRNA profiles were compared. Surprisingly the expression of the artificial vector derived miRNAs had minimal impact on global miRNA profiles (see FIG. 9*b-d*). Statistically significant differences between untreated PiZ mice and rAAV9 treated mice were observed in 2-6 differentially expressed miRNAs. Of these differentially expressed miRNAs the one with the largest change was miR-1 which was down-regulated back down to levels observed in the C57B16. This correction of miR-1 up-regulation in PiZ mice was observed in all groups including the mice receiving only rAAV9-GFP. Thus it seems to be dependent on rAAV9 delivery and not on artificial miRNA delivery.

The results presented in these examples describe a combinatorial therapeutic approach for the treatment of both liver and lung disease present in alpha-1 antitrypsin deficiency. This therapeutic approach is based on a single dual function AAV vector to deliver both miRNAs targeting AAT for clearance of mutant mRNA along with a miRNA resistant AAT cDNA for augmentation of wild-type protein. The data presented herein support this approach as the biological activities of the miRNAs are demonstrated both by cell culture experiments, and in vivo after numerous experiments with tail vein delivery of rAAV9-pseudotyped vectors. Depending on the configuration of the miRNAs, a long-term knockdown of circulating serum Z-AAT in a range of 50-95% was consistently achieved. Furthermore, in the case of dual function vectors this knockdown was accompanied by equally sustained expression and secretion of wild-type M-AAT.

Knockdown of mutant Z-AAT protein is observed in PiZ transgenic mice using a rAAV8 vector expressing U6 driven shRNAs. Initial cell culture experiments determined that by 72 hours the efficiency of the miRNAs used in this study were comparable to shRNAs (FIG. 1). The in vivo experiments described herein corroborated this finding, as a significant decrease in Z-AAT was observed with administration of the rAAV9-CBintronic3xmiR-GFP rAAV9 vector (FIG. 2). These experiments also highlighted an enhanced effect that was obtained by using 3 anti-AAT miRNAs with different target sequences as none of the vectors with a single miRNA achieved the level of knockdown seen when they were delivered in combination (FIG. 2). Another biological effect aside from Z-AAT serum reduction that was observed included a significant and widespread decrease in the accumulation of Z-AAT within the hepatocytes and a reduction of the inflammatory lymphocyte foci within the liver (FIG. 3).

Surprisingly, anti-AAT miRNA efficacy was improved by altering the location of the miRNA within the expression cassette. Initial short-term experiments demonstrated that expressing the miRNAs from the 3' end of the GFP gene rather than from the intron of the CB promoter lead to a 25% increase in the silencing capabilities of the miRNAs and also a to significant decrease in the variability of this effect. Furthermore, doubling the effective miRNA dose per vector by having the miRNAs expressed from both locations did lead to more rapid onset of Z-AAT knockdown (FIG. 4). Moreover, increased miRNA production was seen for both the PolyA-3XmiR-CB-GFP and the Double-6XmiR-CB-GFP vectors as compared to the rAAV9-intronic3xmiR-GFP vector. This indicates that, in some embodiments, miRNA processing from the intron of the CB promoter may be not as efficient as from the 3' end of the GFP gene. In other embodiments, long-term experiments showed that initial kinetic differences in knockdown from the three vectors wanes overtime and by eight weeks the intronic3xmiR-GFP decreases in variability and augments in silencing efficacy.

The potency and stability of the decrease in serum Z-AAT observed in vivo suggests that either of these vectors would lower Z-AAT levels in Pi*ZZ patients to therapeutic levels, even below those seen in Pi*MZ heterozygote patients. However, in some cases, maximal clinical benefit would be derived from a concomitant rise in M-AAT circulation. In this regard, the dual function vectors were designed to also deliver a miRNA-resistant M-AAT cDNA. Cell culture experiments showed the feasibility of this strategy as was shown by a decrease in Z-AAT specific mRNA with a simultaneous rise in M-AAT using a single pro-viral plasmid (FIG. 7). These experiments supported an in vivo study of the dual function vectors. The results from those experiments confirmed the in vitro data, clearly demonstrating the feasibility of concomitant knockdown and augmentation of mutant and wild-type protein respectively. These experiments also revealed that the double configuration of miRNAs had a more rapid onset of Z-AAT knockdown but the overall efficacy over time was comparable to the PolyA-3XmiR-CB-AAT vector. In addition to improved knockdown kinetics of the Double-6XmiR-CB-AAT vector, a decreased output of M-AAT was also observed (FIG. 8*a*). Initially it was hypothesized that this may have been a result of decreased M-AAT mRNA production due to the presence of miRNA within the intron of this construct, but as shown in FIG. 8*c*, there was a statistically significant difference in M-AAT mRNA was not observed between the two groups. While mRNA transcription and stability are not affected by the presence of miRNAs within the intron, their translation into protein may be hindered as observed in the decrease circulating M-AAT levels in the serum of these mice.

Figure 9:
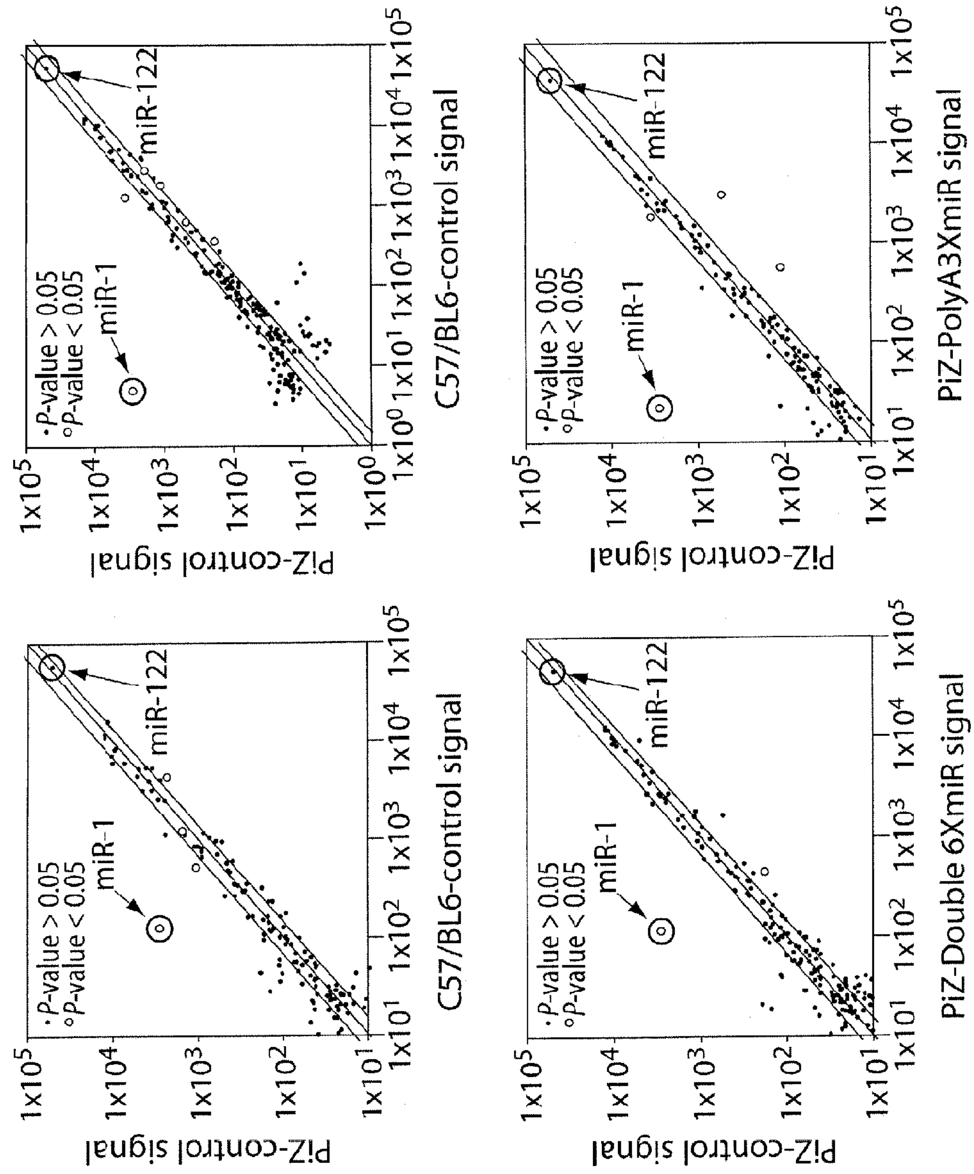
FIG. 9 Artificial miRNA have minimal impact on endogenous miRNA liver profiles. Liver RNA was harvested 3 months post delivery from animals injected with the following vectors: intronic-3XmiR-GFP, PolyA-3XmiR-GFP, Double-6XmiR-GFP, CB-GFP along with RNA form untreated PiZ mice and wildtype C57B16 mice was used to run a miRNA microarray. Each group consisted of 5 mouse RNA samples and was run independently with a single color (Cy5) microarray.

A consideration for a clinical therapy is an effect of artificial miRNA expression on the endogenous miRNA profiles of the target organ. In order to determine if rAAV9 expressed anti-AAT miRNAs were disturbing the endogenous miRNA profiles of the liver, the livers of 30 mice were interrogated at the end of the study described in FIG. 6 with a miRNA microarray. As can be observed from FIG. 9, neither did the delivery of rAAV9-GFP or of the vectors expressing miRNAs have a significant impact on miRNA profiles. Notably, mir-122 which is the most abundant miRNA produced in the liver was unaffected in any group. While some miRNAs were found to be expressed at statistically different levels among the groups, they were mostly on the border of having a 2-fold change with one exception. Interestingly, mir-1 seemed to consistently have upwards of a 2-fold change with rAAV9 intervention. In the case of this miRNA the fold change with rAAV intervention was in the direction of reverting the levels back to those found in wildtype C57BL6 mice (FIG. 9*a*). Thus, in summary, miRNA profiles were unperturbed and in some cases 'corrected' back to wildtype levels with rAAV9 delivery.

These findings indicate that other diseases states requiring the combination of augmentation of a functional allele and suppression of a mutant allele may be addressed in a similar fashion. One such example is Huntington Disease (HD), in which mutant alleles cause a severe autosomal dominant disease, but in which an allele-specific knockdown might only be feasible if the functional allele were modified to convey resistance to a miRNA-based knockdown. It is also significant that these manipulations result in minimal perturbations of endogenous miRNA profiles. This is potentially important for considering the safety of single agent miRNA-based approaches, which would be useful in other anti-viral therapies, e.g., therapies directed against HBV or HCV. As with the genetic diseases considered above, these are conditions in which the down-regulation of target genes for prolonged periods of time may be advantageous. Therefore, emergence of the rAAV-based miRNA platform as a means to address these problems would be useful as well.

TABLE 2

| Artificial miRNA sequences |
|---|
| miRNA910 (SEQ ID NO: 21)<br>5'-<br>TAAGCTGGCAGACCTTCTGTCGTTTTGGCCACTGAGTGACGACAGAAGCT<br>GCCAGCTTA |
| miRNA914 (SEQ ID NO: 22)<br>5'-<br>AATGTAAGCTGGCAGACCTTCGTTTTGGCCACTGACTGACGAAGGTCTCA<br>GCTTACATT |
| miRNA943 (SEQ ID NO: 23)<br>5'-<br>ATAGGTTCCAGTAATGGACAGGTTTGGCCACTGACTGACCTGTCCATCTG<br>GAACCTAT |

TABLE 3

Statistically significant changes in liver miRNA profiles

| Reporter Name | p-value | Group 1 Mean Intensity (n = 5) | Group 2 Mean Intensity (n = 5) | Log2 (G2/G1) |
|---|---|---|---|---|
| | | B6-Control | PiZ-Control | |
| mmu-miR-762 | 2.39E−02 | 525 | 1,099 | 1.07 |
| mmu-miR-23a | 4.03E−02 | 1,247 | 1,593 | 0.35 |
| mmu-miR-1 | 4.95E−02 | 126 | 2,776 | 4.46 |
| mmu-miR-341* | 4.97E−02 | 4,340 | 2,287 | −0.92 |
| | | PiZ-GFP | PiZ-Control | |
| mmu-miR-1 | 6.03E−03 | 5 | 2.776 | 9.13 |
| mmu-miR-148a | 7.48E−03 | 1,841 | 1,058 | −0.80 |
| mmu-miR-720 | 9.33E−03 | 1,264 | 3,440 | 1.44 |
| mmu-miR-30c | 1.03E−02 | 2,830 | 1,757 | −0.69 |

TABLE 3-continued

| Statistically significant changes in liver miRNA profiles | | | | |
|---|---|---|---|---|
| Reporter Name | p-value | Group 1 Mean Intensity (n = 5) | Group 2 Mean Intensity (n = 5) | Log2 (G2/G1) |
| mmu-miR-146a | 1.71E−02 | 362 | 175 | −1.05 |
| mmu-miR-30d | 4.64E−02 | 627 | 454 | −0.47 |
| | | PiZ-PolyA | Piz-Control | |
| mmu-miR-2145 | 1.40E−02 | 573 | 114 | −2.32 |
| mmu-miR-1 | 2.82E−02 | 22 | 2,776 | 6.95 |
| mmu-miR-690 | 2.41E−02 | 3.071 | 534 | −2.52 |
| mmu-miR-720 | 4.31E−02 | 1,816 | 3,440 | 0.92 |
| | | PiZ-6X | PiZ-Control | |
| mmu-miR-146a | 1.53E−02 | 445 | 175 | −1.35 |
| mmu-miR-1 | 3.04E−02 | 115 | 2,776 | 4.59 |

REFERENCES

1. Propst, T. et al. Prevalence of hepatocellular carcinoma in alpha-1-antitrypsin deficiency. J Hepatol 21, 1006-11 (1994).

2. Sivasothy, P., Dafforn, T. R., Gettins, P. G. & Lomas, D. A. Pathogenic alpha 1-antitrypsin polymers are formed by reactive loop-beta-sheet A linkage. J Biol Chem 275, 33663-8 (2000).

3. Lomas, D. A., Evans, D. L., Finch, J. T. & Carrell, R. W. The mechanism of Z alpha 1-antitrypsin accumulation in the liver [see comments]. Nature 357, 605-7 (1992).

4. Brantly, M. L. et al. Phase I trial of intramuscular injection of a recombinant adeno-associated virus serotype 2 alpha1-antitrypsin (AAT) vector in AAT-deficient adults. Hum Gene Ther 17, 1177-86 (2006).

5. Flotte, T. R. et al. Phase I trial of intramuscular injection of a recombinant adeno-associated virus alpha 1-antitrypsin (rAAV2-CB-hAAT) gene vector to AAT-deficient adults. Hum Gene Ther 15, 93-128 (2004).

6. Zern, M. A. et al. A novel SV40-based vector successfully transduces and expresses an alpha 1-antitrypsin ribozyme in a human hepatoma-derived cell line. Gene Ther 6, 114-20 (1999).

7. Fire, A. et al. Potent and specific genetic interference by double-stranded RNA in *Caenorhabditis elegans*. Nature 391, 806-11 (1998).

8. Cruz, P. E. et al. In vivo post-transcriptional gene silencing of alpha-1 antitrypsin by adeno-associated virus vectors expressing siRNA. Lab Invest 87, 893-902 (2007).

9. Grimm, D. et al. Fatality in mice due to oversaturation of cellular microRNA/short hairpin RNA pathways. Nature 441, 537-41 (2006).

10. McBride, J. L. et al. Artificial miRNAs mitigate shRNA-mediated toxicity in the brain: implications for the therapeutic development of RNAi. Proc Natl Acad Sci USA 105, 5868-73 (2008).

11. Denli, A. M., Tops, B. B., Plasterk, R. H., Ketting, R. F. & Hannon, G. J. Processing of primary microRNAs by the Microprocessor complex. Nature 432, 231-5 (2004).

12. Vaucheret, H., Vazquez, F., Crete, P. & Bartel, D. P. The action of ARGONAUTE1 in the miRNA pathway and its regulation by the miRNA pathway are crucial for plant development. Genes Dev 18, 1187-97 (2004).

13. Gao, G. P. et al. Novel adeno-associated viruses from rhesus monkeys as vectors for human gene therapy. Proc Natl Acad Sci USA 99, 11854-9 (2002).

14. Li, H. et al. Ex vivo transduction and transplantation of bone marrow cells for liver gene delivery of alpha1-antitrypsin. Mol Ther 18, 1553-8 (2010).

15. Gao, X., Gulari, E. & Zhou, X. In situ synthesis of oligonucleotide microarrays. Biopolymers 73, 579-96 (2004).

16. Bolstad, B. M., Irizarry, R. A., Astrand, M. & Speed, T. P. A comparison of normalization methods for high density oligonucleotide array data based on variance and bias. Bioinformatics 19, 185-93 (2003).

17. Naldini, L. Ex vivo gene transfer and correction for cell-based therapies. Nature Reviews Genetics 12, 301-315 (2011).

18. Loiler, S. A., Conlon, T. J., Song, S., Tang, Q., Warrington, K. H., Agarwai, A., Kapturczak, M., Li, C., Ricordi, C., Atkinson, M. A., Muzyczka, N., and Flotte, T. R. Targeting recombinant adeno-associated virus vectors to enhance gene transfer to pancreatic islets and liverGene Therapy (2003) 10, 1551-1558).

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The entire contents of all references, publications, abstracts, and database entries cited in this specification are incorporated by reference herein.

What is claimed is:

1. A recombinant adenoviral associated vector (rAAV) comprising:

(a) a first region that encodes one or more first miRNAs comprising a nucleic acid having sufficient sequence complementary with an endogenous mRNA of a subject to hybridize with and inhibit expression of the endogenous mRNA, wherein the endogenous mRNA encodes a mutant alpha anti-trypsin (AAT) protein; and (b) a second region encoding an exogenous mRNA that encodes a second protein, wherein the second protein is a wild-type AAT protein, wherein the exogenous mRNA has one or more silent mutations as compared with the endogenous mRNA, wherein the one or more first miRNAs do not comprise a nucleic acid having sufficient sequence complementary to hybridize with and inhibit expression of the exogenous mRNA, and wherein the first region is positioned between a portion of the second region encoding the last codon of the exogenous mRNA and a polyadenylation sequence of the exogenous mRNA.

2. The rAAV of claim 1, further comprising a third region encoding a one or more second miRNAs comprising a nucleic acid having sufficient sequence complementary to hybridize with and inhibit expression of the endogenous mRNA, wherein the third region is positioned within an untranslated portion of the second region.

3. The rAAV of claim 2, wherein the third region is between the first codon of the exogenous mRNA and a position 1000 nucleotides upstream of the first codon.

4. The rAAV of claim 1, wherein the first region encodes two first miRNAs.

5. The rAAV of claim 1, wherein the first region encodes three first miRNAs.

6. The rAAV of claim 2, wherein the third region encodes two second miRNAs.

7. The rAAV of claim 2, wherein the third region encodes three second miRNAs.

8. The rAAV of claim 1, wherein the AAT protein is a human AAT protein.

9. A composition comprising the recombinant AAV of claim 1.

10. A kit comprising a container housing the composition of claim 9.

11. A method of expressing Alpha 1-Antitrypsin (AAT) protein in a subject, the method comprising:

administering to a subject an effective amount of a rAAV of claim 1.

12. A method of expressing Alpha 1-Antitrypsin (AAT) protein in a subject, the method comprising:

isolating cells or tissue from a subject;

contacting the cells or tissue with an effective amount of a rAAV of claim 1, thereby producing transfected cells or tissue; and administering the transfected cells or tissue to the subject.

13. The method of claim 12, wherein the tissue is adipose tissue.

* * * * *